US011484342B2

(12) United States Patent
MacDonald et al.

(10) Patent No.: US 11,484,342 B2
(45) Date of Patent: Nov. 1, 2022

(54) COLPOTOMY CUP ASSEMBLY

(71) Applicant: GYRUS ACMI, INC., Westborough, MA (US)

(72) Inventors: Jeffrey MacDonald, Bantam, CT (US); Jeffrey Radziunas, Wallingford, CT (US); Lynn MacDonald, Bantam, CT (US); Carollynn Goldenberg, Farmington, CA (US)

(73) Assignee: Gyrus ACMI, Inc., Westborough, MA (US)

( * ) Notice: Subject to any disclaimer, the term of this patent is extended or adjusted under 35 U.S.C. 154(b) by 86 days.

(21) Appl. No.: 17/088,239

(22) Filed: Nov. 3, 2020

(65) Prior Publication Data

US 2021/0137559 A1 May 13, 2021

Related U.S. Application Data

(60) Provisional application No. 62/933,572, filed on Nov. 11, 2019.

(51) Int. Cl.
*A61B 17/42* (2006.01)
*A61B 17/00* (2006.01)
(Continued)

(52) U.S. Cl.
CPC .... *A61B 17/4241* (2013.01); *A61B 17/00234* (2013.01); *A61B 17/32* (2013.01);
(Continued)

(58) Field of Classification Search
CPC . A61B 17/3211; A61B 17/42; A61B 17/4241; A61B 2017/32113; A61B 2017/4216
See application file for complete search history.

(56) References Cited

U.S. PATENT DOCUMENTS 5,133,713 A 7/1992 Huang et al.
5,431,662 A 7/1995 Nicholas
(Continued)

FOREIGN PATENT DOCUMENTS

EP 3068323 A1 9/2016
EP 3146905 A1 3/2017
(Continued)

OTHER PUBLICATIONS

"International Application Serial No. PCT US2020 058738, International Preliminary Report on Patentability dated May 27, 2022", 7 pgs.
(Continued)

*Primary Examiner* — Ryan J. Severson
(74) *Attorney, Agent, or Firm* — Schwegman Lundberg & Woessner, P.A.

(57) ABSTRACT

A medical device for performing a hysterectomy is provided. The medical device has a tissue incision assembly that includes a first cup nested within a second cup. The tissue incision assembly also includes a spacer assembly between the first cup and the second cup in order to maintain a spacing between the first and second cups. The tissue incision assembly also has a cutting implement that has a portion extending between, and movable with respect to, the first and second cups. The cutting implement can provide a circular cut guided via the spacing between the first and second cups.

19 Claims, 52 Drawing Sheets

(51) Int. Cl.
*A61B 17/32* (2006.01)
*A61B 18/14* (2006.01)
*A61B 17/3211* (2006.01)
*A61B 18/00* (2006.01)
*A61B 18/12* (2006.01)

(52) U.S. Cl.
CPC .... *A61B 17/32002* (2013.01); *A61B 17/3211* (2013.01); *A61B 17/320016* (2013.01); *A61B 17/42* (2013.01); *A61B 18/1485* (2013.01); *A61B 18/1492* (2013.01); *A61B 2017/00296* (2013.01); *A61B 2017/00314* (2013.01); *A61B 2017/00389* (2013.01); *A61B 2017/00738* (2013.01); *A61B 2017/00831* (2013.01); *A61B 2017/32113* (2013.01); *A61B 2017/4216* (2013.01); *A61B 2018/00077* (2013.01); *A61B 2018/00083* (2013.01); *A61B 2018/00178* (2013.01); *A61B 2018/00559* (2013.01); *A61B 2018/00601* (2013.01); *A61B 2018/126* (2013.01); *A61B 2018/1253* (2013.01); *A61B 2560/02* (2013.01)

(56) References Cited

U.S. PATENT DOCUMENTS

| | | | |
|---|---|---|---|
| 5,676,663 A | 10/1997 | Kim | |
| 8,298,213 B2 | 10/2012 | Singh | |
| 8,323,278 B2* | 12/2012 | Brecheen | A61B 17/42 606/45 |
| 8,475,469 B2* | 7/2013 | Walter | A61B 17/4241 606/119 |
| 8,495,809 B2* | 7/2013 | Valtchev | A61B 17/4241 128/833 |
| 8,608,738 B2* | 12/2013 | Brecheen | A61B 17/42 606/45 |
| 10,034,687 B2* | 7/2018 | Brecheen | A61B 17/4241 |
| 2001/0021854 A1 | 9/2001 | Donnez et al. | |
| 2004/0102770 A1 | 5/2004 | Goble | |
| 2005/0277948 A1* | 12/2005 | Cedars | A61B 17/4241 606/119 |
| 2008/0154244 A1* | 6/2008 | Singh | A61B 17/4241 606/1 |
| 2009/0131954 A1* | 5/2009 | Christian | A61B 17/4241 606/119 |
| 2009/0171147 A1 | 7/2009 | Lee et al. | |
| 2011/0259344 A1* | 10/2011 | Ahluwalia | A61B 90/04 128/834 |
| 2012/0143209 A1 | 6/2012 | Brecheen et al. | |
| 2012/0143210 A1* | 6/2012 | Brecheen | A61B 18/1482 606/119 |
| 2012/0323079 A1* | 12/2012 | Bakare | A61B 1/303 600/204 |
| 2012/0330324 A1* | 12/2012 | Sauer | A61B 90/30 606/119 |
| 2014/0276812 A1* | 9/2014 | Batchelor | A61B 18/1485 606/48 |
| 2015/0133923 A1* | 5/2015 | Batchelor | A61B 18/1482 606/48 |
| 2016/0095649 A1 | 4/2016 | Motai et al. | |
| 2017/0156756 A1 | 6/2017 | Adajar | |
| 2017/0333077 A1 | 11/2017 | Williams et al. | |
| 2018/0249992 A1 | 9/2018 | Truckey | |
| 2018/0325552 A1 | 11/2018 | Weihe et al. | |
| 2018/0325575 A1* | 11/2018 | Begg | A61B 18/1485 |
| 2019/0216505 A1 | 7/2019 | Meade | |
| 2019/0350622 A1* | 11/2019 | Abou El Kheir | A61B 18/14 |
| 2021/0137546 A1* | 5/2021 | MacDonald | A61B 17/00234 |
| 2021/0137559 A1* | 5/2021 | MacDonald | A61B 17/3211 |
| 2021/0137560 A1* | 5/2021 | MacDonald | A61B 17/4241 |
| 2021/0137590 A1* | 5/2021 | MacDonald | A61B 18/1485 |

FOREIGN PATENT DOCUMENTS

| | | |
|---|---|---|
| EP | 3400894 A2 | 11/2018 |
| WO | WO-03096912 A1 | 11/2003 |
| WO | 2019192793 | 10/2019 |

OTHER PUBLICATIONS

"International Application Serial No. PCT US2020 058735, International Preliminary Report on Patentability dated May 27, 2022", 13 pgs.

"International Application Serial No. PCT US2020 058734, International Preliminary Report on Patentability dated May 27, 2022", 7 pgs.

"International Application Serial No. PCT US2020 058729, International Preliminary Report on Patentability dated May 27, 2022", 9 pgs.

"U.S. Appl. No. 17/088,315, Preliminary Amendment filed Apr. 12, 2022", 8 pgs.

"International Application Serial No. PCT US2020 058734, International Search Report dated Feb. 3, 2021", 5 pgs.

"International Application Serial No. PCT US2020 058734, Written Opinion dated Feb. 3, 2021", 5 pgs.

"International Application Serial No. PCT/US2020/058729, International Search Report dated Feb. 23, 2021", 5 pgs.

"International Application Serial No. PCT/US2020/058729, Written Opinion dated Feb. 23, 2021", 7 pgs.

"International Application Serial No. PCT/US2020/058735, Invitation to Pay Additional Fees dated Feb. 12, 2021", 12 pgs.

"International Application Serial No. PCT/US2020/058738, International Search Report dated Mar. 5, 2021", 4 pgs.

"International Application Serial No. PCT/US2020/058738, Written Opinion dated Mar. 5, 2021", 5 pgs.

Lesca, Tek, "30 Pcs Small Plastic Toggle Double Hole Spring Loaded Elastic Drawstring Rope Cord Locks Clip Ends Luggage Lanyard Stopper Sliding Fastener Buttons", <https://www.amazon.com/Plastic-Elastic-Drawstring-Luggage-Fastener/dp/B077HRN87D>, (Nov. 16, 2017).

"International Application Serial No. PCT US2020 058735, International Search Report dated Apr. 6, 2021", 7 pgs.

"International Application Serial No. PCT US2020 058735, Written Opinion dated Apr. 6, 2021", 11 pgs.

"U.S. Appl. No. 17/088,315, Non Final Office Action dated Aug. 17, 2022", 16 pgs.

* cited by examiner

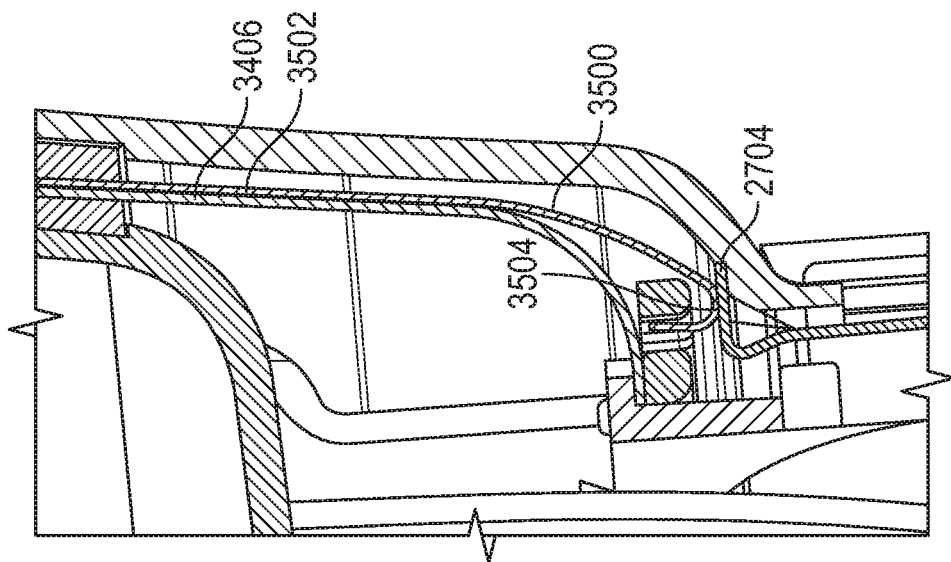
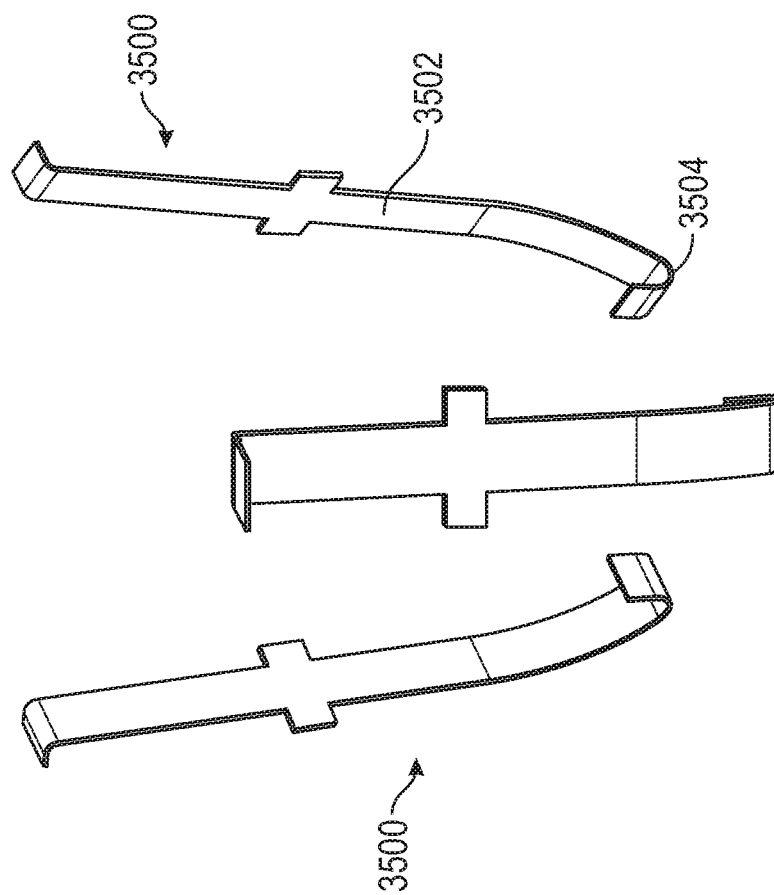
FIG. 36
FIG. 35

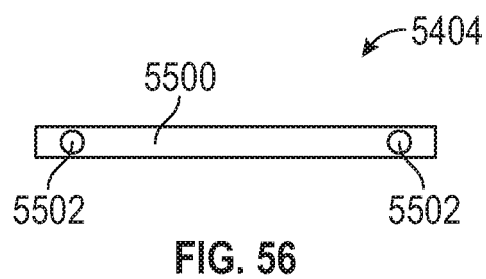
FIG. 55
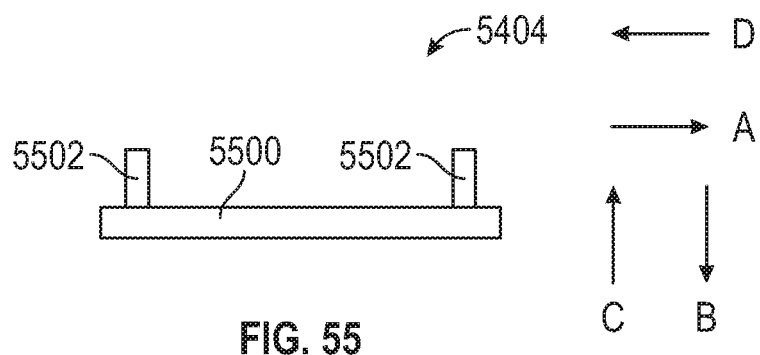
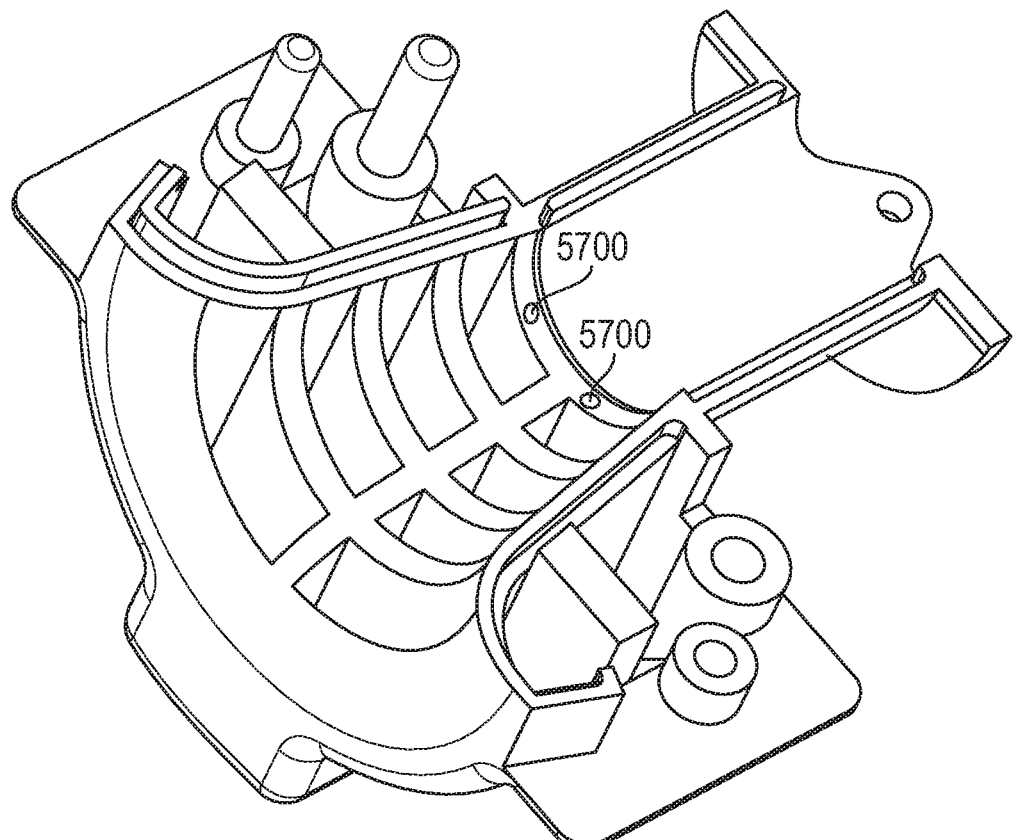
FIG. 56
FIG. 57

US 11,484,342 B2

COLPOTOMY CUP ASSEMBLY

CLAIM FOR PRIORITY

The present application claims priority to Application No. 62/933,572 filed on Nov. 11, 2019, the contents of which are incorporated herein in their entirety.

TECHNICAL FIELD

This document pertains generally, but not by way of limitation, to surgical devices that can be used for various surgical procedures. More specifically, but not by way of limitation, the present application relates to a surgical device that may be used to treat the reproductive system of a female patient.

BACKGROUND

A hysterectomy is a surgical procedure that is used to remove the uterus of a woman. There are a number of conditions that may necessitate a hysterectomy, such as uterine fibroids, uterine prolapse, uterine cancer, endometriosis, chronic pelvic pain, and adenomyosis. Depending on the condition, the entire uterus may be removed or only a portion of the uterus may be removed.

In some instances, a surgeon only removes an upper portion of the uterus during a subtotal hysterectomy. In instances where the entire uterus and the cervix requires removal, a surgeon can perform a total hysterectomy. Additionally, in a radical hysterectomy, a surgeon removes the entire uterus, along with tissue on the sides of the uterus, the cervix, and the top portion of the vagina.

Typically, two different approaches may be used to perform a hysterectomy, open surgery and a minimally invasive procedure. During open surgery, a five to seven inch incision is made in the abdomen of the patient and the uterus is removed through the incision. For a minimally invasive procedure, among others, a total laparoscopic hysterectomy procedure and a laparoscopic supracervical hysterectomy procedure can be performed. Both of these procedures are minimally invasive with shorter recovery times in comparison to open surgery. During a laparoscopic supracervical hysterectomy, the uterus, but not the cervix, is removed using a technique that involves several small abdominal incisions. During a total laparoscopic hysterectomy, small keyhole incisions are made in the navel or abdomen and the uterus is removed in small pieces through either the incisions or the vagina. Recovery times for the procedures described above can range from four weeks to six weeks. Moreover, complications may arise, such as vaginal cuff dehiscence, which may occur when the cutting implement used to separate the uterus wanders a procedure.

Accordingly, a need exists for a procedure and device which facilitates this procedure while minimizing the number of incisions necessary during a hysterectomy, allows for better control of the cutting implement during the hysterectomy, and allows for uniform excision.

SUMMARY

Embodiments of the present disclosure relate to a medical device for performing a hysterectomy. In an embodiment, the medical device can include a tissue incision assembly having first and second cups, where the first cup is nested within the second cup. In an embodiment, a spacer assembly maintains a spacing between the first and second cups. The tissue incision assembly can also include a cutting implement that can be extendable and retractable between the first and second cups where the cutting implement can provide a circular cut, which can be guided by the first and second cups. In an embodiment, the spacer assembly can align the first cup with the second cup such that a probe aperture of the first cup aligns with the second cup. In another embodiment, the spacer can include a bushing that can allow rotation of the cutting implement while the first and second cups remain stationary.

BRIEF DESCRIPTION OF FIGURES

FIGS. 35 and 36 illustrate axial contacts of a cutting device, in accordance with at least one example of the present disclosure.

FIGS. 55 and 56 illustrate a biasing member of the clutch assembly of FIG. 54, in accordance with at least one example of the present disclosure.

FIG. 57 illustrates a housing portion having recesses configured to receive the biasing member of FIGS. 55 and 56, in accordance with at least one example of the present disclosure.

DETAILED DESCRIPTION

Embodiments of the present disclosure relate to a medical device for performing a hysterectomy. In an embodiment, the medical device can include a tissue incision assembly having first and second cups, where the first cup is nested within the second cup. In an embodiment, a spacer assembly maintains a spacing between the first and second cups. The tissue incision assembly can also include a cutting implement that can be extendable and retractable between the first and second cups where the cutting implement can provide a circular cut, which can be guided by the first and second cups. In an embodiment, the spacer assembly can align the first cup with the second cup such that a probe aperture of the first cup aligns with the second cup. In another embodiment, the spacer can include a bushing that can allow rotation of the cutting implement while the first and second cups remain stationary.

Figure 1A:
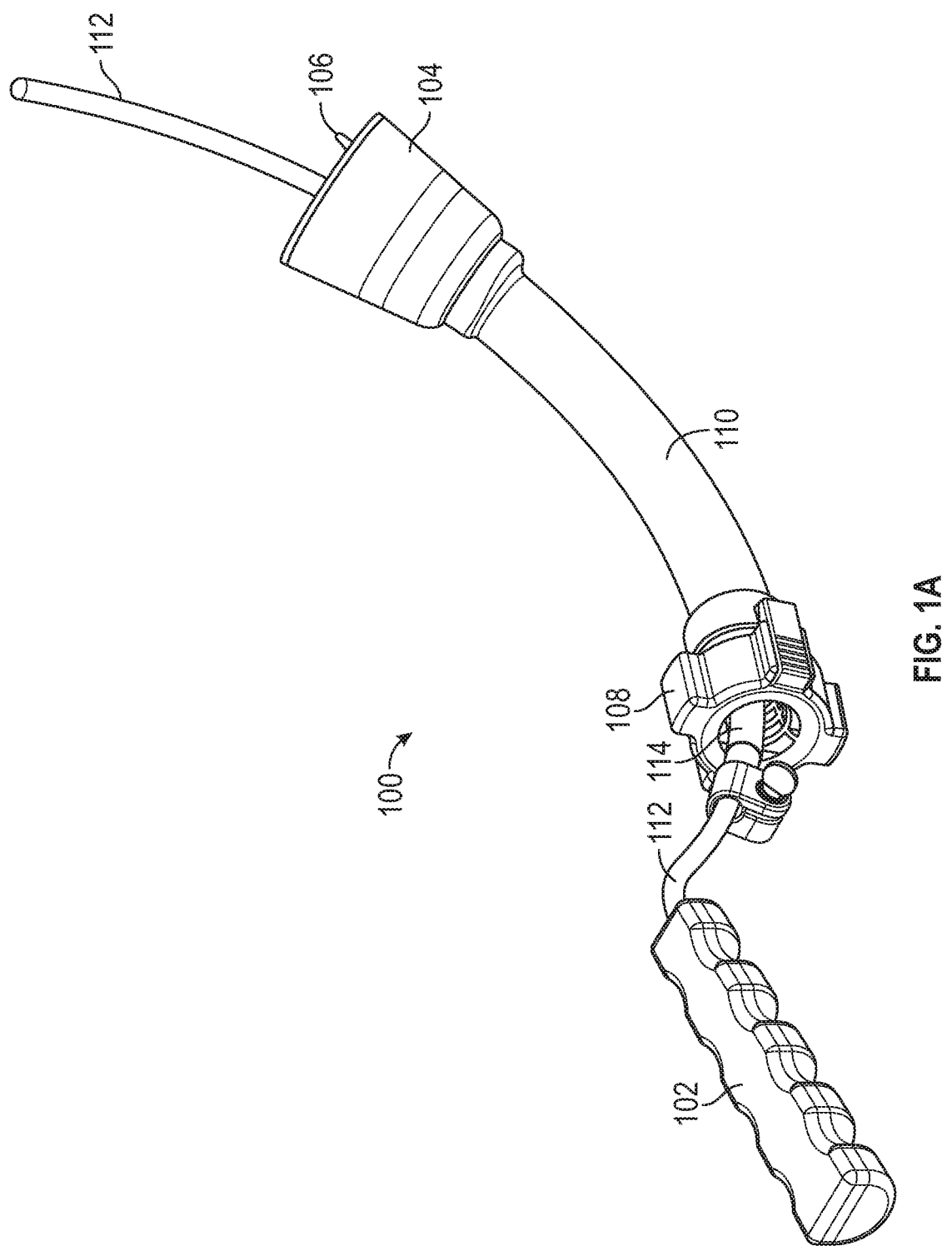
FIGS. 1A and 1B illustrate a colpotomy device having a knob locking assembly at a first end and an end effector assembly at a second end opposite the knob locking assembly with a flexible drive tube disposed between the knob locking assembly and the end effector assembly in accordance with at least one example of the present disclosure.
Figure 1B:
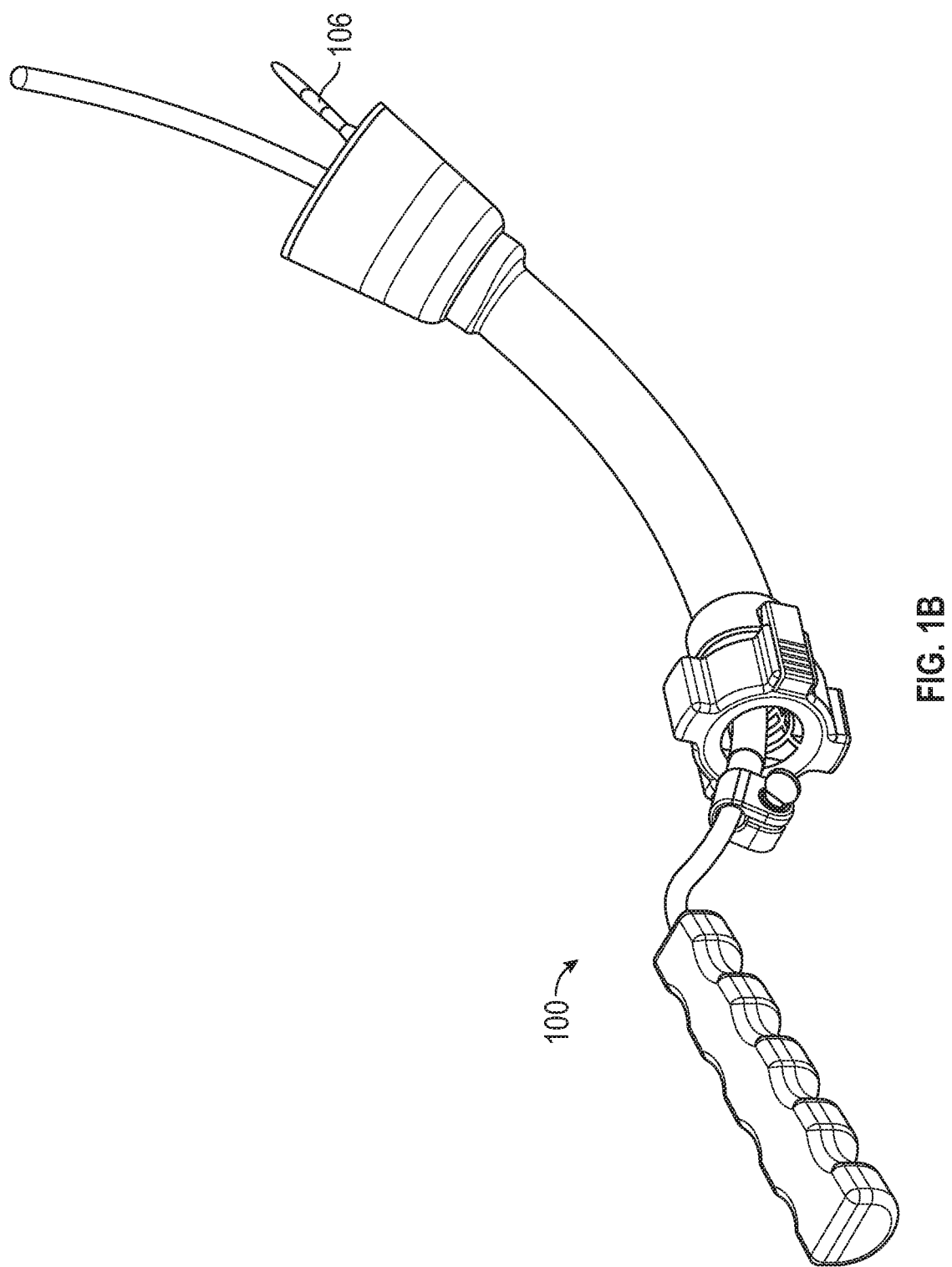

Now making reference to the Figures, and more specifically FIGS. 1A and 1B, a colpotomy device 100 is shown in accordance with at least one example of the present disclosure that can be used for laparoscopic procedures, such as a hysterectomy. The colpotomy device 100 can include a handle 102 at a proximal end of the colpotomy device 100 and an effector assembly 104 at a distal end of the colpotomy device 100 opposite the proximal end. In an embodiment, the handle 102 can be used by surgeon to hold the colpotomy device 100 during a procedure, such as a hysterectomy. The end effector assembly 104 can include an end effector 106, which, as will be discussed further below, can be used to perform a rescission during a hysterectomy. In some embodiments, the end effector assembly 104 can be referred to as a tissue treatment assembly. In addition, the colpotomy device 100 can include a knob locking assembly 108 at the distal end that can be used to manipulate the colpotomy device 100 during a hysterectomy. In particular, the knob locking assembly 108 can be used to manipulate the end effector assembly 104, such as rotating the end effector assembly 104 along with the end effector 106 in a clockwise and counterclockwise direction during use of the colpotomy device 100. Moreover, the knob locking assembly 108 can be used to extend the end effector 106 in a longitudinal direction into the position shown with respect to FIG. 1B and retract the end effector in a longitudinal direction into the position shown with reference to FIG. 1A. The knob locking assembly 108 can be separated from the end effector assembly 104 via a drive tube housing 110, as shown with reference to FIGS. 1A and 1B. In an embodiment, the drive tube housing 110 can be formed of any type of rigid material, such as a rigid plastic, polymer, or the like. Furthermore, a low-friction polymer, such as an acetal resin, polyvinyl chloride (PVC), or the like may be used in accordance with the type of sterilization being used during the procedure. Moreover, in an embodiment, the drive tube housing 110 can have a length that is preferably about 4 inches to 10 inches, and more preferably about 5 inches to about 7 inches. In an embodiment, the drive tube housing 110 can have a diameter that is preferably about 0.5 inches to about 1.5 inches and more preferably about 0.75 inches to about 1.0 inches.

The colpotomy device 100 includes a probe 112 disposed within a lock tube 114. The lock tube 114 may be formed from a flexible material such as flexible polymer, including polyethylene. The lock tube 114 protects the probe 112 within the colpotomy device 100 and allows movements of the colpotomy device 100 along the probe 112 during use of the colpotomy. device 100. During use of the colpotomy device 100, the probe 112 can be used to position the colpotomy device 100 within the vaginal canal of a patient adjacent the cervix in order to allow maneuvering of the end effector assembly 104 such that the end effector assembly 104 can be proximal to the cervix of the patient. When the end effector assembly 104 is adjacent the cervix of the patient, the end effector 106 can be used to perform the hysterectomy. In an embodiment, the flexible sheath 114 encases the probe 112 such that the colpotomy device 100 can move along the probe 112.

Figure 2A:
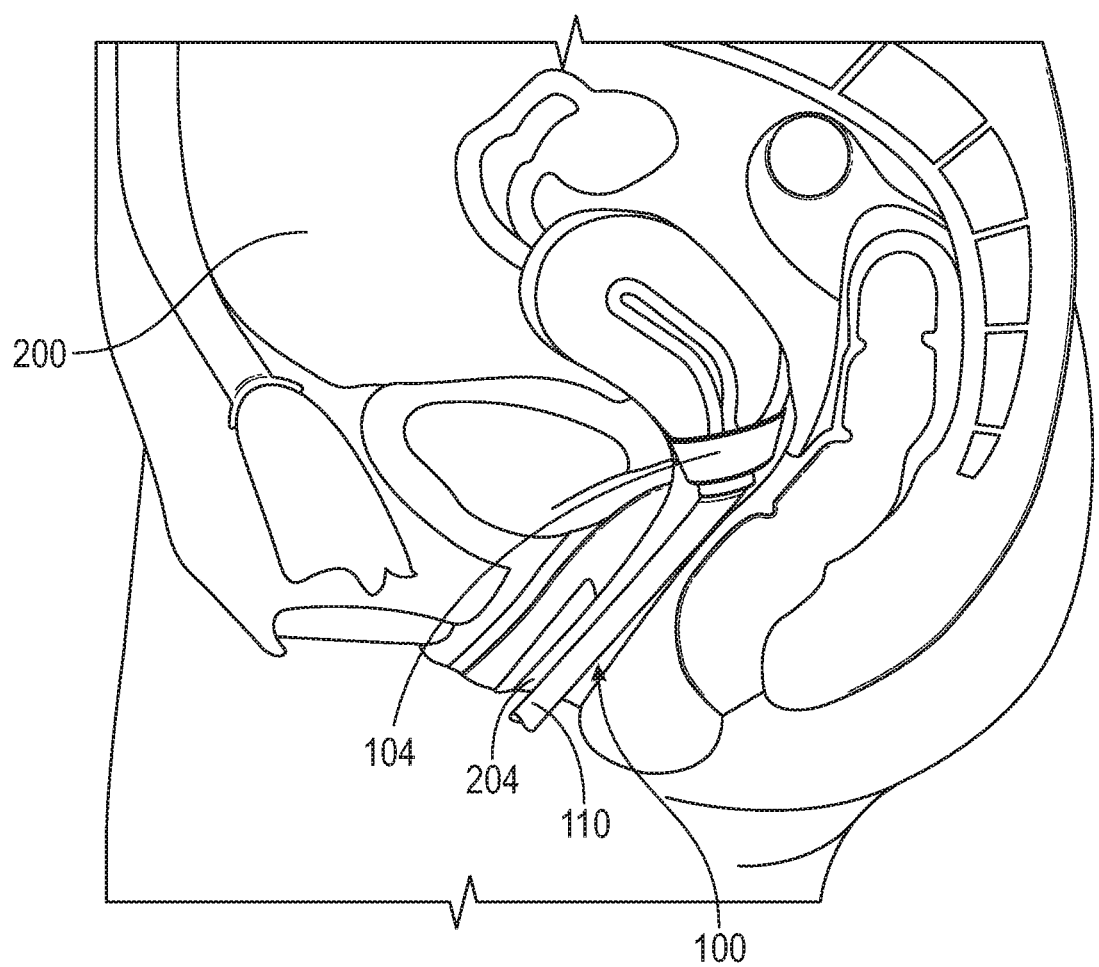
FIGS. 2A and 2B illustrate the use of the colpotomy device of FIGS. 1A and 1B within a patient in accordance with at least one example of the present disclosure.
Figure 2B:
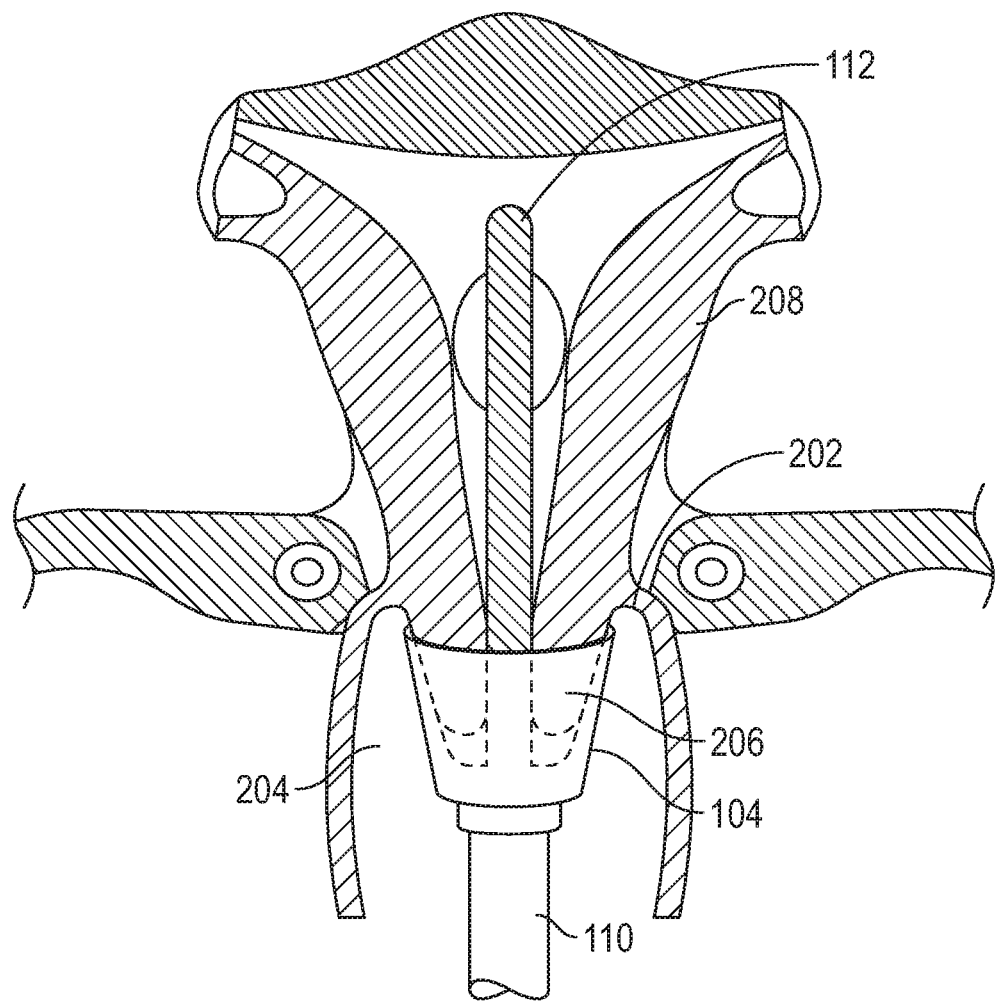

As noted above, the colpotomy device 100 can be used to perform medical procedures, such as a hysterectomy. An example of the colpotomy device 100 being used during a medical procedure is shown with reference to FIGS. 2A and 2B. FIG. 2A illustrates a schematic view of an abdominal cavity 200 of a patient where the colpotomy device 100 engages vaginal fornices 202 of the patient. FIG. 2B is a cross-sectional view of the abdominal cavity of FIG. 2A where the colpotomy device 100 engages the vaginal fornices 202 of the patient. During a medical procedure, such as a hysterectomy, a surgeon inserts the colpotomy device 100 into a vaginal canal 204 of the patient such that the end effector assembly 104 engages with the vaginal fornices 202. More specifically, a surgeon guides the end effector assembly 104 using the probe 112 through the vaginal canal 204 and seats the end effector assembly 104 proximate a cervical end 206 of the vagina of a patient. After placement of the end effector assembly 104, the surgeon may begin resection of a uterus 208 of the patient with the end effector 106 (not shown).

Figure 3:
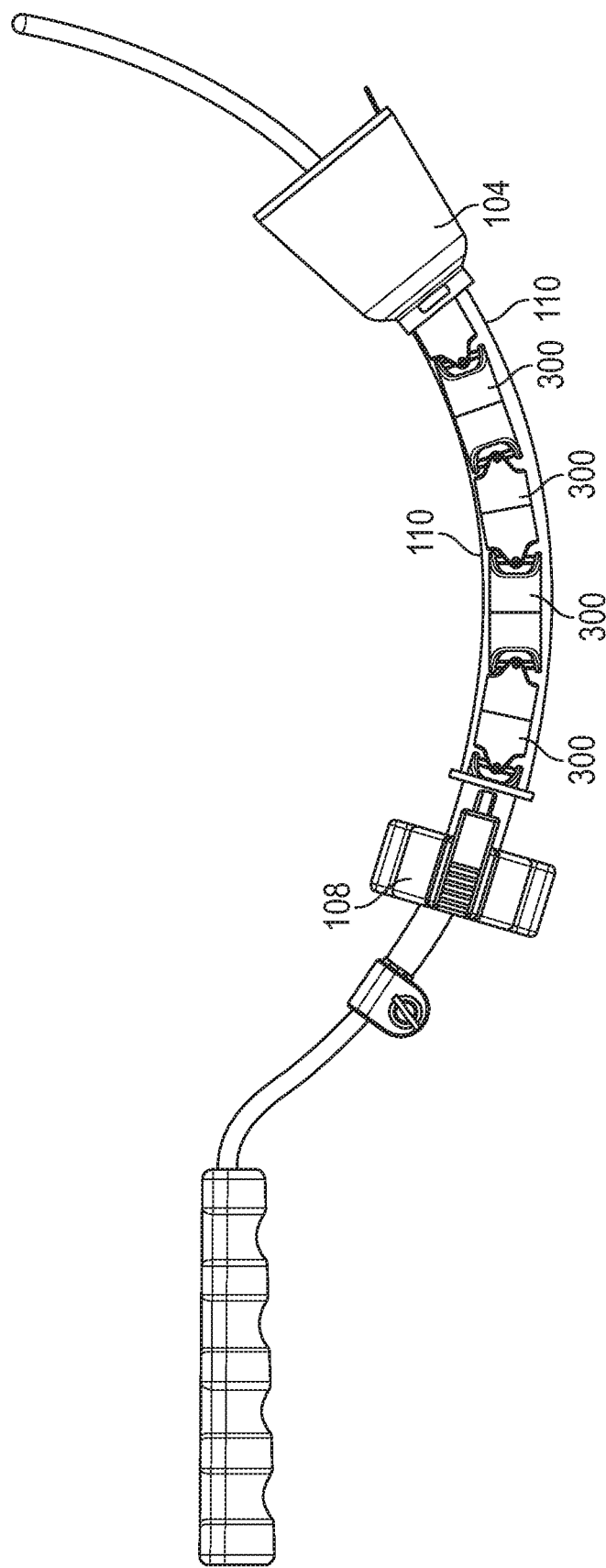
FIGS. 3-5 show couplings of the colpotomy device of FIGS. 1A and 1B in accordance with at least one example of the present disclosure.

Returning attention to the colpotomy device 100, the knob locking assembly 108 can be used to rotate the end effector assembly 104 and extend and retract the end effector 106. In particular, during a resection procedure, such as the resection of the uterus 208, the end effector assembly 104 and the end effector 106 can be rotated to effectuate resection via the knob locking assembly 108. In an embodiment, the colpotomy device 100 can include a plurality of couplings 300 disposed within the drive tube housing 110 and extending between the end effector assembly 104 and the knob locking assembly 108, as shown with reference to FIGS. 3-5. While FIG. 3 illustrates the colpotomy device 100 as including four couplings 300, it should be noted that the colpotomy device 100 can include any number of couplings 300. For example, the colpotomy device can include couplings that number in a range between about four couplings to about twelve couplings. Furthermore, each of the couplings 300 can have a diameter that is preferably about 0.5 inches in diameter to about 1.25 inches in diameter. Moreover, each of the couplings 300 may have a length that is about 0.5 inches in a length to about 1.25 inches in length. In an embodiment, the couplings 300 can be formed of any rigid or semi-rigid material. Examples can include stainless steel, aluminum, titanium, thermoplastics, or any other types of metal alloys.

Figure 4:
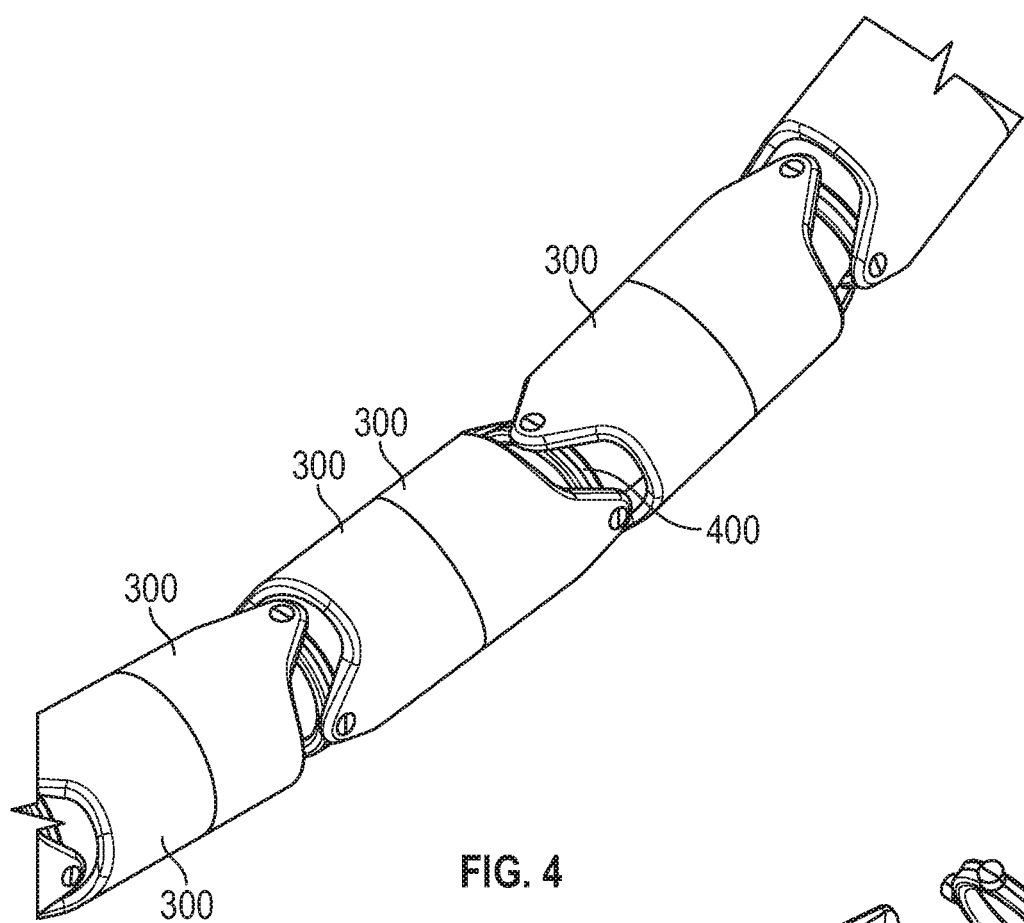
Figure 5:
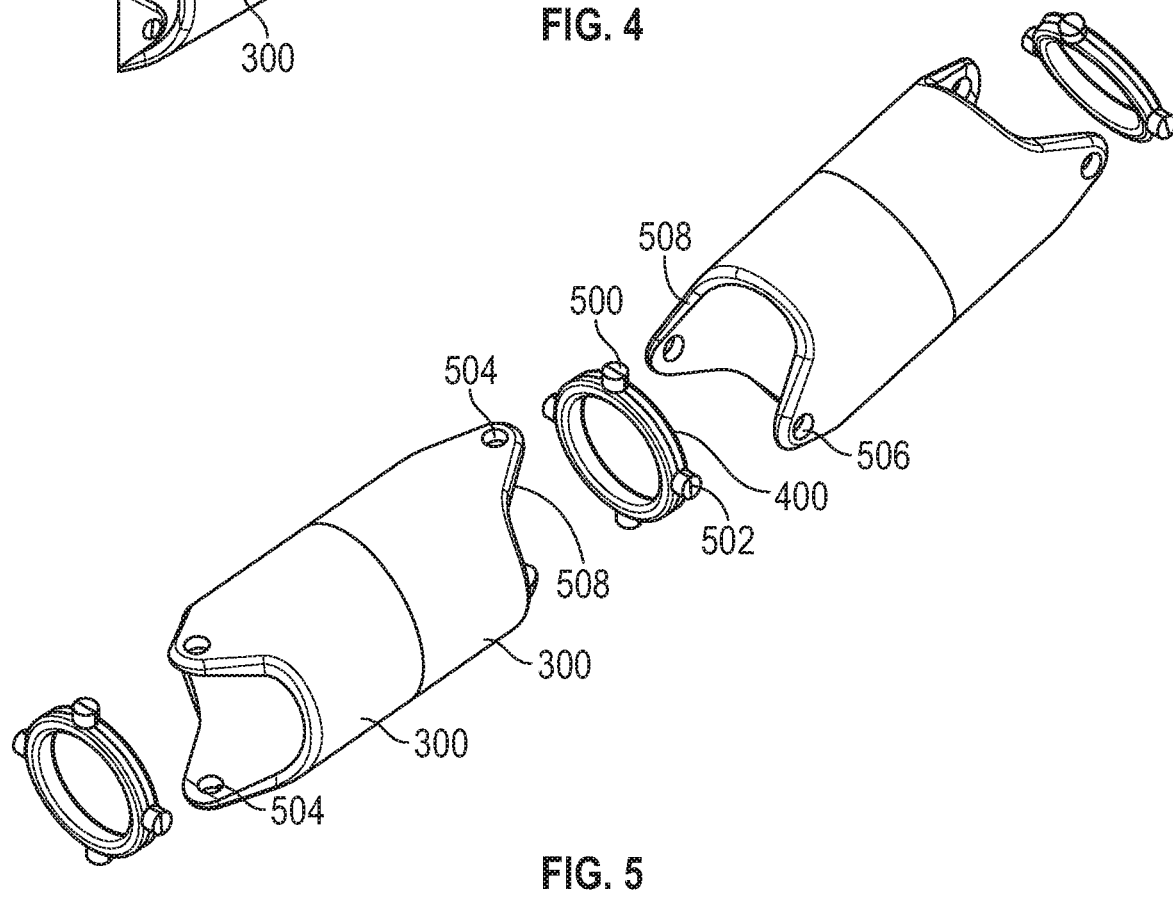

Making reference to FIGS. 4 and 5, each of the couplings 300 can couple to each other via a coupling ring 400 that includes coupling pins 500 and 502. In an embodiment, the couplings 300 can include coupling bores 504 and 506, which can be configured to accept the coupling pins 500 of the coupling ring 400. For example, the coupling bore 504 can be configured to accept the coupling pin 500 such that the coupling pin 500 extends through and is rotatable with respect to the coupling bore 504. In addition, the coupling bore 506 can be configured to accept the coupling pin 502 such that the coupling pin 502 extends through and is rotatable with respect to the coupling bore 506. Furthermore, each of the couplings 300 include a U-shaped portion 508 extending therefrom as shown with reference to FIG. 5. In an embodiment, the U-shaped portions 508 along with the coupling pins 500 and 502 and the coupling bores 504 and 506 form an inter-coupling joint. In an embodiment, the couplings pins 500 and 502 are rotatable with respect to coupling bores 504 and 506 and, in conjunction with the coupling bores 504 and 506 transmit rotational forces through a variable angle between each of the couplings 300.

When the coupling pin 500 is disposed within the coupling bore 504 and the coupling pin 502 is disposed within the coupling bore 506, the couplings 300 can have the configuration shown with reference to FIG. 3. Furthermore, as may be seen with reference to FIG. 3, the couplings 300 may be in series with each other. In an embodiment, the coupling ring 400 along with the coupling pins 500 and 502 can be formed of any rigid or semi-rigid materials. Examples can include stainless steel, aluminum, titanium, thermoplastics, or any other types of metal alloys. Moreover, in an embodiment, the coupling ring 400 can have a diameter that is in a range of about 0.25 inches to about 1.0 inches. In addition, the coupling pins 500 and 502 can have a diameter that is in a range of about 0.05 inches to about 0.10 inches. In addition, the coupling bores 504 and 506 can have a diameter that is in a range of about 0.055 inches to about 0.105 inches.

Figure 6:
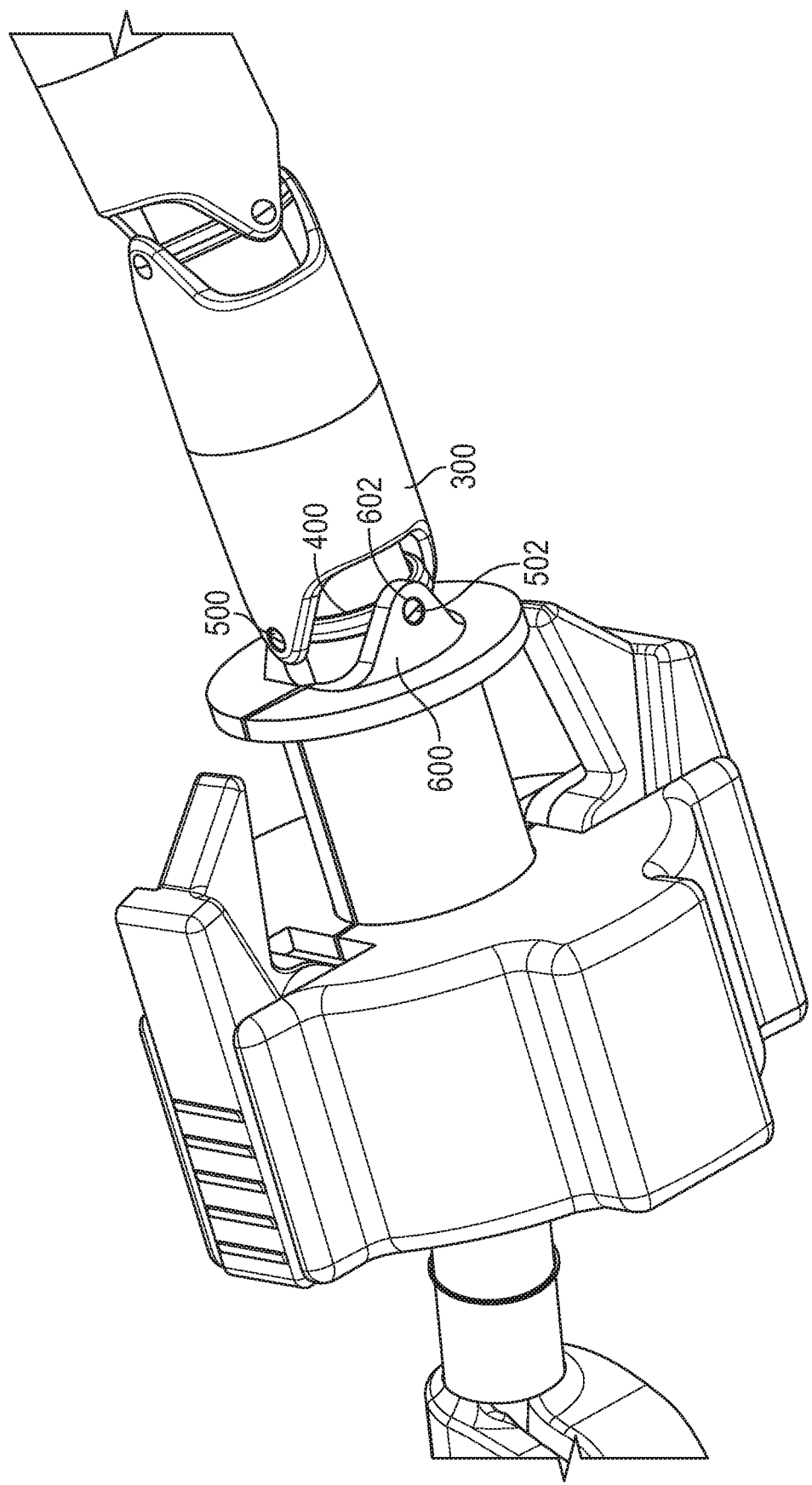
FIG. 6 illustrates a coupling of the couplings of FIGS. 3-5 coupling with the knob locking assembly of FIGS. 1A and 1B in accordance with at least one example of the present disclosure.

As previously mentioned, the drive tube housing 110 along with the couplings 300 extend between the knob locking assembly 108 and the end effector assembly 104. In an embodiment, the couplings 300 can couple with the knob locking assembly 108 at a proximal end of the colpotomy device 100. Furthermore, the couplings 300 can couple with the end effector assembly 104 at a distal end of the colpotomy device 100. For example, making reference to FIG. 6, the knob locking assembly 108 can include a coupling 600 having coupling bores 602. In this embodiment, the knob coupling 600 can couple with the coupling 300 via the coupling ring 400. More specifically, one of the coupling pins 500 and 502 can be disposed within the knob coupling bore 602 while the other of the coupling pins 500 and 502 can be disposed in the coupling bore 506 of the coupling 300. In an embodiment, the knob coupling 600 can have a diameter that is preferably about 0.5 inches in diameter to about 1.25 inches in diameter. In addition, the knob coupling bore 602 can have a diameter that is in a range of about 0.055 inches to about 0.105 inches.

Figure 7A:
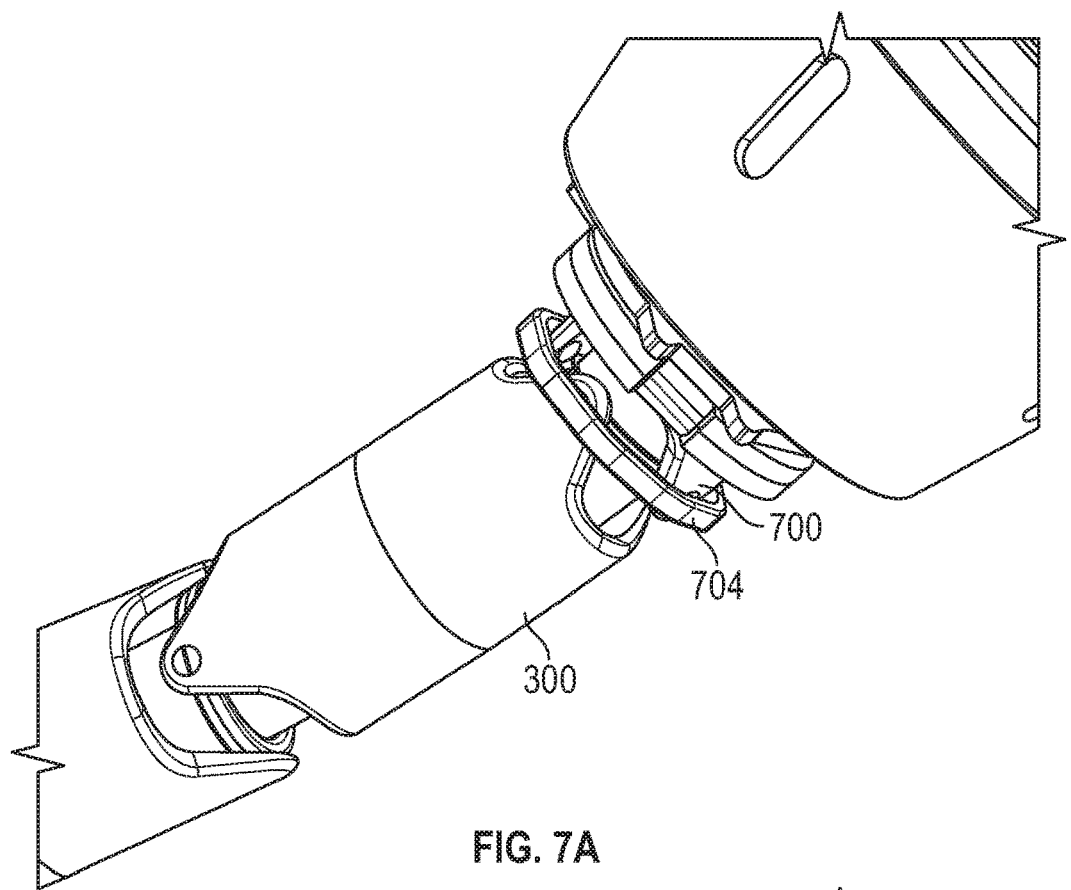
FIGS. 7A and 7B show a coupling of the couplings of FIGS. 3-5 coupling with the end effector assembly of FIGS. 1A and 1B in accordance with at least one example of the present disclosure.
Figure 7B:
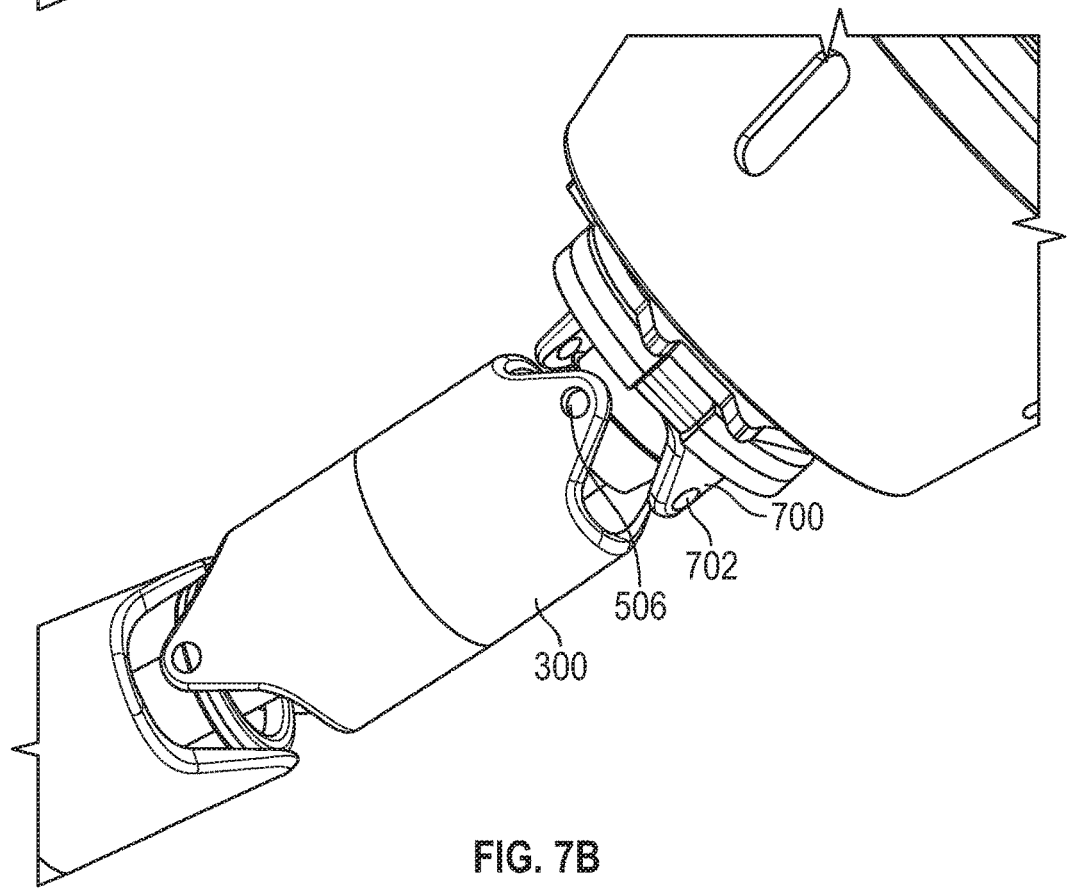
Figure 8:
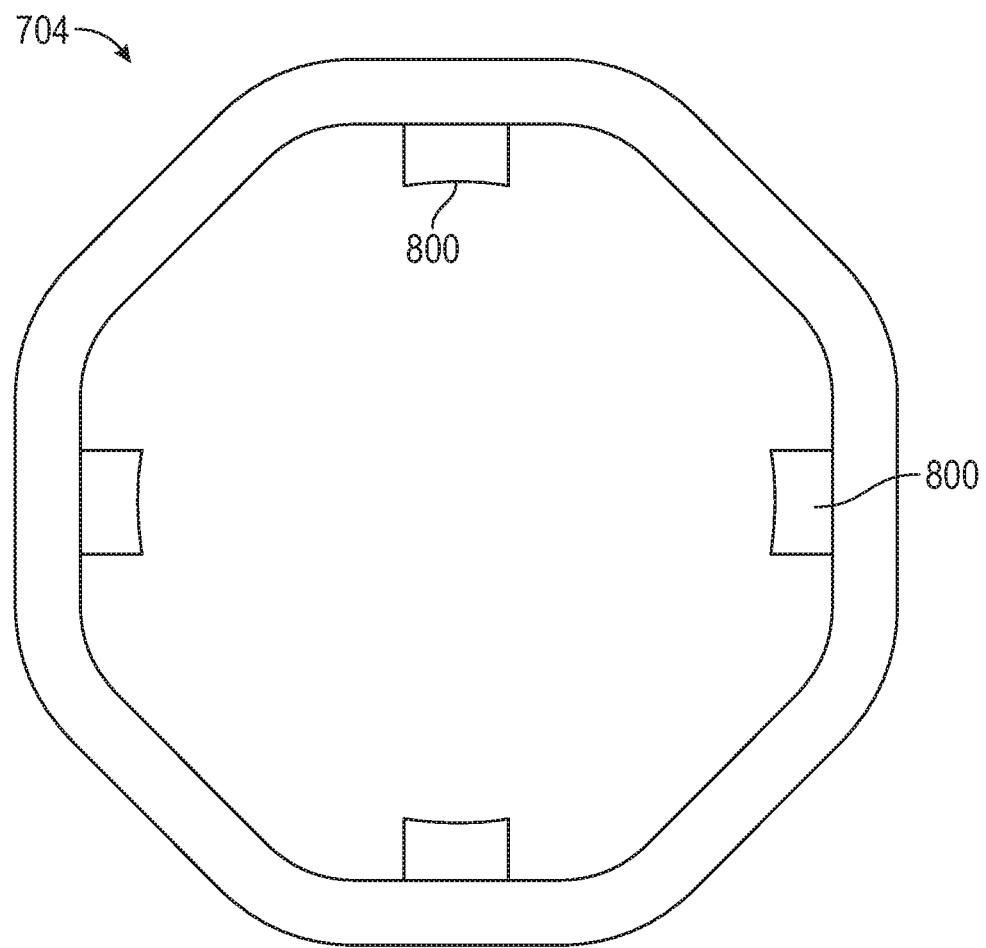
FIG. 8 illustrates an end effector coupling used to couple the end effector assembly of FIGS. 7A and 7B with the coupling of FIGS. 7A and 7B in accordance with at least one example of the present disclosure.

In addition to coupling with the knob locking assembly 108 at the proximal end of the colpotomy device 100, the couplings 300 can couple with the end effector assembly 104 at a distal end of the colpotomy device 100, as shown with reference to FIGS. 7A and 7B. In an embodiment, the end effector assembly 104 can include an end effector assembly coupling 700 having end effector assembly coupling bores 702 (FIG. 7B). In an embodiment, the couplings 300 can couple with the end effector assembly coupling 700 via a coupling ring 704. In particular, as shown with reference to FIG. 8, the coupling ring 704 can include pins 800 where the coupling bores 506 and the end effector assembly coupling bores 702 can be configured to accept the pins 800 of the coupling ring 704 such that the couplings 300 couple with the end effector assembly coupling 700, as shown with respect to FIG. 7A. In an embodiment, the end effector assembly coupling 700 can be formed of any rigid or semi-rigid materials. Examples can include stainless steel, aluminum, titanium, thermoplastics, or any other types of metal alloys. Moreover, in an embodiment, the end effector assembly coupling 700 can have a diameter that is preferably about 0.5 inches in diameter to about 1.25 inches in diameter.

In an embodiment, the couplings 300 can allow for the rotation of the knob locking assembly 108 while the knob locking assembly 108 is in the retracted position, as shown with reference to FIG. 1A. Similarly, the couplings 300 can allow for the rotation of the knob locking assembly 108 while the knob locking assembly 108 is in the extended position, as shown with reference to FIG. 1B. Moreover, when a user rotates the knob assembly 108, the couplings 300 can impart a rotational force imparted at the knob locking assembly 108 through a variable angle with each other in either a first direction or a second direction, such as a clockwise direction or a counterclockwise direction. In an embodiment, the couplings 300 can be constant velocity joints or universal joints such that as the knob locking assembly 108 rotates in either a clockwise or counterclockwise direction, the end effector 106 can also rotate in the same direction as the knob locking assembly 108.

During use of the colpotomy device 100, as noted above, a surgeon can maneuver the colpotomy device 100 and in particular can maneuver the end effector assembly 106 through the vaginal canal 204 of the patient. In an embodiment, as the surgeon moves the end effector assembly 104 through the vaginal canal 204, the end effector 106 can be in a retracted position as shown with reference to FIG. 1A. After the surgeon properly orients the end effector assembly within the abdominal cavity 200 of the patient as shown with regards to FIGS. 2A and 2B, the surgeon can extend the end effector 106 to begin resection using the knob locking assembly 108.

Figure 9:
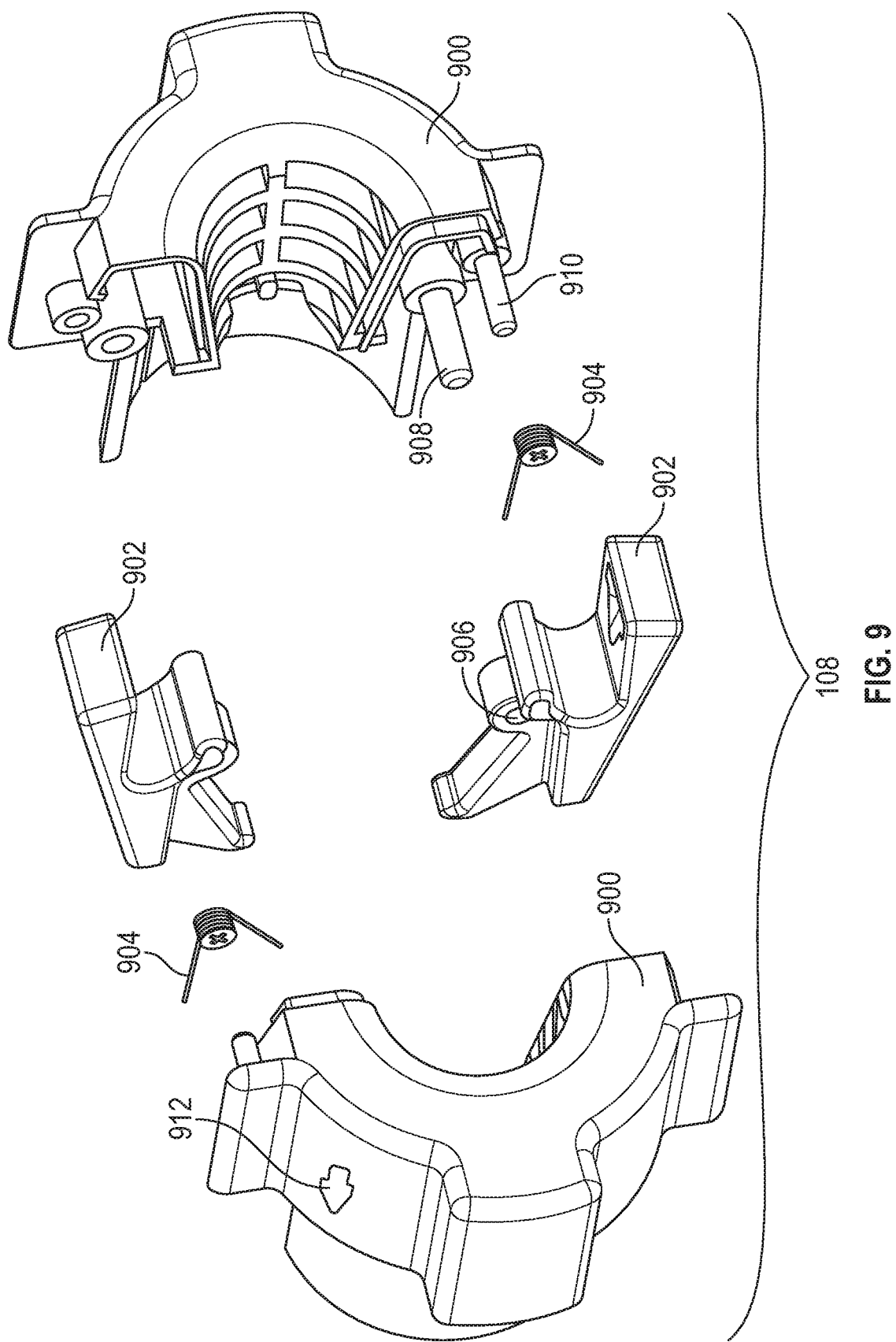
FIG. 9 illustrates a knob locking assembly in accordance with at least one example of the present disclosure.

In an embodiment, the knob locking assembly 108 can function to keep the end effector 106 in the retracted position during maneuvering of the colpotomy device 100 within the vaginal canal 204 and seating of the end effector assembly 104 proximate the cervical end 206. The term knob locking assembly may be used interchangeably with the term knob. Making reference to FIG. 9, an exploded view of the knob locking assembly 108 is shown in accordance with an embodiment of the present disclosure. In an embodiment, the knob locking assembly 108 can include housing portions 900 which together form a housing for the knob locking assembly 108. Furthermore, the knob locking assembly 108 can include actuators 902 and biasing members 904. It should be noted that throughout this Specification, reference will be made to an actuator 902 and actuators 902. These terms are interchangeable. Thus, disclosure relating to the actuator 902 is applicable to the actuators 902 and disclosure relating to the actuators 902 is applicable to the actuator 902. In an embodiment, the actuators 902 include actuator bores 906 which are configured to receive a housing pin 908 of the housing portion 900. In an embodiment, the actuators 902 can be formed of any pliable semi-rigid material. Examples can include any type of polymer, polycarbonate, or the like. Moreover, in an embodiment, the housing portions 900 can include a directional arrow 912, which can provide an indication to a user which direction the knob locking assembly 108 should be moved in order to place the knob locking assembly 108 in an extended position.

Figure 10:
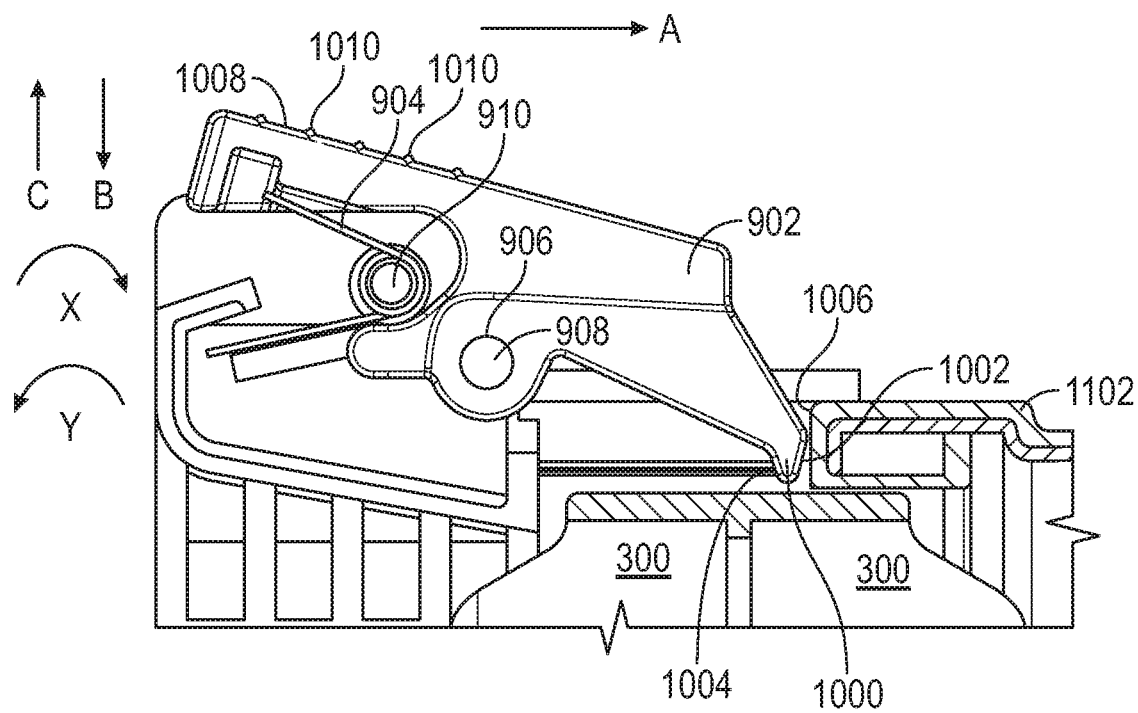
FIG. 10 shows the knob locking assembly of FIG. 9 locked in a retracted position in accordance with at least one example of the present disclosure.
Figure 11:
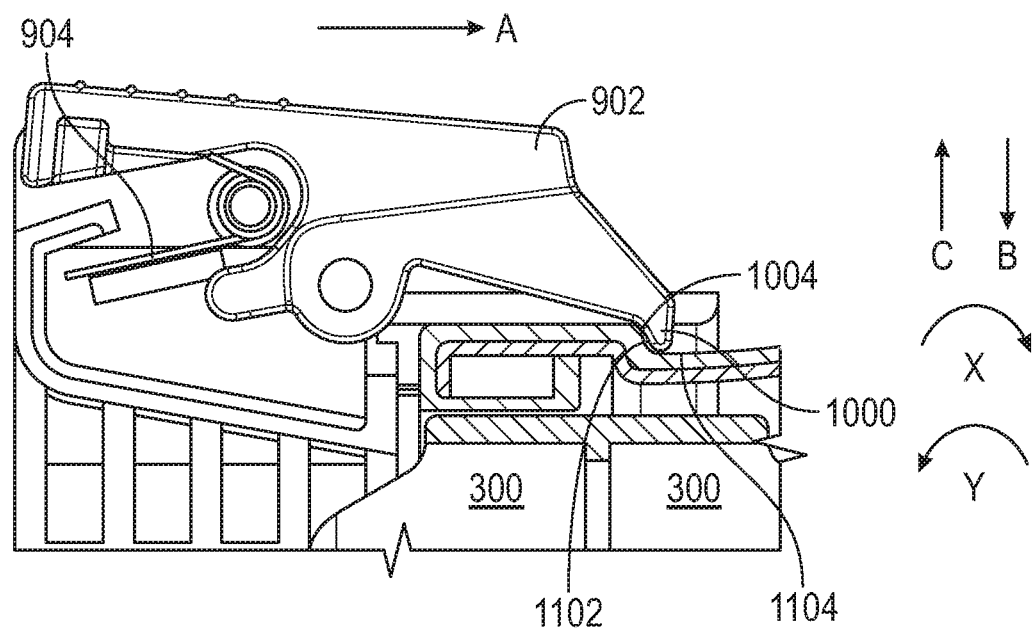
FIG. 11 shows the knob locking assembly of FIG. 9 locked in an extended position in accordance with at least one example of the present disclosure.

The actuators 902 can function to lock the knob locking assembly 108 in either an extended position or a retracted position, as shown with reference to FIGS. 10 and 11. As used herein, the retracted position of the knob locking assembly 108 refers to a position of the knob locking assembly 108 when the end effector 106 can be in the retracted position shown above with reference to FIG. 1A. Moreover, as used herein, the extended position of the knob locking assembly 108 refers to a position of the knob locking assembly 108 when the end effector 106 can be in the extended position shown above with reference to FIG. 1B. In an embodiment, the actuator 902 can include a tab 1000 having a first tab surface 1002 and a second tab surface 1004 opposite the first surface 1002. In the retracted position, the first tab surface 1002 can abut against a flexible drive tube surface 1006 of the drive tube housing 110 such that the flexible drive tube surface 1006 can prevent the knob locking assembly 108 from moving along a direction A. Accordingly, the flexible drive tube surface 1006 functions as a stop for the first tab surface 1002. More specifically, in an embodiment, since the first tab surface 1002 abuts the flexible drive tube surface 1006, the first tab surface 1002 in conjunction with the flexible drive tube surface 1006 can prevent movement of the knob locking assembly 108 along the direction A and, in turn, extension of the end effector 106 from the end effector assembly 104 thereby maintaining the knob locking assembly 108 and the end effector 106 in the retracted position.

Figure 12:
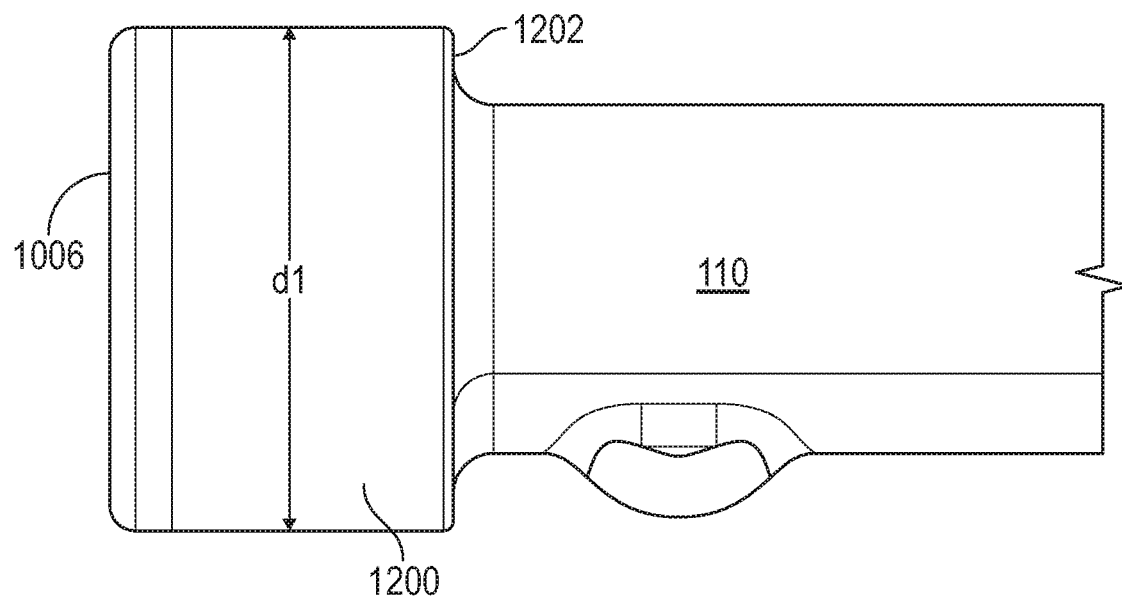
FIG. 12 illustrates an end of the flexible drive tube of FIGS. 1A and 1B in accordance with at least one example of the present disclosure.

Regarding the flexible drive tube surface 1006, now making reference to FIG. 12, a view of a distal end of the drive tube housing 110 is shown in accordance with an embodiment. Here, the drive tube housing 110 can include a flexible tube end 1200 having a diameter $d_1$. In an embodiment, the flexible tube end 1200 can have a diameter $d_1$ that is preferably about 0.5 inches to about 1.5 inches and more preferably about 0.75 inches to about 1.0 inches. In accordance with an embodiment, the diameter $d_1$ can be greater than the diameter of the drive tube housing 110, as discussed above. Due to the diameter variance between the flexible tube end 1200 and the drive tube housing 110, a flexible drive tube surface 1202 is formed on the flexible tube end 1100, as shown with reference to FIG. 12. In an embodiment, the flexible drive tube surface 1202 can function to place the knob locking assembly 108 in the extended position, as will be discussed further on.

Returning attention to FIG. 9, in an embodiment, the biasing means 904 can bias the tab 1000 along a direction X (FIG. 10) such that the actuator 902 can maintain the position shown with reference to FIG. 10 where the first tab surface 1002 abuts the flexible drive tube surface 1006. The biasing means 904 can couple with the housing portion 900 via a housing pin 910. In an embodiment, the biasing means 904 can be a torsion spring. In an embodiment, the biasing means 904 can bias the actuator 902 into the position shown with reference to FIG. 10. Moreover, the biasing means 904 can bias the actuator 902 into the position shown with reference to FIG. 11.

Figure 13:
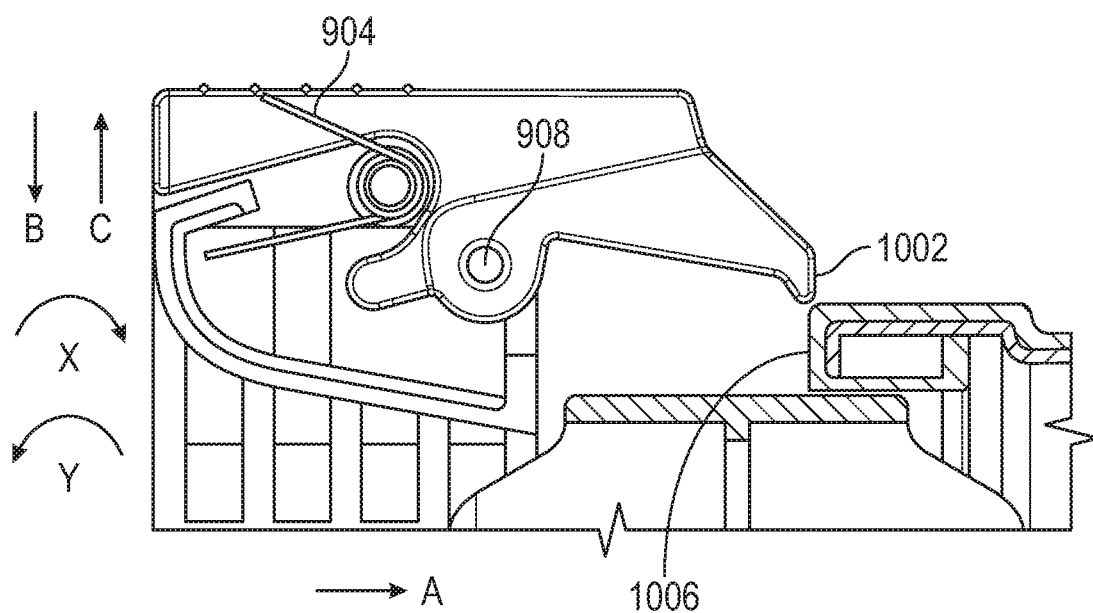
FIG. 13 illustrates the movement of the knob locking assembly of FIG. 9 between a retracted position and an extended position in accordance with at least one example of the present disclosure.

As shown with reference to FIGS. 10 and 11, the actuator 902 can rotate about the housing pin 908 along the direction X or a direction Y. In an embodiment, the knob locking assembly 108 can include an interface 1008 having ridges 1010. In an embodiment, the ridges 1010 can provide a tactile surface such that a user, such as a surgeon, of the colpotomy device 100 can move the knob locking assembly 108 from the retracted position shown with regards to FIG. 10 to the extended position shown with regards to FIG. 13. In particular, a user can push the actuator 902 at the interface 1008 along the direction B, thereby pivoting the actuator along the direction Y about the housing pin 908. As a user pushes the actuator 902 along the direction B and the actuator 902 rotates about the housing pin 908 along the direction Y, the tab 1000 can move along a direction C such that the first tab surface 1002 no longer abuts the flexible drive tube surface 1006. When a user moves the actuator 902 at the interface 1008 along the direction B and the actuator 902 rotates about the housing pin 908, the actuator 902 can have the configuration shown with reference to FIG. 13 where the first tab surface 1002 is above the flexible drive tube surface 1006. Here, the tab 1000 can clear the flexible drive tube surface 1006 and can move over the flexible tube end 1200. Once the first tab surface 1002 clears the flexible drive tube surface 1106 as shown with regards to FIG. 13, a user can move the knob locking assembly 108 along the direction A and into the position shown with regards to FIG. 11.

After moving the knob locking assembly 108 into the position shown with reference to FIG. 11, a user can remove force from the interface 108, i.e., stop applying force along the direction B. When a user no longer applies force at the interface 1008 along the direction B, the biasing means 904 can cause the actuator to rotate along the direction X about the housing pin 908 such that the tab 1000 can move along the direction B. The tab 1000 can continue moving along the direction B until the tab 1000 contacts a surface 1104 of the drive tube housing 110, as shown with reference to FIG. 11. Furthermore, the second tab surface 1004 of the tab 1000 can abut the flexible drive tube surface 1202. In an embodiment, in the configuration shown with reference to FIG. 11, the knob locking assembly 108 can be locked into the extended position. More specifically, as the user moves the knob locking assembly 108 along the direction A, since the knob locking assembly 108 couples with the end effector 106 via the couplings 300 as previously discussed, the end effector 106 can extend from the end effector assembly 104 into the configuration shown with reference to FIG. 1B. As such, the tab 1000 along with the tab surfaces 1002 and 1004 function to provide a lock for the knob locking assembly 108 such that lock formed by the tab 1000 along and the tab surfaces 1002 and 1004 engage the knob locking assembly 108 with the drive tube housing 110.

Figure 14:
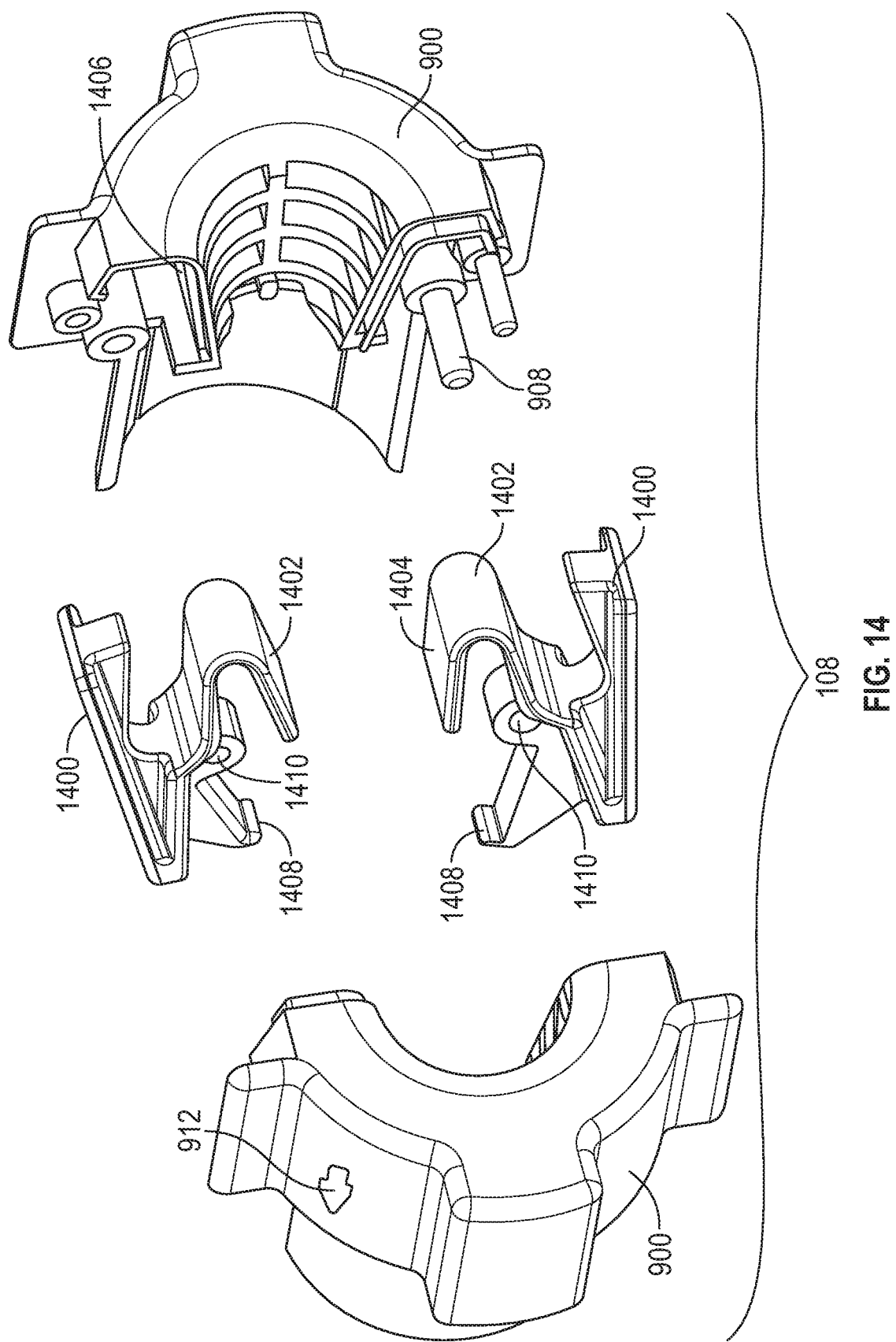
FIG. 14 illustrates a knob locking assembly in accordance with a further example of the present disclosure.

In addition to the configuration shown with reference to FIGS. 9-11 and 13, the knob locking assembly 108 can employ alternative configurations to achieve the retracted and extended positions. To further illustrate, the knob locking assembly 108 can have the configuration shown with reference to FIG. 14 where, in addition to the housing portions 900, the knob locking assembly 108 can include an actuator 1400 having a biasing means 1402. It should be noted that throughout this Specification, reference will be made to an actuator 1400 and actuators 1400. These terms are interchangeable. Thus, disclosure relating to the actuator 1400 is applicable to the actuators 1400 and disclosure relating to the actuators 1400 is applicable to the actuator 1400. In an embodiment, the biasing means 1402 can be integral with the actuator 1400, the tab 1408, the first tab surface 1506, and the second tab surface 1508 such that the actuator 1400, the tab 1408, the first tab surface 1506, and the second tab surface 1508 are unitary with the biasing means 1402. In an embodiment, the biasing means 1402 can have a surface 1404, which, as will be discussed with reference to FIG. 15, can assist the biasing means 1402 with providing a biasing force to the actuators 1400 via a surface 1406 of the housing 900. Moreover, the biasing means 1402 can have a tab 1408 that can have the same functionality as the tab 1000 discussed with reference to FIGS. 9-11 and 13. In an embodiment, the actuators 1400 can be formed of any pliable semi-rigid material. Examples can include any type of polymer, polycarbonate, or the like. Furthermore, in an embodiment, the actuators 1400 can couple with the housing portions 900 via the housing pins 908. In particular, the actuators 1400 can include an actuator bore 1410, which can be configured to accept the housing pin 908 such that the actuators 1400 can couple with the housing portion 900, as shown with reference to FIG. 15.

As noted, the housing surface 1406 assists the biasing means 1402 with providing a biasing force to the actuator 1400. To further illustrate, making reference to FIG. 15, an embodiment of the knob locking assembly 108 is shown where the biasing surface 1404 of the biasing means 1402 abuts the housing surface 1406. In this configuration, since the actuators 1400 can be formed from a pliable material, the housing surface 1406 can bend the biasing means 1402 along the direction Y. To further illustrate, when the knob locking assembly 108 has the configuration shown with reference to FIG. 15, the biasing means 1402 can be compressed such that an arm 1500 of the biasing means 1402 is forced to pivot about an imaginary point 1502 along the direction Y. When the biasing means arm 1500 pivots about the imaginary point 1502. the biasing force can be provided to an end 1504 of the actuator 1400 along the direction C. Thus, the biasing force imparted by the compression of the biasing means arm 1500 can apply a force to the actuator end 1504 along the direction C. Moreover, the force imparted by the biasing means arm 1500 can cause the actuator 1400 to pivot about the housing pin 908 along the direction X such that the actuator 1400 can have the configuration shown with reference to FIG. 15.

The actuator 1400 can include the tab 1408 that can have functionality similar to the tab 1000. Thus, in an embodiment, the tab 1408 can lock the knob locking assembly 108 into the retracted position. In addition, the tab 1408 can lock the knob locking assembly 108 into an extended position. In an embodiment, the tab 1408 can include a first surface 1506 along with a second surface 1508 opposite the first tab surface 1506. In an embodiment, the tab 1408 along with the first tab surface 1506 and the second tab surface 1508 can function as lock that, as will be discussed further on, engages the knob locking assembly 1800 with the drive tube housing 110 in both the retracted and extended positions.

Figure 15:
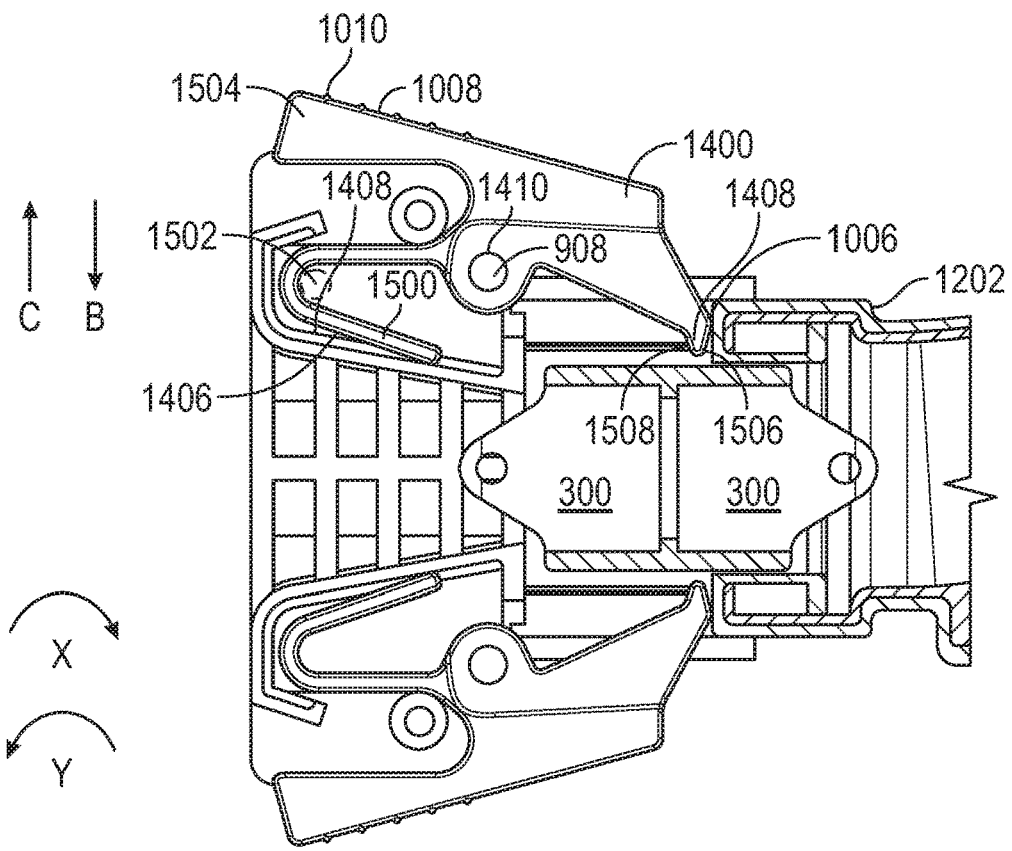
FIG. 15 shows the knob locking assembly of FIG. 14 locked in a retracted position in accordance with a further example of the present disclosure.

In the configuration shown with reference to FIG. 15, the knob locking assembly 108 can be locked in the retracted position. In the retracted position, the first tab surface 1506 can abut against the flexible drive tube surface 1006 such that the flexible drive tube surface 1006 prevents the knob locking assembly 108 from moving along the direction A. Accordingly, the flexible drive tube surface 1006 functions as a stop for the first tab surface 1506. More specifically, in an embodiment, since the first tab surface 1506 abuts the flexible drive tube surface 1006, the first tab surface 1506 in conjunction with the flexible drive tube surface 1006 can prevent movement of the knob locking assembly 108 along the direction A and, in turn, extension of the end effector 106 from the end effector assembly 104 thereby maintaining the knob locking assembly 108 and the end effector 106 in the retracted position.

Figure 16:
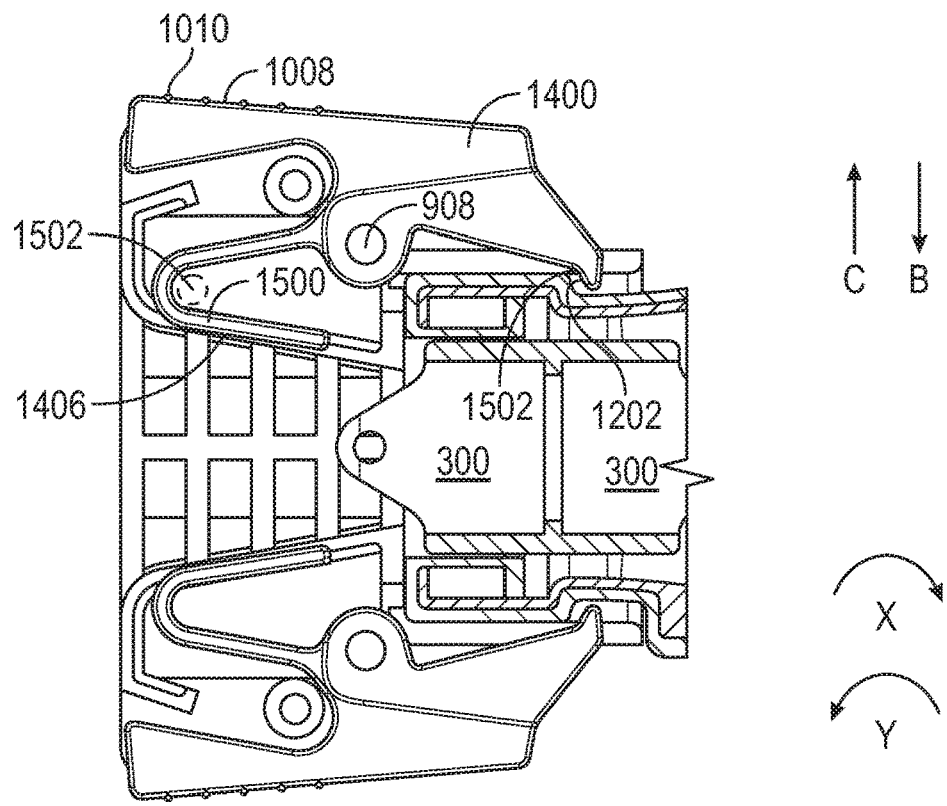
FIG. 16 shows the knob locking assembly of FIG. 14 locked in an extended position in accordance with a further example of the present disclosure.

In an embodiment, if a user desires to move the knob locking assembly 108 from the retracted position shown with reference to FIG. 15 into an extended position, as shown with reference to FIG. 16, a user may apply a force along the direction B at the interface 108 and the ridges 1010. When a user applies a force along the direction B at the interface 108, the actuator 1400 rotates about the housing pin 908 along the direction Y, thereby upwardly moving the tab 1408 along the direction C. In an embodiment, as the tab 1408 moves upwardly along the direction C, the tab 1408 and the first tab surface 1506 can clear the flexible drive tube surface 1006, similar to the tab 1000 and the first tab surface 1002 clearing the flexible drive tube surface 1006, as shown with reference to FIG. 13. Once the tab 1408 and the first tab surface 1506 clear the flexible drive tube surface 1006, the user can move the knob locking assembly 108 along the direction A and into the position shown with reference to FIG. 16, where the user may release the force applied at the interface 108 applied along the direction B.

In the embodiment shown with reference to FIG. 16, the knob locking assembly 108 can be in the extended position. In this position, the second tab surface 1508 can abut the flexible drive tube surface 1202, as shown with reference to FIG. 16. Moreover, in this configuration, since the actuators 1400 can be formed from a pliable material, the housing surface 1406 again can bend the biasing means 1402 along the direction Y. In particular, the biasing means 1402 can be compressed such that the arm 1500 of the biasing means 1402 is forced to pivot about the imaginary point 1502 along the direction Y. When the biasing means arm 1500 pivots about the imaginary point 1502, the biasing force can be provided to the end 1504 of the actuator 1400 along the direction C. Thus, the biasing force imparted by the compression of the biasing means arm 1500 can apply a force to the actuator end 1504 along the direction C. Moreover, the force imparted by the biasing means arm 1500 can cause the actuator 1400 to pivot about the housing pin 908 along the direction X such that the actuator 1400 can have the configuration shown with reference to FIG. 16.

Figure 17:
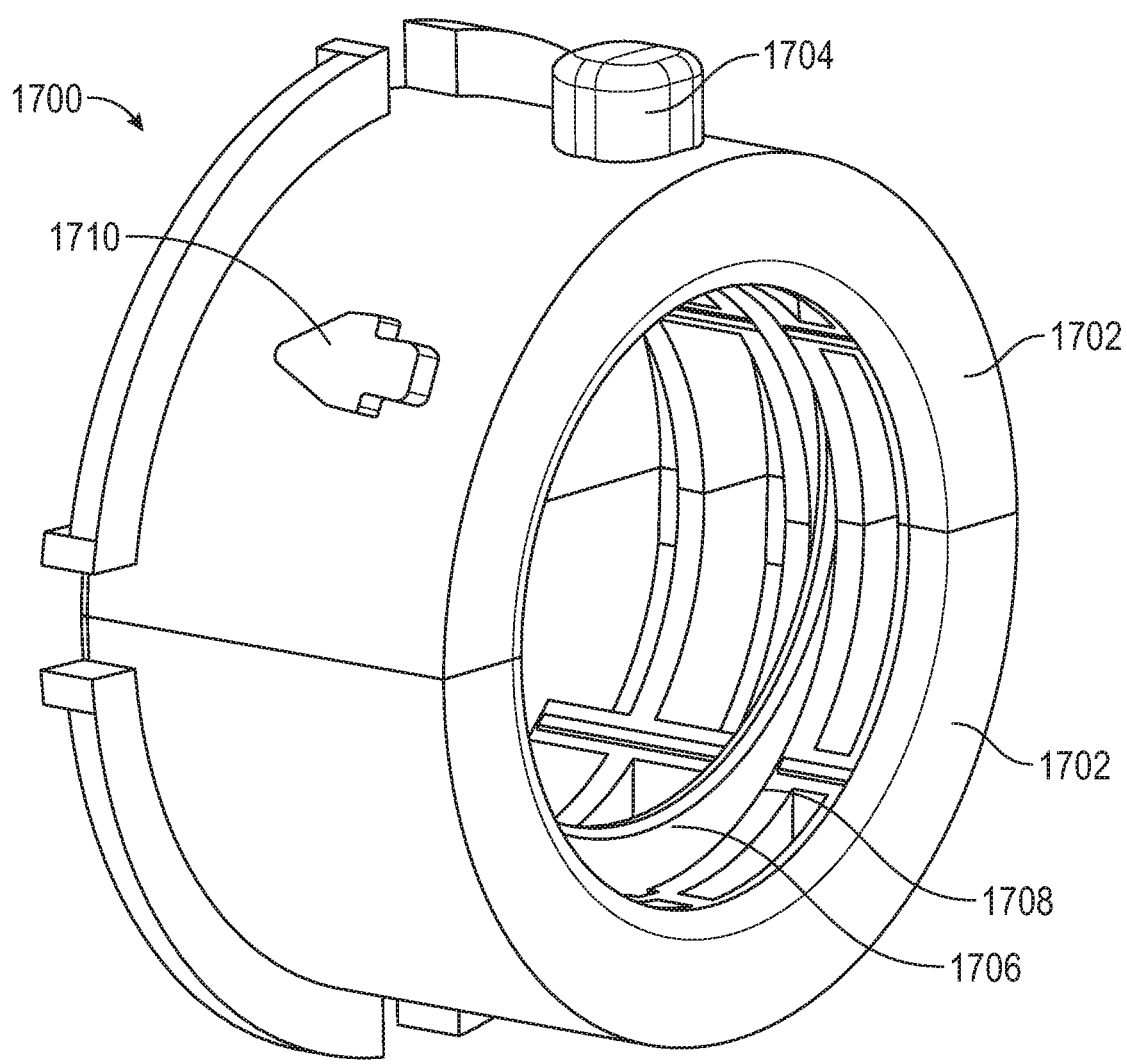
FIGS. 17 and 18 illustrate a knob locking assembly in accordance with another example of the present disclosure.

In addition to the configuration shown with reference to FIGS. 9-11 and 13-16, the colpotomy device 100 can employ knobs having alternative configurations to achieve the retracted and extended positions. For example, the colpotomy device 100 can include a knob locking assembly 1700 that can move the end effector 106 between the retracted position and the extended position, as shown with reference to FIG. 17. In an embodiment, the knob locking assembly 1700 can be positioned at a proximal end of the colpotomy device 100 similar to the knob locking assembly 108. Moreover, the knob locking assembly 1700 can be used to manipulate the end effector assembly 104, such as rotating the end effector assembly 104 in both a clockwise and counterclockwise direction during use of the colpotomy device 100. Moreover, the knob locking assembly 1700 can be used to extend the end effector 106 into the position shown with respect to FIG. 1B and retract the end effector 106 into the position shown with reference to FIG. 1A. The knob locking assembly 1700 can be separated from the end effector assembly 104 via the drive tube housing 110, similar to the knob locking assembly 108 shown with reference to FIGS. 1A and 1B.

Figure 18:
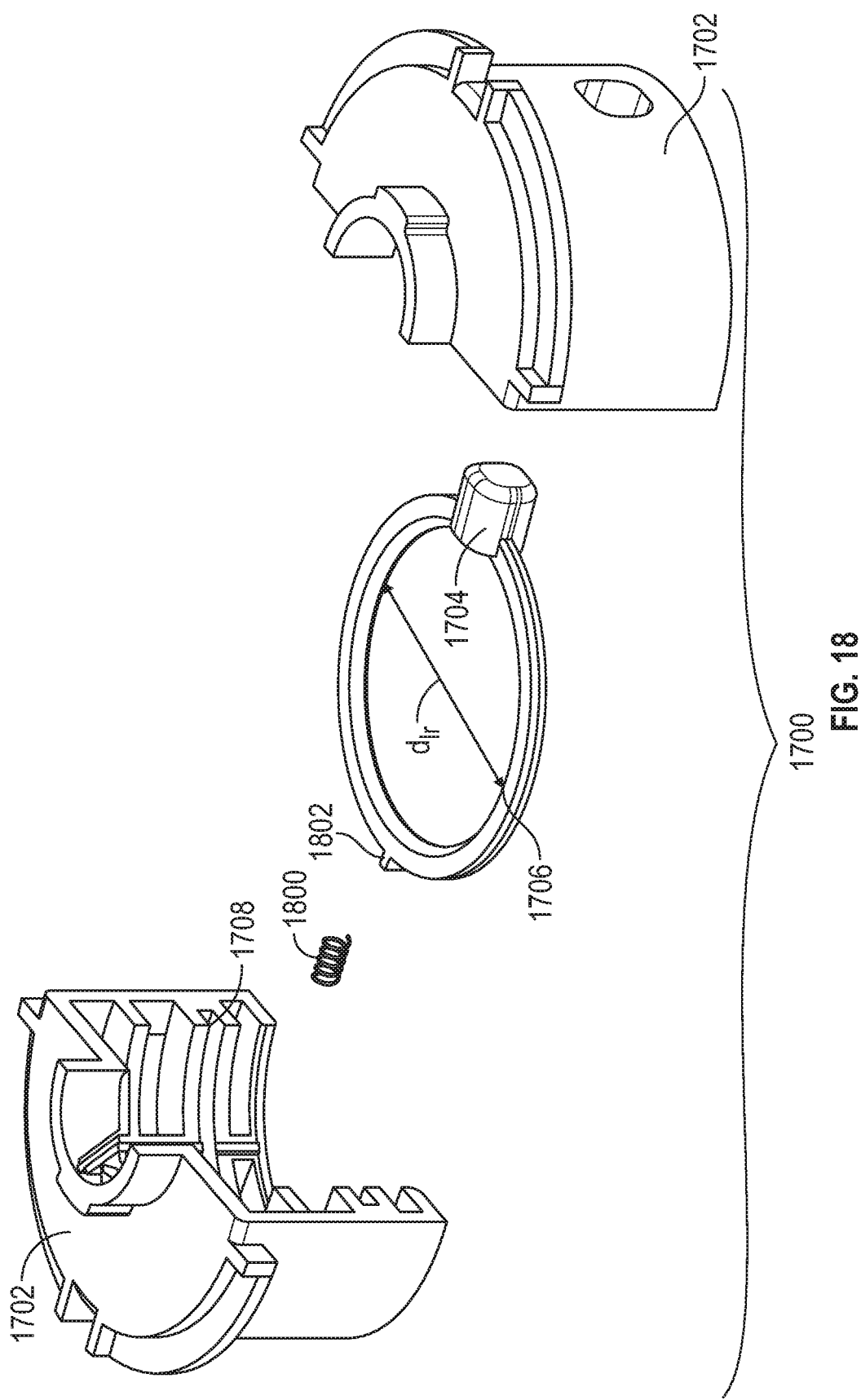

In an embodiment, the knob locking assembly 1700 can include housing portions 1702 along with an actuator 1704 that can be used to lock the knob locking assembly 1700 in either the retracted position or the extended position via a knob ring 1706 disposed within a knob ring seat 1708. Moreover, in an embodiment, the housing portions 1702 can include a directional arrow 1710, which can provide an indication to a user which direction the knob locking assembly 1700 should be moved in order to place the knob locking assembly 1700 in an extended position. The knob ring 1706 can be biased within the housing portions 1702 with a biasing means 1800 that can be situated on a seat 1802, as shown with reference to FIG. 18. In an embodiment, the biasing means 1800 can be a compression spring that, as shown with regards to FIG. 19, can impart a force against the knob ring 1706 along the direction B. In an embodiment, the biasing means 1800 sits in a recess 1900 of the housing portion 1702 and can impart a force against the recess 1900 along the direction C and can impart a force along the direction B against the knob ring 1706 via the seat 1802.

Figure 19:
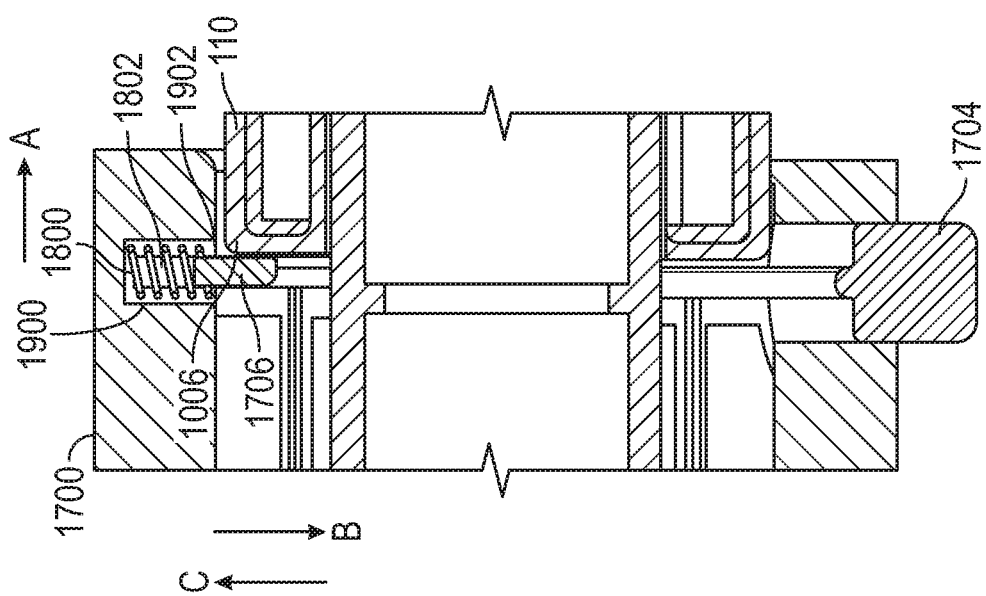
FIG. 19 shows the knob locking assembly of FIGS. 17 and 18 locked in a retracted position in accordance with another example of the present disclosure.
Figure 22:
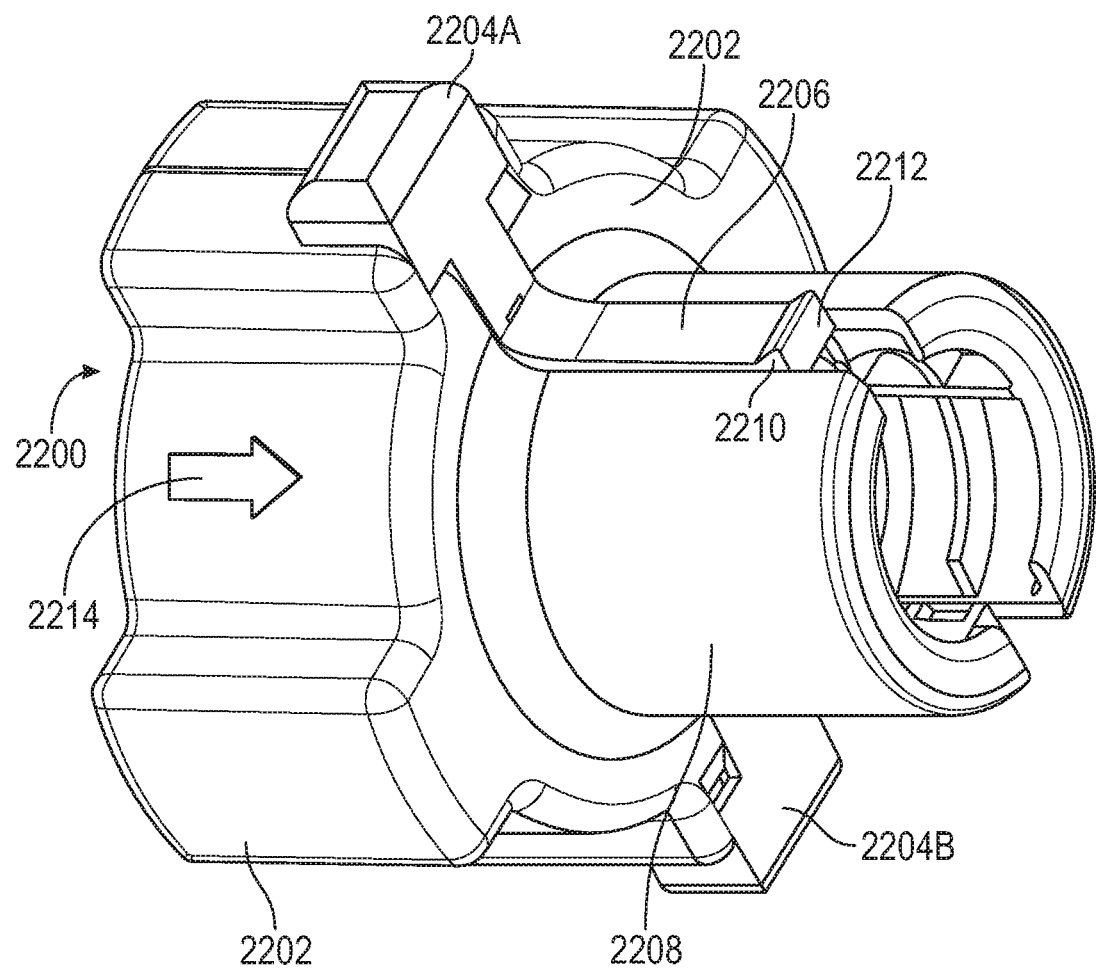
FIG. 22 illustrates a knob locking assembly in accordance with at least one example of the present disclosure.

In the embodiment shown with regards to FIG. 19, the colpotomy device 100 and the knob locking assembly 1700 are in the retracted position. In an embodiment, the knob ring 1706 includes a first surface 1902 that can abut against the flexible drive tube surface 1006 such that the flexible drive tube surface 1006 prevents the knob locking assembly 1700 from moving along the direction A. Therefore, the flexible drive tube surface 1006 can function as a stop for the first surface 1902. More specifically, in an embodiment, since the first surface 1902 abuts the flexible drive tube surface 1006, the first surface 1902 in conjunction with the flexible drive tube surface 1006 can prevent movement of the knob locking assembly 1700 along the direction A and, in turn, extension of the end effector 106 from the end effector assembly 104 thereby maintaining the knob locking assembly 1700 and the end effector 106 in the retracted position.

Figure 20:
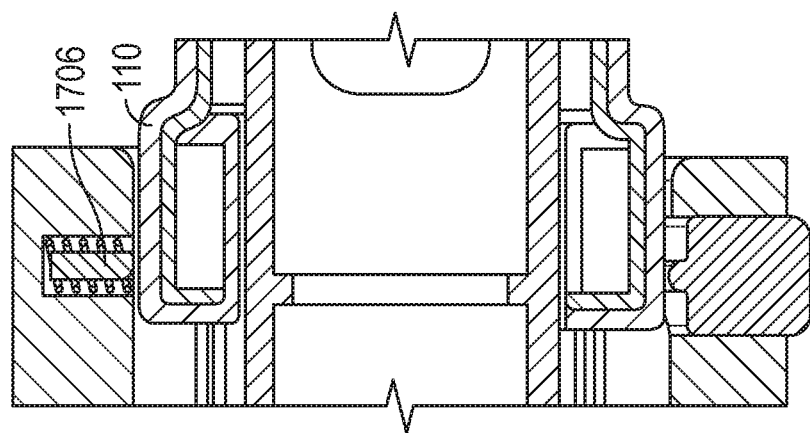
FIG. 20 illustrates the movement of the knob locking assembly of FIGS. 17 and 18 between a retracted position and an extended position in accordance with another example of the present disclosure.

When a user desires to move the knob locking assembly 1700 from the retracted position to the extended position, the user can push the actuator along the direction C, thereby moving the knob ring 1706 and the knob ring seat 1708 along the direction C. As the knob ring 1706 moves along the direction C, the knob ring first surface 1902 clears the flexible drive tube surface 1006 such that the user can move the knob locking assembly 1700 along the direction A, as shown with reference to FIG. 20. As may be seen with reference to FIG. 20, the knob ring 1706 is above the drive tube housing 110 and can move along a top surface of the drive tube housing 110.

Figure 21:
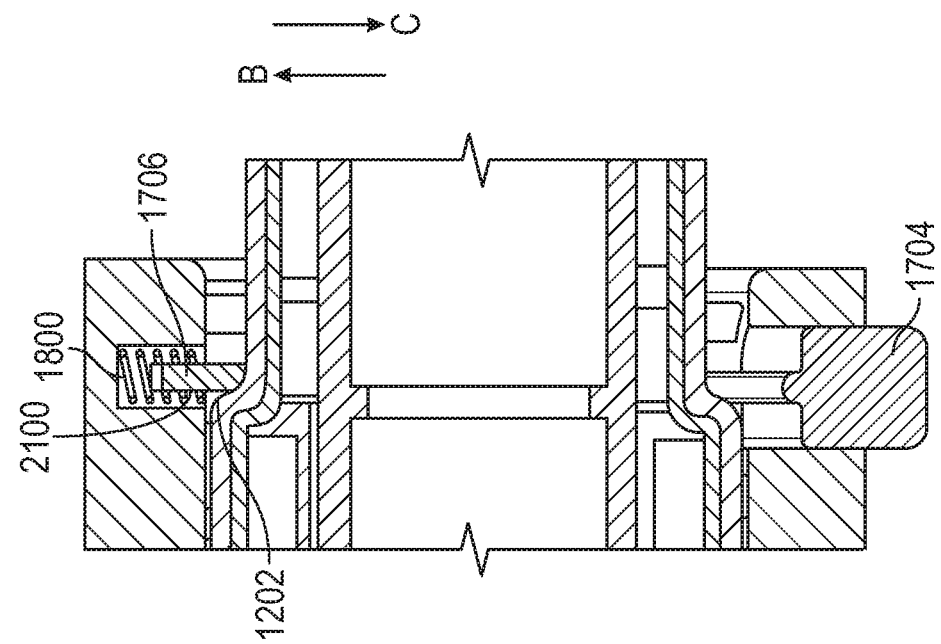
FIG. 21 shows the knob locking assembly of FIGS. 17 and 18 locked in an extended position in accordance with another example of the present disclosure.

A user can move the knob locking assembly 1700 into the position shown with reference to FIG. 21, where the knob locking assembly 1700 is in the extended position. Here, a second surface 2100 of the knob ring 1706 can abut the flexible drive tube surface 1202 of the drive tube housing 110. More specifically, when the knob locking assembly 1700 is moved to the position shown with reference to FIG. 21, a user can release the force on the actuator 1704 such that the biasing means 1800 can move the knob ring 1706 along the direction B. When the knob ring 1706 moves in the direction B, the knob ring second surface 2100 can abut the flexible drive tube surface 1202 such that the knob locking assembly 1700 can be in the extended position. In an embodiment, the actuator 1704 can be a button, a switch, or any other type of tactile mechanism that allows for movement of the knob ring 1706, as discussed above. Furthermore, the biasing means 1800 can be any mechanism capable of imparting a force along the direction B and the direction C. In addition to a compression spring, examples include a wave spring or a leaf spring. In an embodiment, the knob ring 1706 can have an inside diameter $d_{1r}$ in a range of about 0.555 inches to about 1.55 inches and more preferably about 0.80 inches to about 1.05. In particular, the knob ring 1706 can have a diameter that is greater than the diameter $d_1$ of the flexible tube end 1200 such that the knob ring 1706 can slide over the flexible tube end 1200 as discussed with regards to FIG. 20.

In addition to the configuration shown with reference to FIGS. 9-11 and 13-21, the colpotomy device 100 can employ knob locking assemblies having further alternative configurations to achieve the retracted and extended positions, such as the embodiments shown with reference to FIGS. 22-25. To further illustrate, in an embodiment, the colpotomy device 100 can include a knob locking assembly 2200 as shown with reference to FIG. 22 that can move the end effector 106 between the retracted position and the extended position. In an embodiment, the knob locking assembly 2200 can be positioned at a proximal end of the colpotomy device 100 similar to the knob locking assemblies 108 and 1700. The knob locking assembly 2200 can be used to manipulate the end effector assembly 104, such as rotating the end effector assembly 104 in both a clockwise and a counterclockwise direction during use of the colpotomy device 100. The knob locking assembly 2200 can also be used to extend the end effector 106 into the position shown with respect to FIG. 1B and retract the end effector into the position shown with reference to FIG. 1A. The knob locking assembly 2200 can be separated from the end effector assembly 104 via the drive tube housing 110, similar to the knob locking assembly 108 shown with reference to FIGS. 1A and 1B.

The knob locking assembly 2200 can include housing portions 2202 that can have actuators 2204A and 2204B. In an embodiment, the actuators 2204A and 2204B can include a locking mechanism 2206 disposed on a sub-housing 2208 of the housing portion 2202. Furthermore, the locking mechanism 2206 can include a tab 2210 at a distal end thereof that can have a tab surface 2212 which functions to assist with locking the knob locking assembly 2200. It should be noted that throughout this Specification, reference will be made to a tab 2210 and tabs 2210. These terms are interchangeable. Thus, disclosure relating to the tab 2210 is applicable to the tabs 2210 and disclosure relating to the tabs 2210 is applicable to the tab 2210. Similarly, it should be noted that throughout this Specification, reference will be made to a tab surface 2212 and tab surfaces 2212. These terms are interchangeable. Thus, disclosure relating to the tab surface 2212 is applicable to the tab surfaces 2212 and disclosure relating to the tab surfaces 2212 is applicable to the tab surface 2212. Moreover, in an embodiment, the housing portions 2202 can include a directional arrow 2214, which can provide an indication to a user which direction the knob locking assembly 2200 should be moved in order to place the knob locking assembly 2200 in an extended position.

Figure 23:
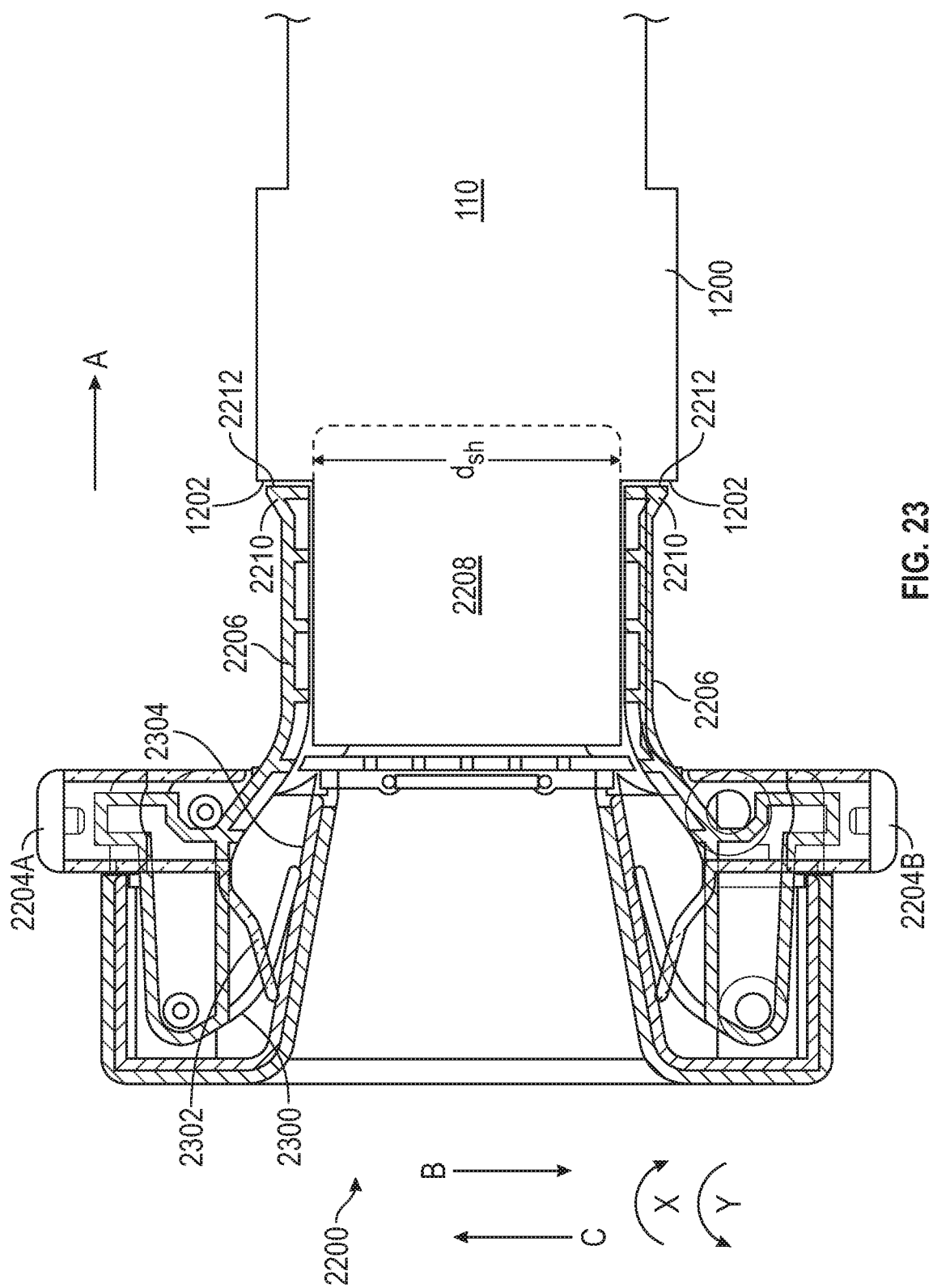
FIG. 23 shows the knob locking assembly of FIG. 22 locked in a retracted position in accordance with at least one example of the present disclosure.
Figure 24:
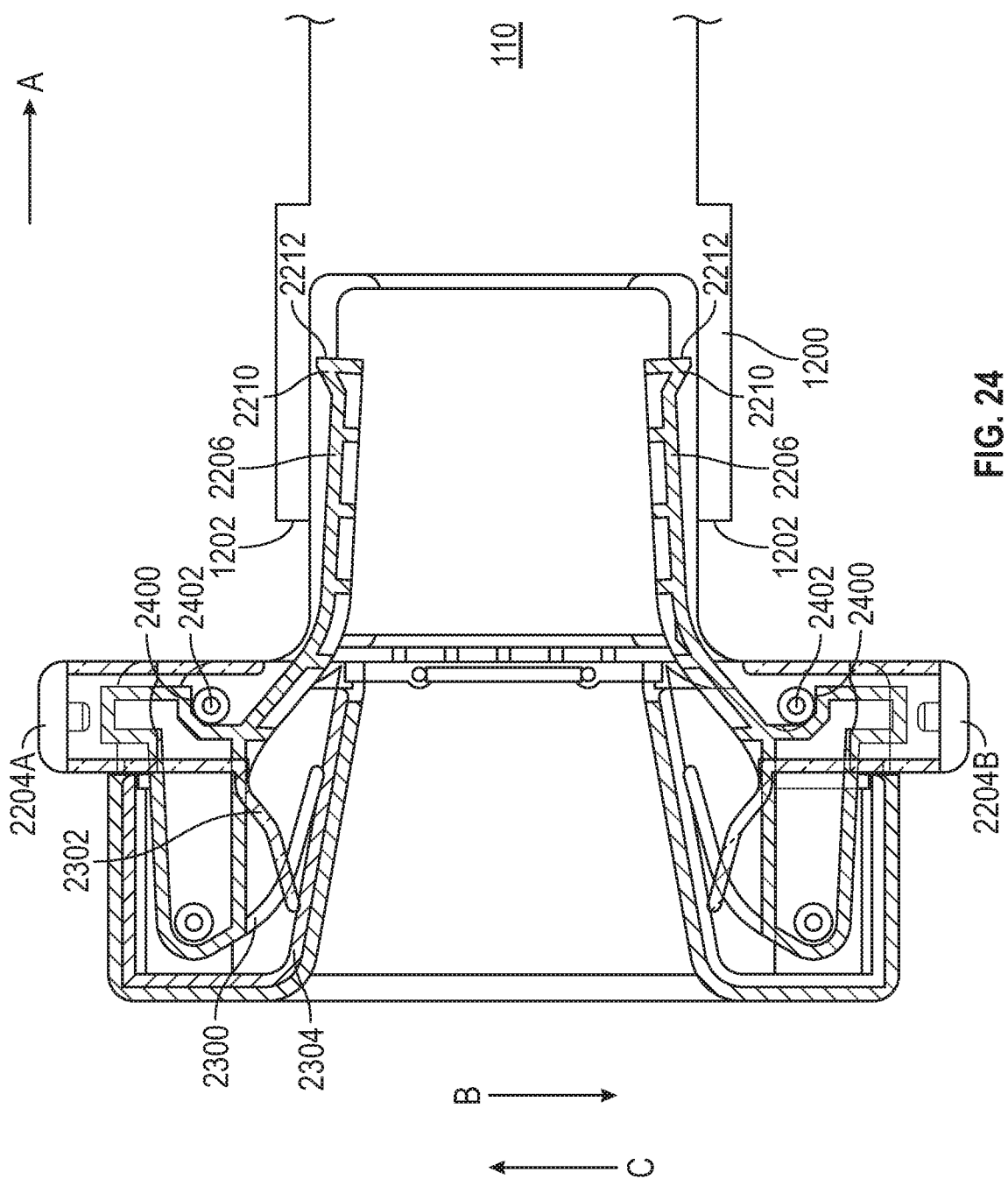
FIG. 24 illustrates the movement of the knob locking assembly of FIG. 22 between a retracted position and an extended position in accordance with at least one example of the present disclosure.
Figure 25:
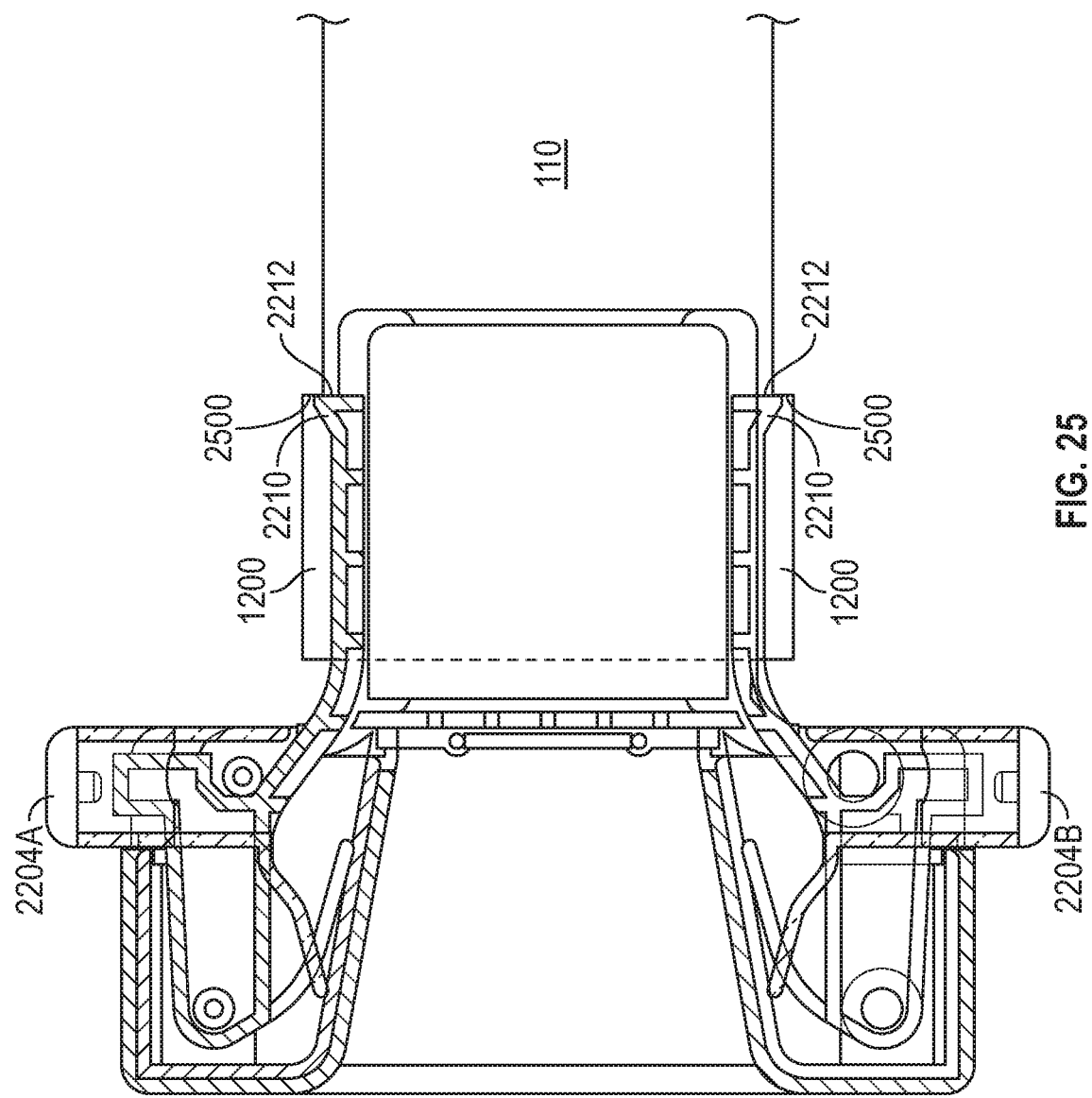
FIG. 25 shows the knob locking assembly of FIG. 22 locked in an extended position in accordance with at least one example of the present disclosure.

Now making reference to FIG. 23, a first portion of the sub-housing 2208 is disposed within the flexible tube end 1200 while the remainder of the sub-housing 2208 can be external of the flexible tube end 1200. Here, the sub-housing 2208 can have a circular configuration and can be configured to fit inside the flexible tube end 1200. It should be noted that the sub-housing 2208 can have other configurations which can be complimentary to a configuration of the flexible tube end 1200. For example, if the flexible tube end 1200 has a square configuration, the sub-housing 2208 can have a square configuration that complements the square configuration of the flexible tube end 1200. In an embodiment, the sub-housing 2208 can have a diameter $d_{sh}$ in a range of about 0.45 inches to about 1.45 inches and more preferably about 0.70 inches to about 0.95 inches. In particular, the sub-housing 2208 can have a diameter $d_{sh}$ that is less than the diameter $d_1$ of the flexible tube end 1200 such that the sub-housing 2208 can fit within the flexible tube end 1200.

In the embodiment shown with regards to FIG. 23, the knob locking mechanism is in the retracted position. In particular, as may be seen with reference to FIG. 23, the tab surface 2212 abuts the flexible drive tube surface 1202. Accordingly, the flexible drive tube surface 1006 functions as a stop for the tab surface. More specifically, in an embodiment, since the tab surface 2212 abuts the flexible drive tube surface 1006, the tab surface 2212 can prevent movement of the knob locking assembly 2202 along the direction A and, in turn, extension of the end effector 106 from the end effector assembly 104 thereby maintaining the knob locking assembly and the end effector 106 in the retracted position.

In an embodiment, each of the actuators 2204A and 2204B can include a rotation pin 2300 and biasing means 2302 that can function to maintain the tab 2210 in the position shown with reference to FIG. 23. Each of the rotation pin 2300 and the biasing means 2302 can abut a surface 2304 of the housing portion 2202. In an embodiment, the rotation pin 2300 and the biasing means 2302 can bias the tab 2210 into the position shown with reference to FIG. 23 such that the tab surface 2212 abuts the flexible drive tube surface 1202. In an embodiment, the actuators 2204A and 2204B can be formed of any pliable semi-rigid material. Examples can include any type of polymer, polycarbonate, or the like. Likewise, the rotation pin 2300 and the biasing means 2302 can also be formed from a pliable semi-rigid material similar to the actuator 2204A and 2204B. Due to the semi-rigidity of the rotation pin 2300 and the biasing means 2302, when the biasing means 2300 and 2302 are disposed on the housing surface 2304 as shown with reference to FIG. 23, each of the rotation pin 2300 and the biasing means 2302 can impart a force along the direction B against the housing surface 2304 such that the housing surface 2304 can impart an opposing force along the direction C. As a result of the housing surface 2304 imparting the opposing force along the direction C, the tab 2210 can stay in the position shown with reference to FIG. 23 such that the knob locking assembly 2200 can stay in the retracted position and the end effector 106 can stay in the retracted position.

A user can employ the knob locking assembly 2200 to move the end effector 106 between the retracted position shown with reference to FIG. 1A and the extended position shown with reference to FIG. 1B. In particular, making reference to FIG. 24, a user can impart a force on the actuator 2204A along the direction B and impart a force on the actuator 2204B along the direction C, thereby moving the actuators 2204A and 2204B into the housing portions 2202. In an embodiment, the user can move the actuators 2204A and 2204B until a surface 2400 of the actuator comes into contact with an actuator stop 2402. As the actuators 2204A and 2204B are moved, a user can move the knob lock assembly along the direction A and the tab 2210 along with the tab surface 2212 can clear the flexible drive tube surface 1202. In particular, a user can move the actuators 2204A and 2204B such that the tabs 2210 move inside of the sub-housing 2208, as shown with respect to FIG. 24. Thus, a user can move the locking mechanism 2206, the tab 2210, and the tab surface 2212 inside the flexible tube end 1200 along the direction A. Furthermore, once inside the flexible tube end 1200, a user can release the actuators 2204A and 2204B and can continue moving the knob locking assembly 2200 until the tab surface 2212 abuts a flexible drive tube surface 2500, as shown with reference to FIG. 25. In an embodiment, in FIG. 25, the knob locking assembly 2200 is in the extended position such that the end effector 106 extends from the end effector assembly as shown with reference to FIG. 1B. As detailed above, the tab 2210 along with the tab surface 2212 are configured to engage the knob locking assembly 2200 such that the knob locking assembly engages with the drive tube housing 110 in both the retracted position and the extended position.

Figure 26B:
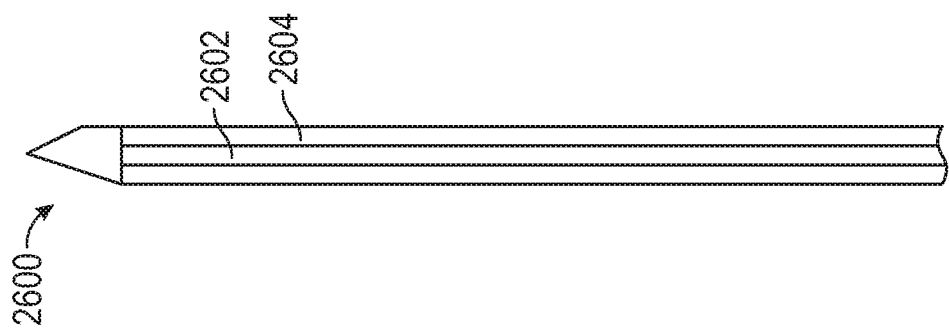
FIGS. 26A-26C illustrate a cutting device in accordance with at least one example of the present disclosure.
Figure 26A:
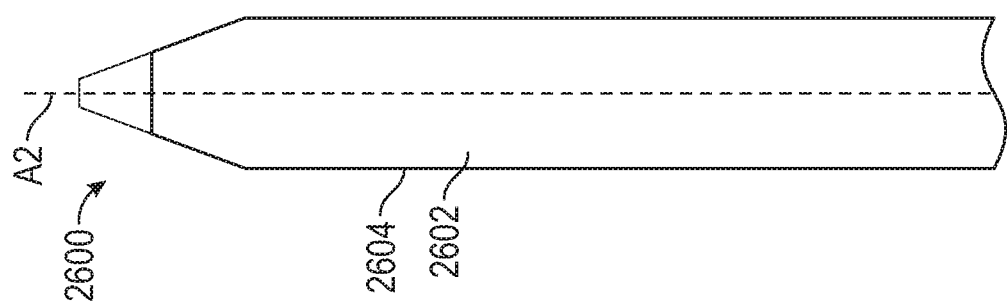
Figure 26C:
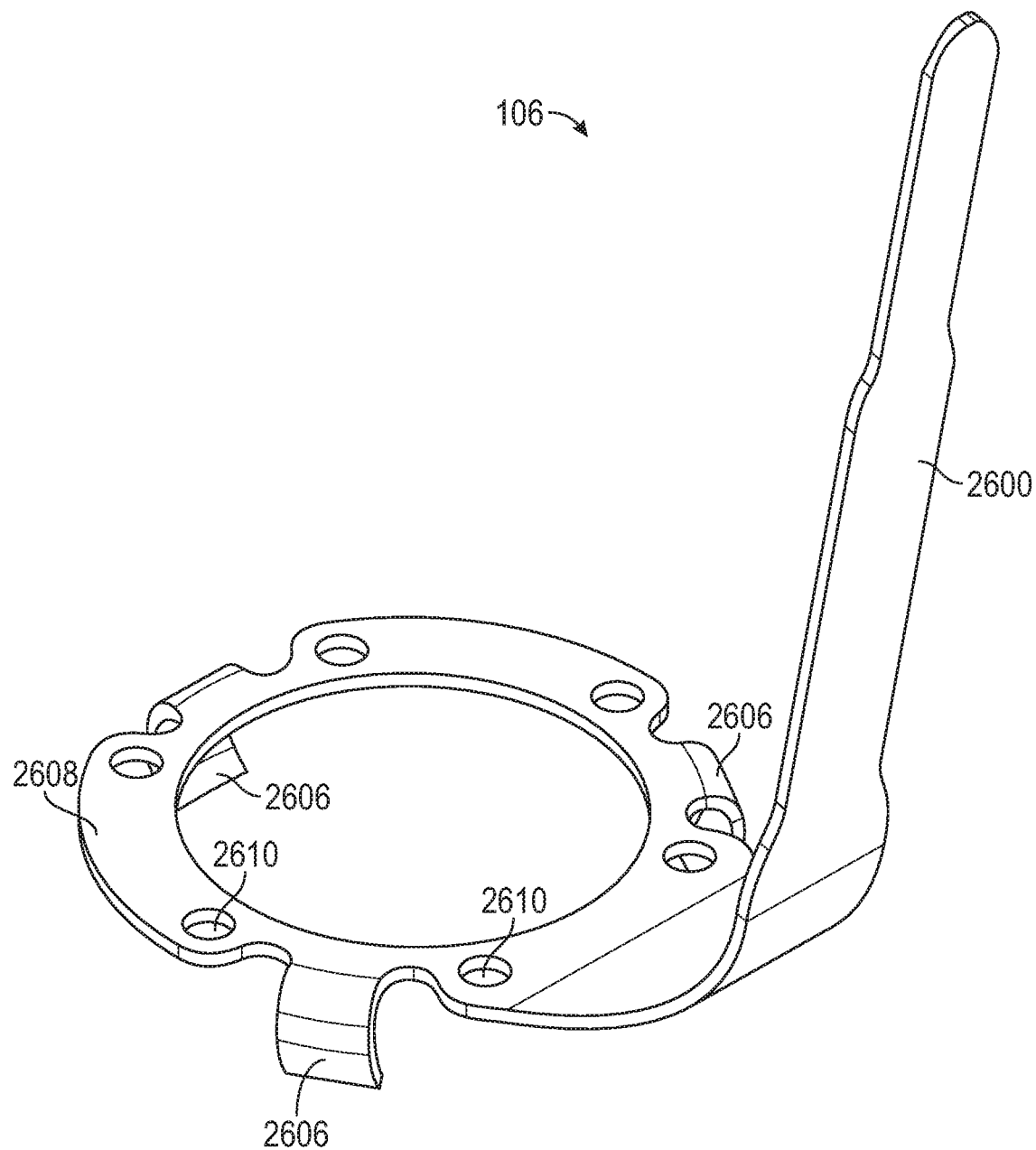

As noted above, the knob locking assemblies 108, 1700, and 2200 function to facilitate movement of the end effector 106 between a retracted position and an extended position. In the extended position, the end effector 106 can be used for resection of the uterus 208, as discussed above. An example of the end effector 106 will now be discussed with reference to FIGS. 26A-26C. FIG. 26A is schematic illustration of a planar view of a cutting device 2600 that can be used with the end effector 106. FIG. 26B is schematic illustration of a side view of the cutting device 2600 of FIG. 26A, FIG. 26C is a perspective view of the cutting device of FIGS. 26A and 26B.

As shown in FIG. 26A, the cutting device 2600 can include a central portion 2602 and a peripheral portion 2604. In an embodiment, the cutting device central portion 2602 can be insulative and at least partially surrounded by the cutting device peripheral portion 2604. In an embodiment, the cutting device peripheral portion 2604 can be conductive. The cutting device central portion 2602 can be electrically-insulative in order to block or limit the flow of electrical current therethrough. The cutting device peripheral portion 2604 can be electrically-conductive to permit the flow of electrical current therethrough. In an embodiment, by limiting current flow through the cutting device central portion 2602, a majority of current can travel through the cutting device peripheral portion 2604 in order to focus energy that can be delivered for resection. Therefore, this configuration can allow for more precise cutting. It should be noted that while the cutting device 2600 is described as being bipolar, in a further embodiment, the cutting device 2600 can be monopolar. Furthermore, in an embodiment, in order to facilitate electrical contact with a current source, the cutting device 2600 can include contacts 2606 along with an interface 2608 having cutting device bores 2610. The cutting device interface 2608 and the cutting device bores 2610 can allow for coupling the cutting device 2600 to the colpotomy device 100, as shown with reference to FIG. 27.

Figure 27:
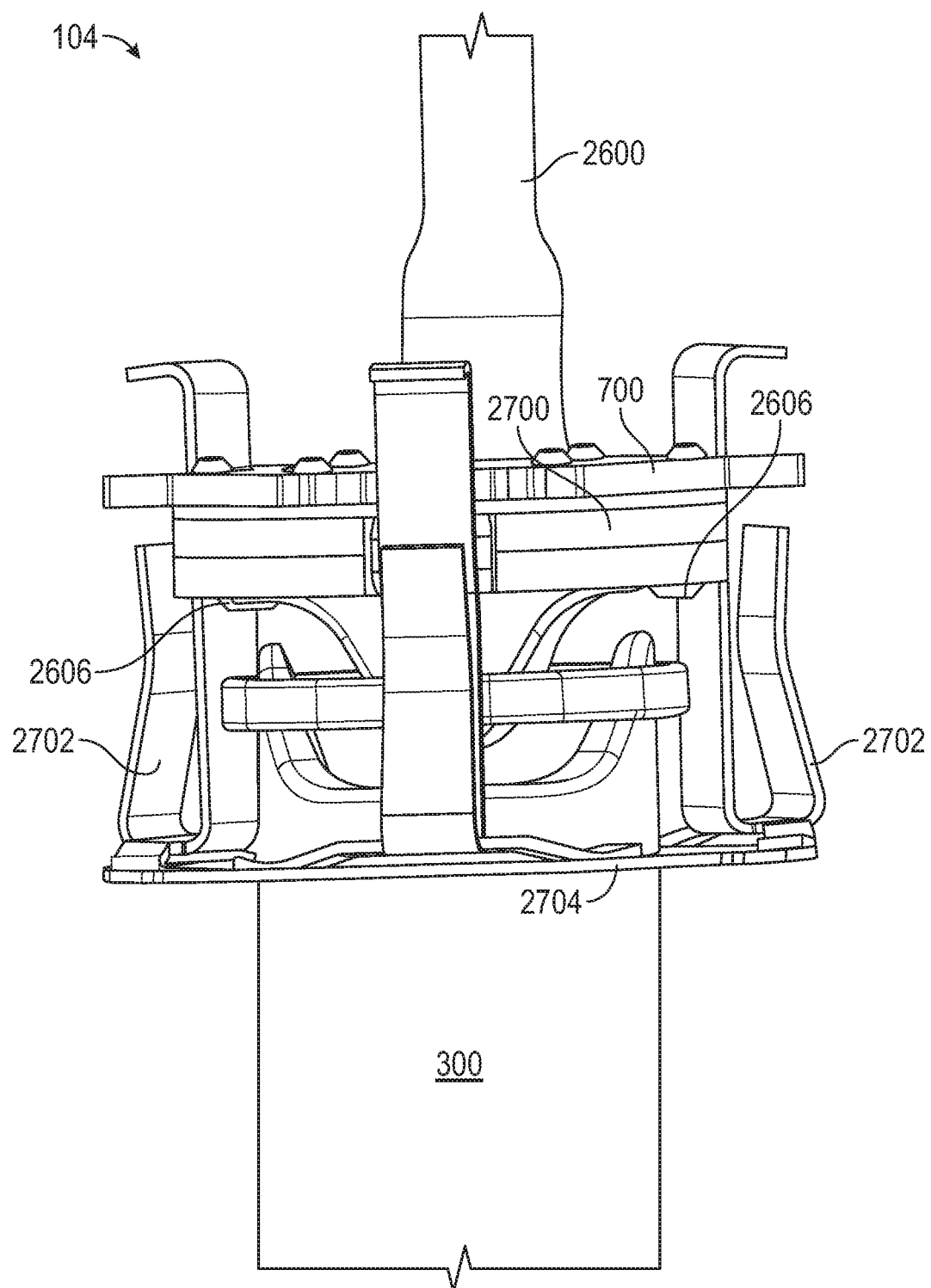
FIG. 27 shows the end effector assembly of FIGS. 1A and 1B in accordance with at least one example of the present disclosure.
Figure 28:
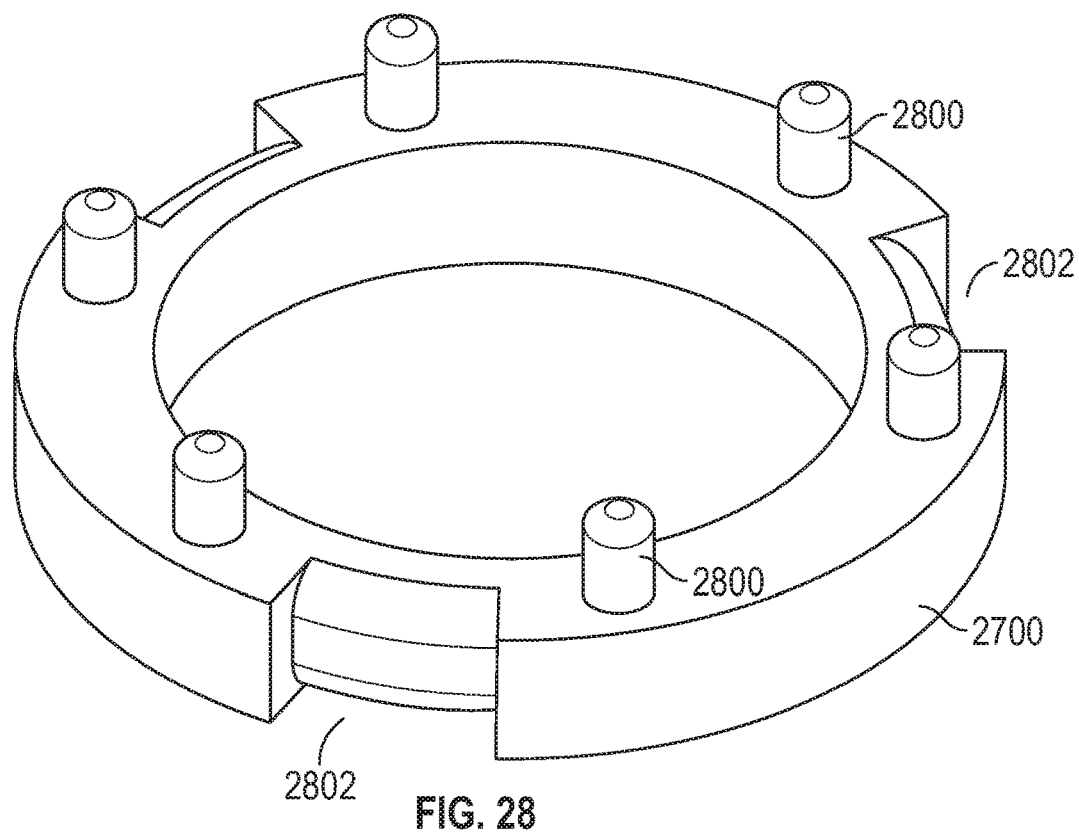
FIG. 28 illustrates a blade cover in accordance with at least one example of the present disclosure.
Figure 29:
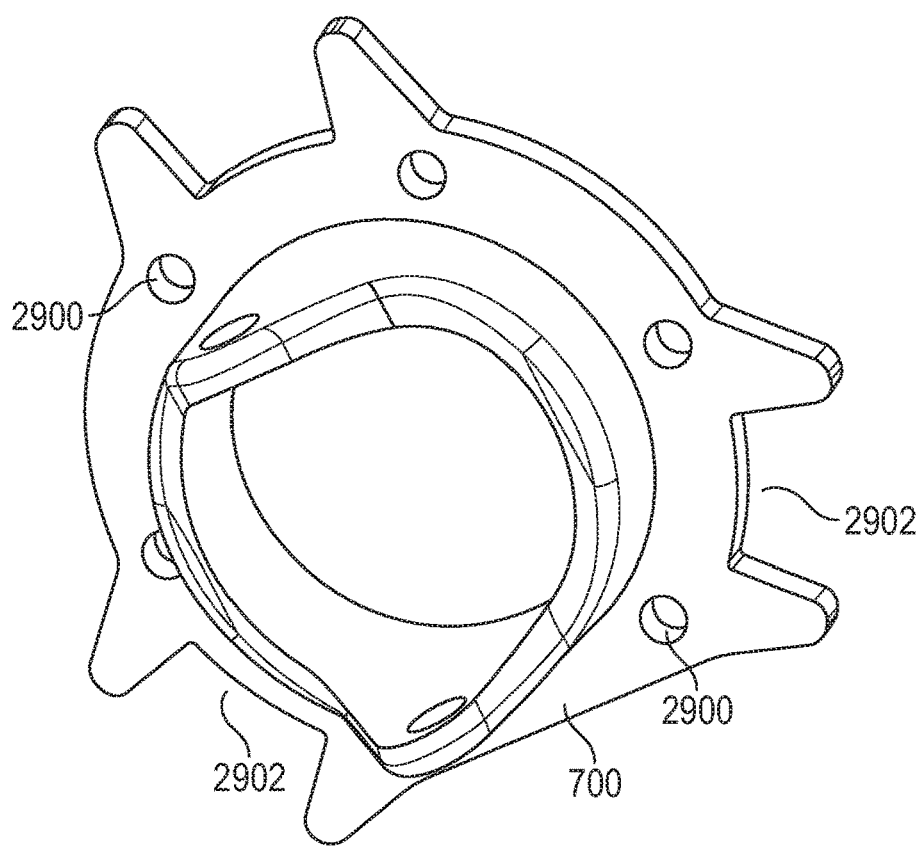
FIG. 29 illustrates an end effector assembly coupling in accordance with at least one example of the present disclosure.
Figure 30:
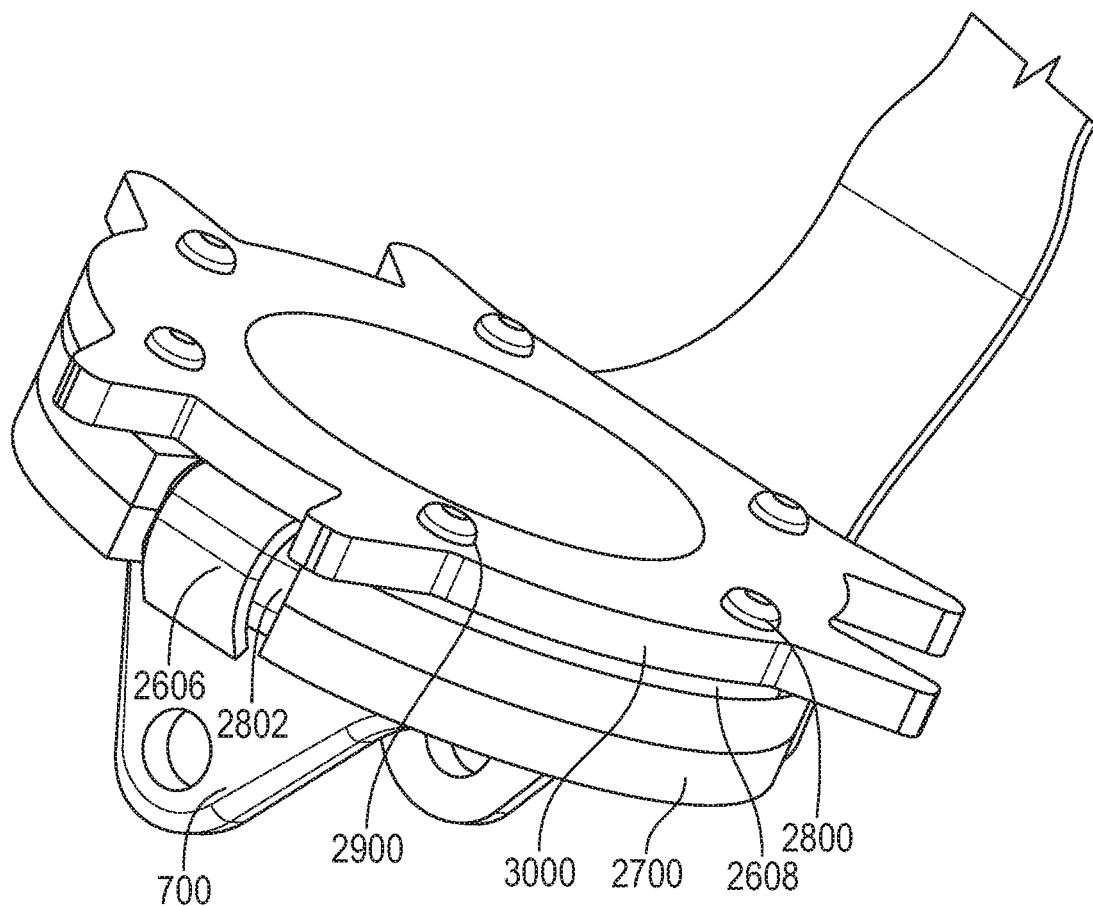
FIG. 30 shows the cutting device of FIGS. 26A-26C disposed between the blade cover of FIG. 28 and the end effector assembly coupling of FIG. 29, in accordance with at least one example of the present disclosure.

FIG. 27 illustrates a perspective view of the end effector assembly 104 in accordance with an embodiment of the present disclosure. As previously discussed, the end effector assembly 104 can couple with the coupling 300 and the colpotomy device 100 via the end effector assembly coupling 700 such that the cutting device 2600 can couple with the colpotomy device 100. In an embodiment, the end effector assembly 104 can include a blade cover 2700 that can couple with the end effector assembly coupling 700 and the cutting device 2600. In particular, the blade cover 2700 can include bosses 2800 (FIG. 28) where the cutting device bores 2610 and end effector assembly coupling bores 2900 (FIG. 29) are configured to receive the blade cover bosses 2800, as shown with reference to FIG. 30. In an embodiment, the cutting device 2600 can be disposed between the blade cover 2700 and a flange 3000 of the end effector assembly coupling 700, also as shown with reference to FIG. 30. Therefore, the cutting device 2600 can couple with the colpotomy device 100 via the blade cover 2700 and the end effector assembly 700. As discussed above, the end effector 106 can rotate with the knob locking assemblies 108, 1700, and 2200. In an embodiment, the end effector assembly 700 can couple the cutting device 2600 with the knob locking assemblies 108, 1700, and 2200 such that when the cutting device 2600 is used with the end effector 106, the cutting device 2600 can rotate with the knob locking assemblies 108, 1700, and 2200 via the end effector assembly 700.

Figure 31:
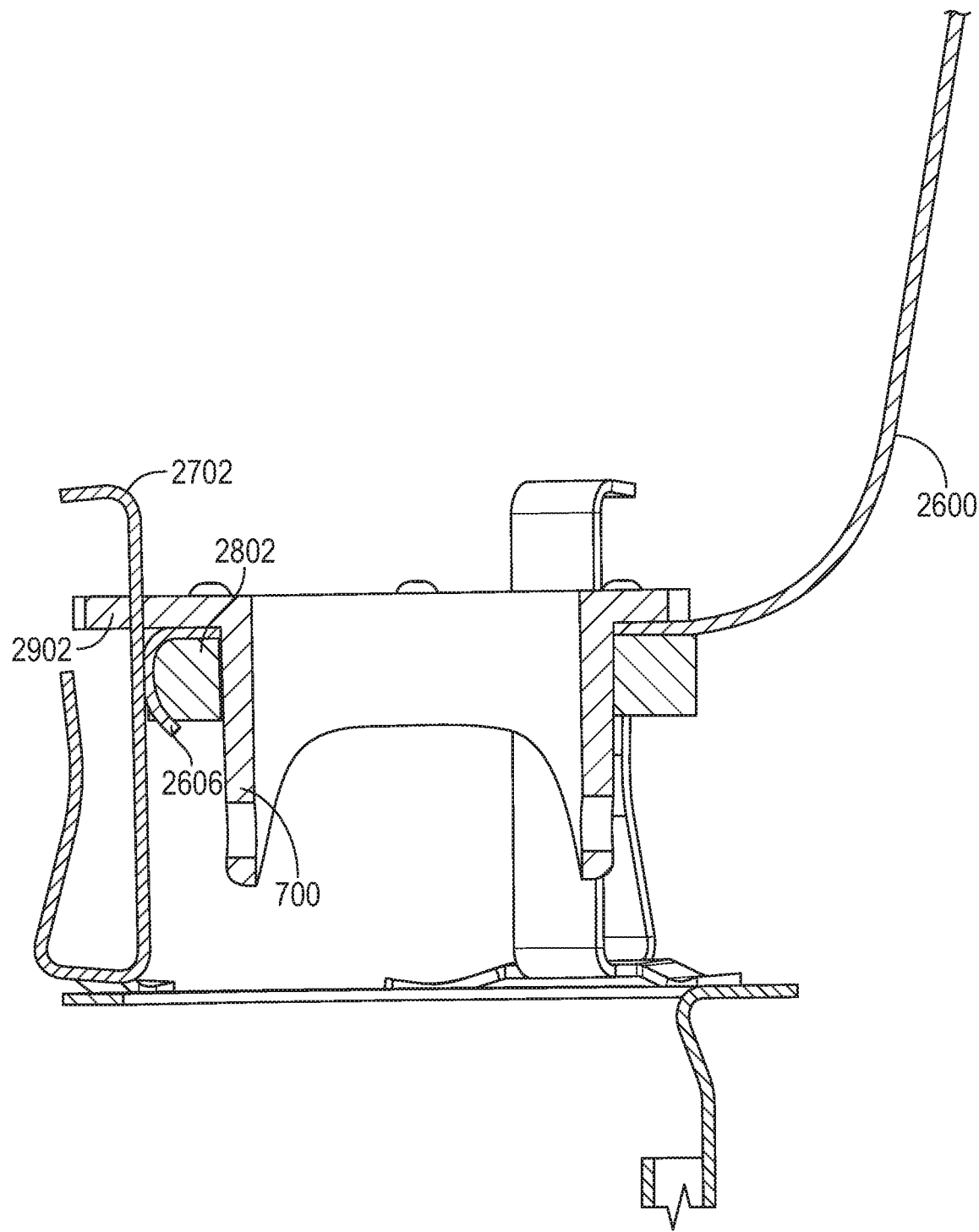
FIGS. 31 and 32 illustrate the cutting device in FIG. 30 contacting an axial contact and a circumferential electrical contact, in accordance with at least one example of the present disclosure.
Figure 32:
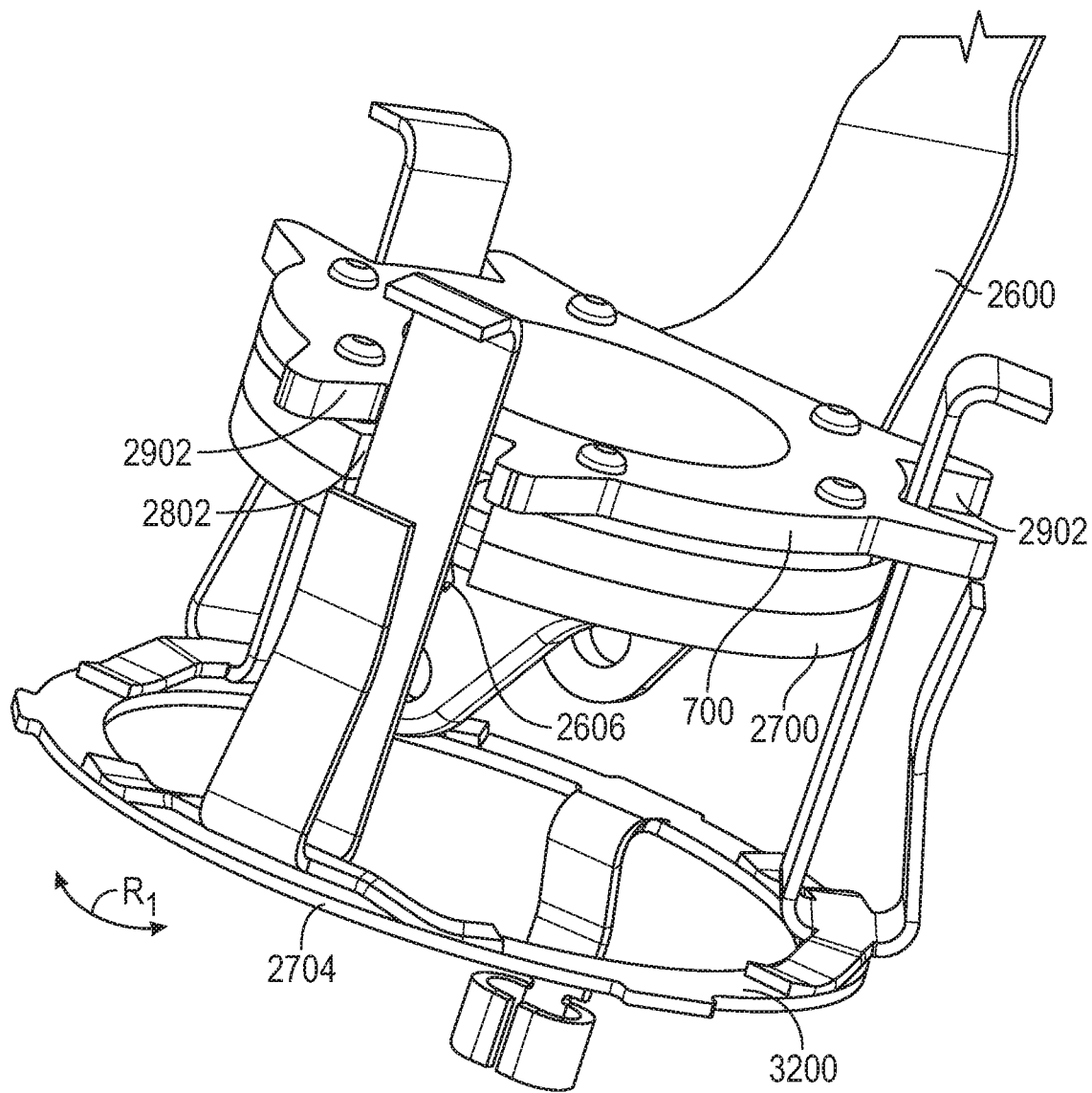

As mentioned above, in some embodiments, the cutting device 2600 can include the cutting device peripheral portion 2604, through which electrical current can travel during a resection procedure. In order to provide current to the cutting device 2600 and the cutting device peripheral portion 2604, the colpotomy device 100 can include an axial contact 2702 electrically coupled with a circumferential electrical contact 2704, as shown with reference to FIG. 27. In an embodiment, the axial contact 2702 can be electrically coupled to the cutting device contact 2606 such that current from the circumferential electrical contact 2704 can travel to the cutting device 2600 via the axial contact 2702. In an embodiment, the axial contact 2702 can couple with the end effector assembly 104 via the end effector assembly coupling 700 and the blade cover 2700. More specifically, the end effector assembly coupling 700 can include recesses 2902 that are configured to hold the axial contact 2702, as shown with reference to FIGS. 29, 31, and 32. Moreover, the blade cover 2700 can include recesses 2802 that are configured to hold the axial contact 2702, as shown with reference to FIGS. 28, 30, and 31.

Furthermore, as noted above, the cutting device contacts 2606 contact the axial contact 2702 in order to provide current to the cutting device 2600. In an embodiment, the blade cover recesses 2802 can be configured to hold the cutting device contacts 2606 along with the axial contacts 2702 such that the axial contacts 2702 can contact the cutting device contacts 2606, as shown with reference to FIGS. 30 and 31. Thus, when the end effector assembly 700 and the cutting device 2600 rotate with the knob locking assemblies 108, 1700, and 2200, the axial contacts 2702 can also rotate while current continues to travel to the cutting device 2600.

As the axial contacts 2702 rotate during rotation of the end effector assembly 700 and the cutting device 2600, the axial contact 2702 should stay in contact with the circumferential contact 2704. Therefore, in an embodiment, the circumferential electrical contact 2704 can include a surface 3200 upon which the axial contact 2702 can contact, as shown with reference to FIG. 32. In an embodiment, the end effector assembly 700, the cutting device 2600, and the blade cover 2700 rotate with the knob locking assemblies

108, 1700, and 2200 along a direction $R_1$, the axial contact 2702 slides along the circumferential contact surface 3200 such that the axial contact 2702 can remain in electrical contact with the circumferential contact 2704. As such, current can be continually provided to the cutting device 2600 and the cutting device peripheral portion 2604 during rotation of the knob locking assemblies 108, 1700, and 2200.

Figure 33:
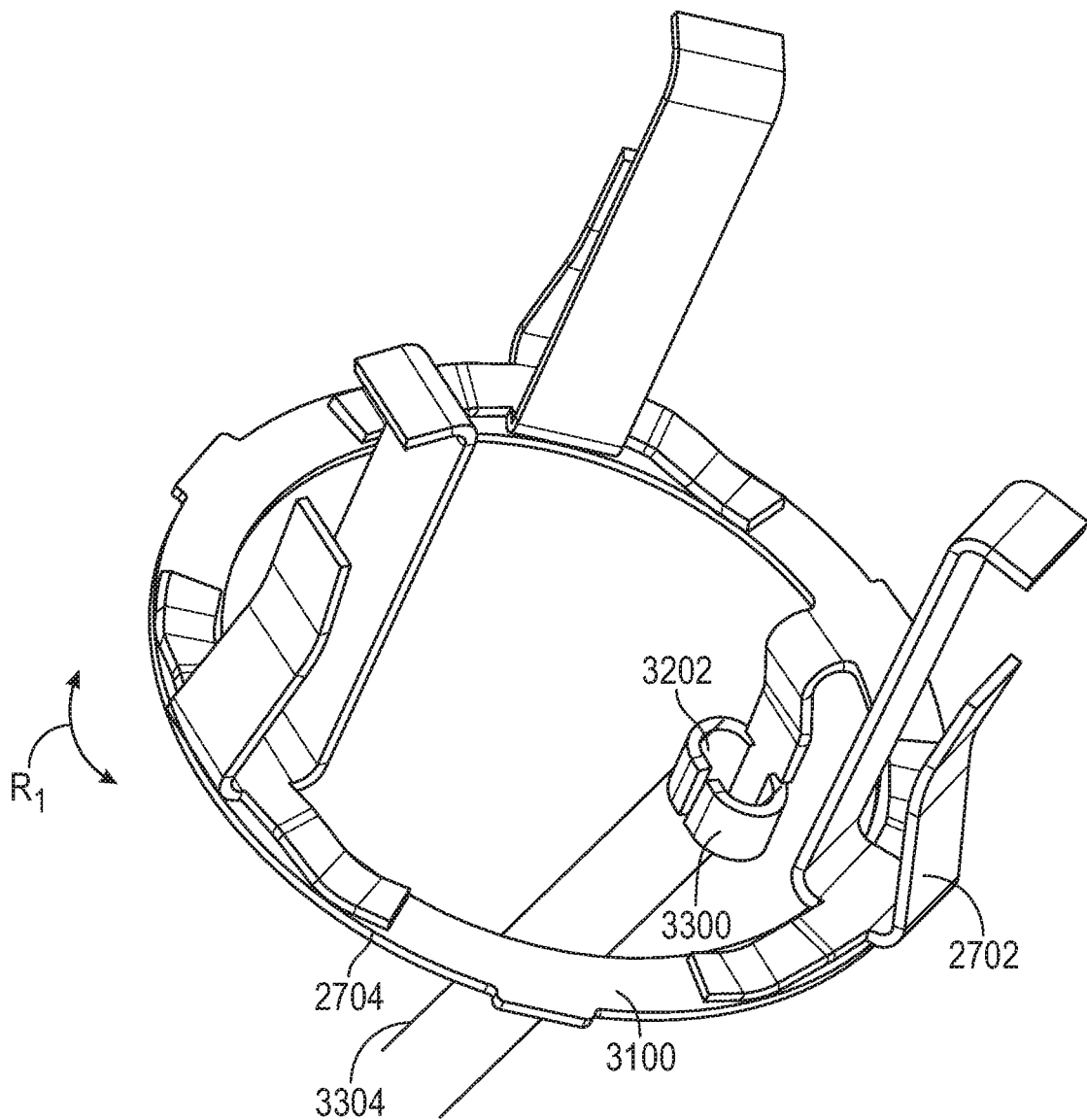
FIG. 33 is a perspective view of the axial and the circumferential electrical contact shown with reference to FIGS. 31 and 32, in accordance with at least one example of the present disclosure.

As noted above, the circumferential contact 2704 provides current to the cutting device 2600 via the axial contact 2702. In an embodiment, in order to provide current, the circumferential contact 2704 can include an interface 3300 that can form a recess 3302 within which an electrical source 3304, such as a wire carrying an electrical current, can be disposed, as shown with respect to FIG. 33. In an embodiment, the electrical source 3304 can provide current to the circumferential contact 2704.

As noted above, a user can rotate the end effector assembly 104 and the end effector 106 during a resection procedure, such as resection of the uterus 208. Furthermore, as noted above, the cutting device 2600 can include the cutting device peripheral portion 2604, which allows for the flow of current therethrough in order to provide more precise cutting. In order to continually provide current to the cutting device 2600 during a resection procedure, the axial contact 2702 can be configured to rotate along the circumferential contact surface 3200 while a user rotates the cutting device 2600.

Figure 34A:
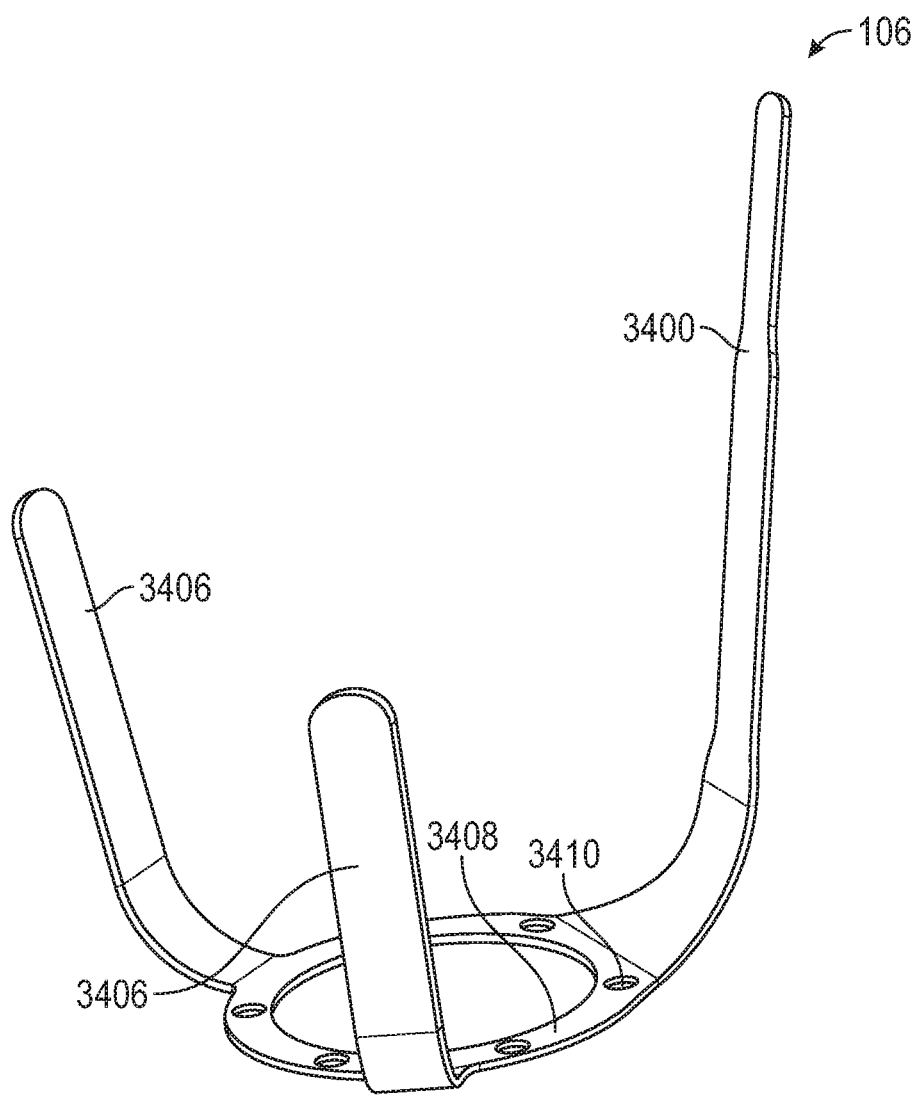
FIGS. 34A-C show a cutting device in accordance with an alternative embodiment of the present disclosure.
Figure 34C:
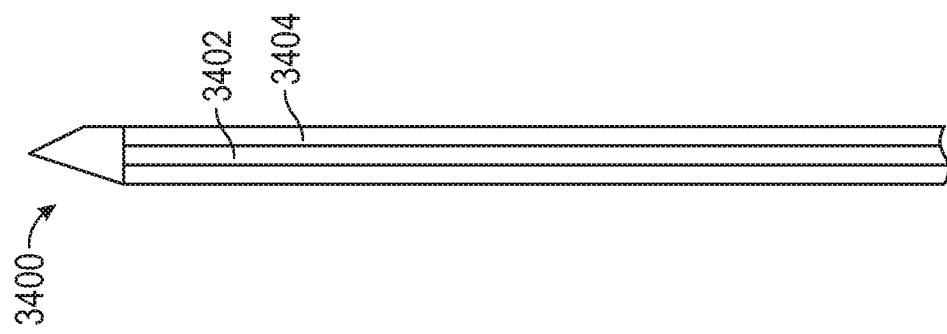
Figure 34B:
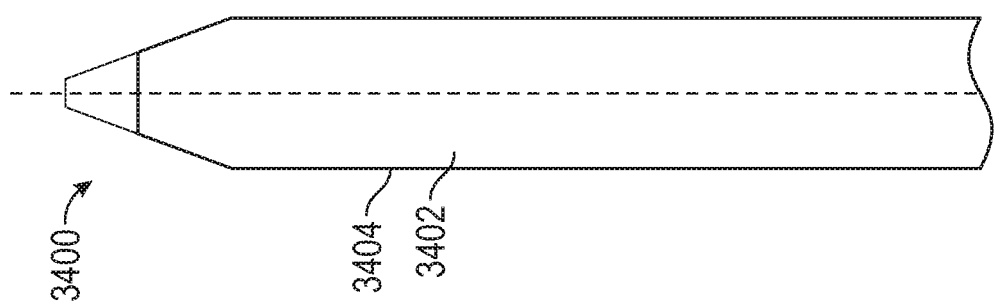

In an alternative embodiment, the end effector 106 can include a cutting device 3400 as shown with regards to FIG. 34A. In this embodiment, the cutting device 3400 can include the configuration of the cutting device 2600, such as a cutting device central portion along with a cutting device peripheral portion. As shown in FIG. 34B, the cutting device 3400 can include a central portion 3402 and a peripheral portion 3404. In an embodiment, the cutting device central portion 3402 can be insulative and at least partially surrounded by the cutting device peripheral portion 3404. In an embodiment, the cutting device peripheral portion 3404 can be conductive. The cutting device central portion 3402 can be electrically-insulative in order to block or limit the flow of electrical current therethrough. The cutting device peripheral portion 3404 can be electrically-conductive to permit the flow of electrical current therethrough. In an embodiment, by limiting current flow through the cutting device central portion 3402, a majority of current can travel through the cutting device peripheral portion 3404. It should be noted that while the cutting device 3400 is described as being bipolar, in a further embodiment, the cutting device 3400 can be monopolar.

In an embodiment, in order to facilitate electrical contact with a current source, the cutting device 3400 can include contacts 3406 along with an interface 3408 having cutting device bores 3410. The cutting device interface 3408 and the cutting device bores 3410 can allow for coupling the cutting device 3400 to the colpotomy device 100 in a manner similar to that described with regards to the cutting device 2600.

In an embodiment where the colpotomy device 100 includes the cutting device 3400, the end effector 106 can also include axial contacts 3500 configured to contact the cutting device contacts 3406, as shown with reference to FIG. 35. In an embodiment, the axial contacts 3500 can include contact surfaces 3502 and 3504, which can allow the axial contacts 3500 to provide current to the cutting device 3400. In particular, as may be seen with reference to FIG. 36, the axial contact surface 3502 can contact the cutting device contact 3460. Furthermore, as may be seen with reference to FIG. 36, the axial contact surface 3504 can contact the circumferential contact 2704. Therefore, the axial contacts 3500 can receive current from the circumferential contact 2704 via the axial contact surface 3504. Moreover, the axial contacts 3500 can provide current to the cutting device 3400 and the cutting device peripheral portion 3404 via the axial contact surface 3502.

As discussed above, the colpotomy device 100 can include the end effector assembly 104 that can have the end effector 106, which can be used for tissue resection. Moreover, as noted above, the end effector 106 can rotate when the knob locking assemblies 108, 1700, and 2200 are rotated by a user in either a clockwise or counterclockwise direction. In an embodiment, as a user rotates the knob locking assemblies 108, 1700, and 2200, the end effector 106 can rotate while the end effector assembly 104 remains stationary. Thus, in an embodiment, the end effector 106 can move relative to the end effector assembly 104. An example of this embodiment is shown with reference to FIG. 37.

Figure 37:
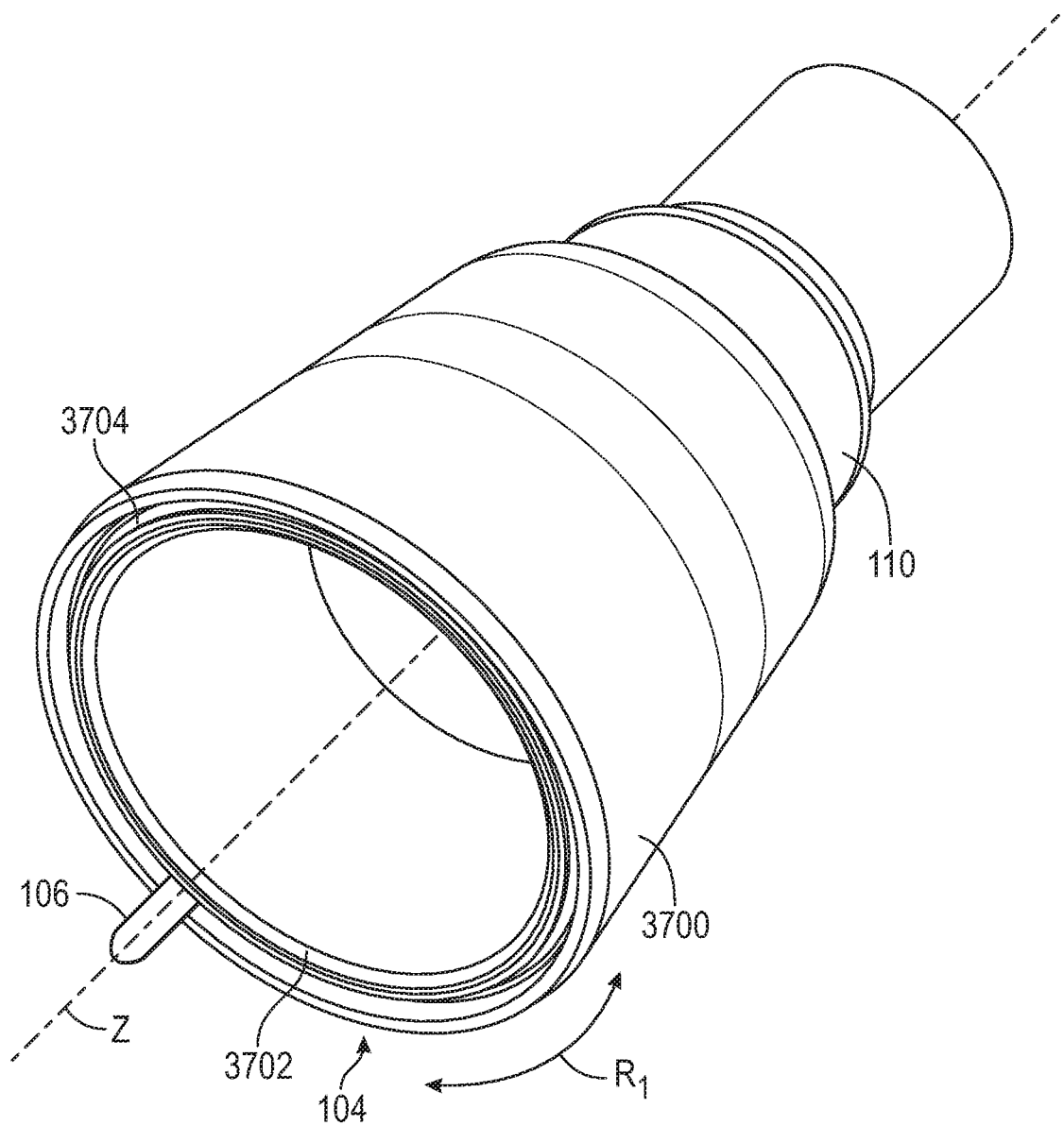
FIGS. 37-39 illustrate an end effector assembly, in accordance with at least one example of the present disclosure.
Figure 38:
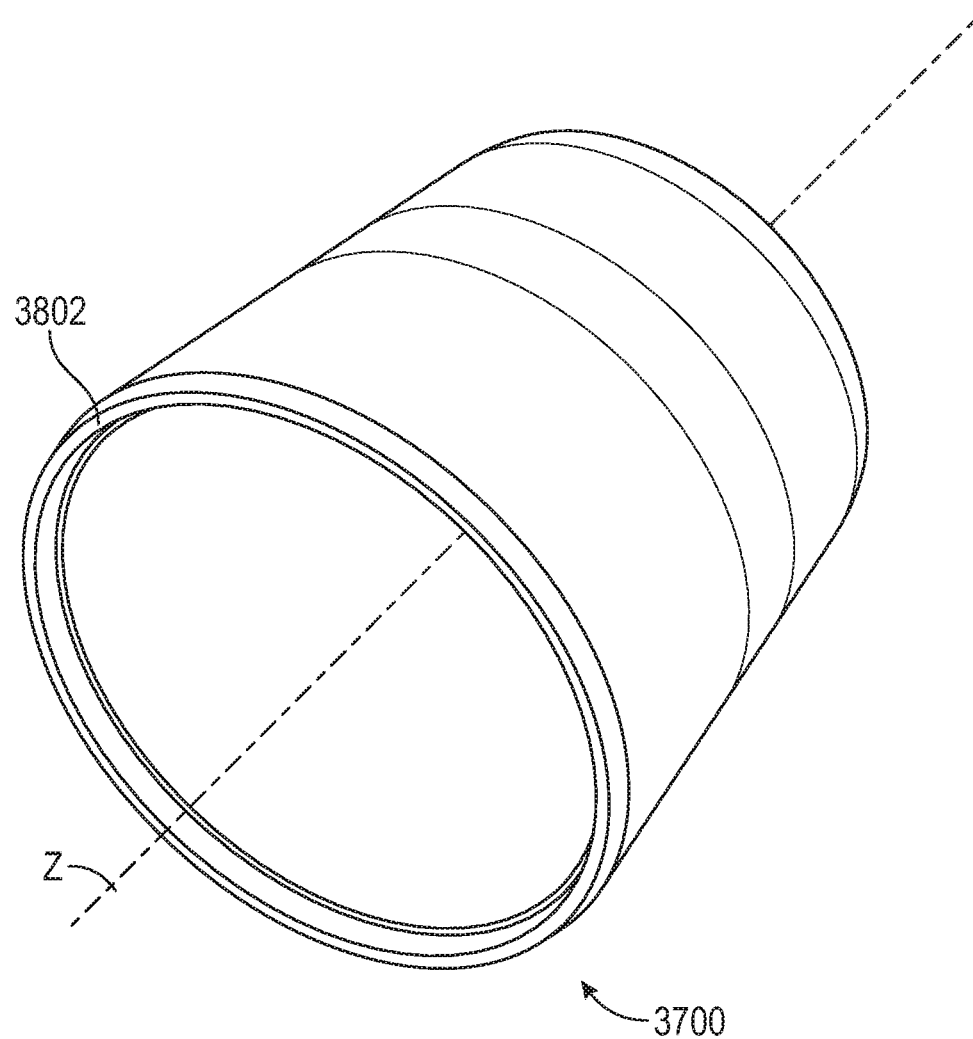
Figure 39:
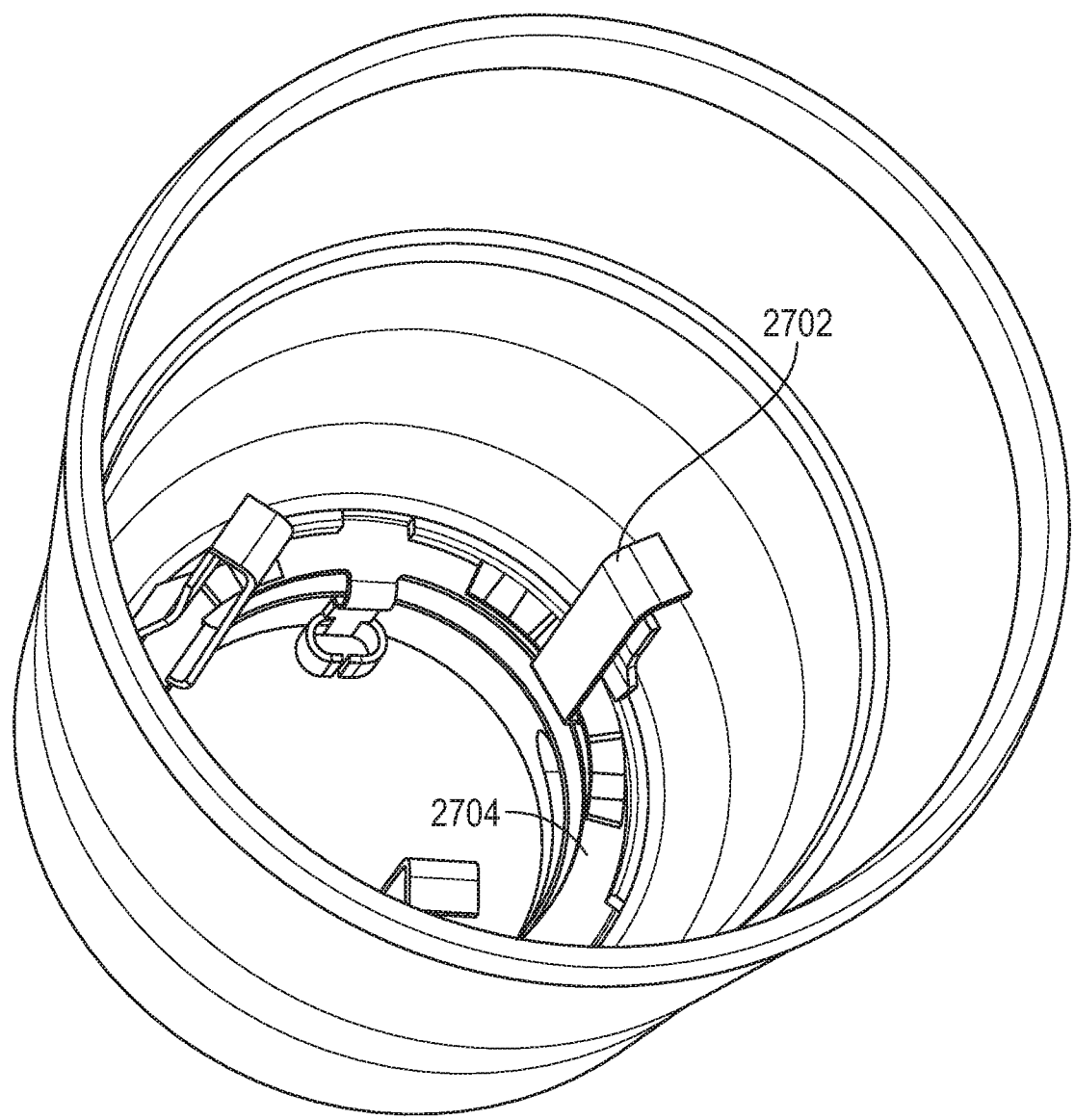
Figure 40:
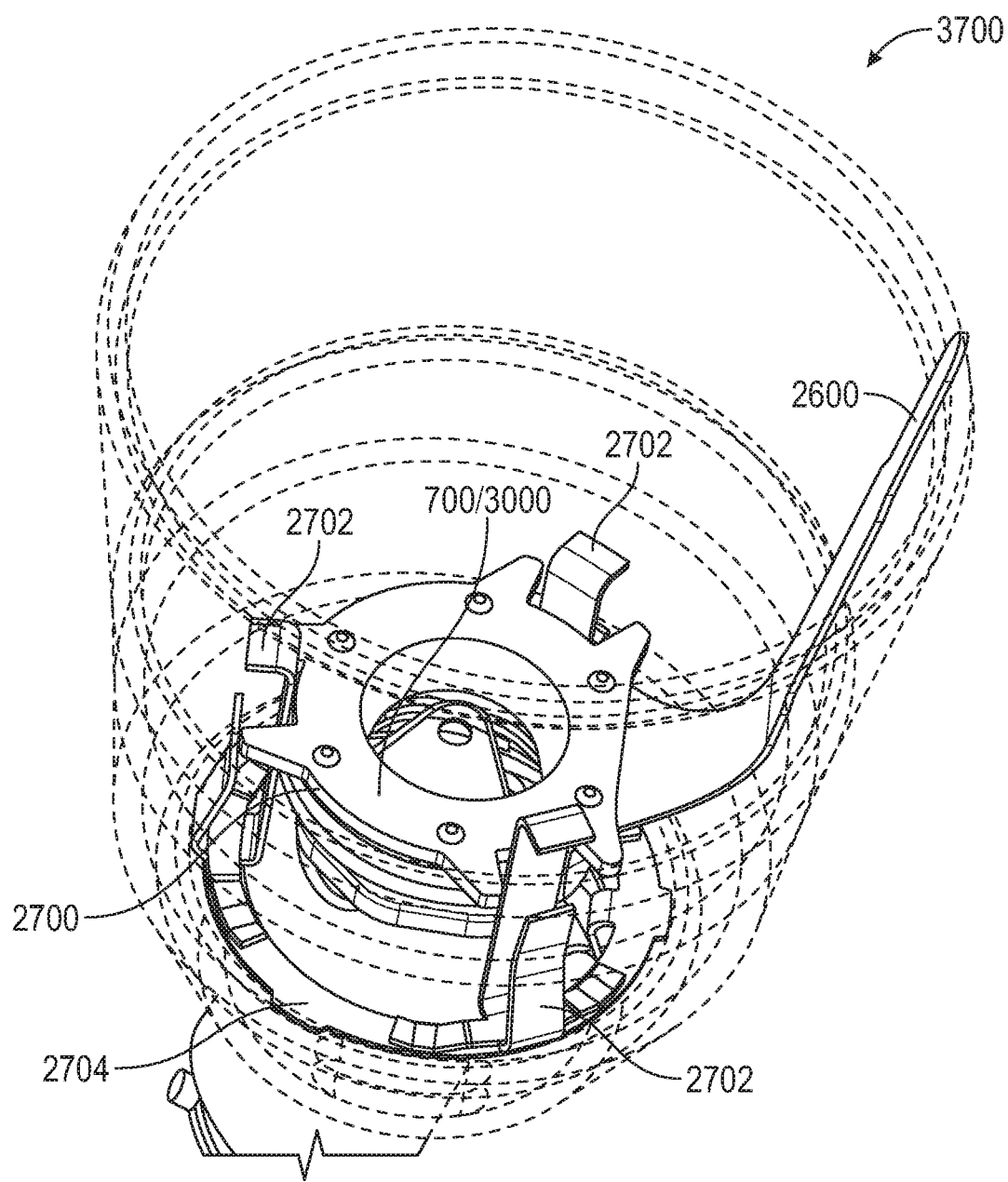
FIG. 40 illustrates the end effector assembly of FIGS. 37-39 housed by first cup where the first cup houses an end effector assembly coupling, a cutting device, a blade cover, an axial contact, and a circumferential contact, in accordance with at least one example of the present disclosure.

FIG. 37 illustrates the end effector assembly 104 in accordance with an embodiment of the present disclosure. In addition to the end effector 106, the end effector assembly 104 can include a first cup 3700 and a second cup 3702 nested within the first cup 3700. Furthermore, the first cup 3700 can be spaced from the second cup 3702 with a spacer assembly 3704. Each of the first cup 3700, the second cup 3702, and the spacer assembly 3704 are centered with respect to a longitudinal coaxial axis Z where each of the first cup 3700 and the second cup 3702 define the longitudinal coaxial axis Z. The first cup 3700 can include a ledge 3800 (FIG. 38) that can hold the circumferential contact 2704 upon which, as described above, the axial contact 2702 stays in contact with and slides during use of the colpotomy device 100 (FIG. 39). Furthermore, in an embodiment, the end effector assembly 104 can be housed by the first cup 3700, such that the first cup 3700 houses the end effector assembly coupling 700, the cutting device 2600, the blade cover 2700, the axial contact 2702, and the circumferential contact 2704, as shown with reference to FIG. 40. The first cup 3700 can have a substantially circular configuration where an opening 3802 can be defined at a distal end of the first cup 3700. In an embodiment, the opening 3802 can have a substantially circular configuration similar to the configuration of the first cup 3700. While the first cup 3700 and the first cup opening 3802 are defined as a having a circular configuration, the first cup 3700 and the first cup opening 3802 can have any three-dimensional configuration.

Figure 41:
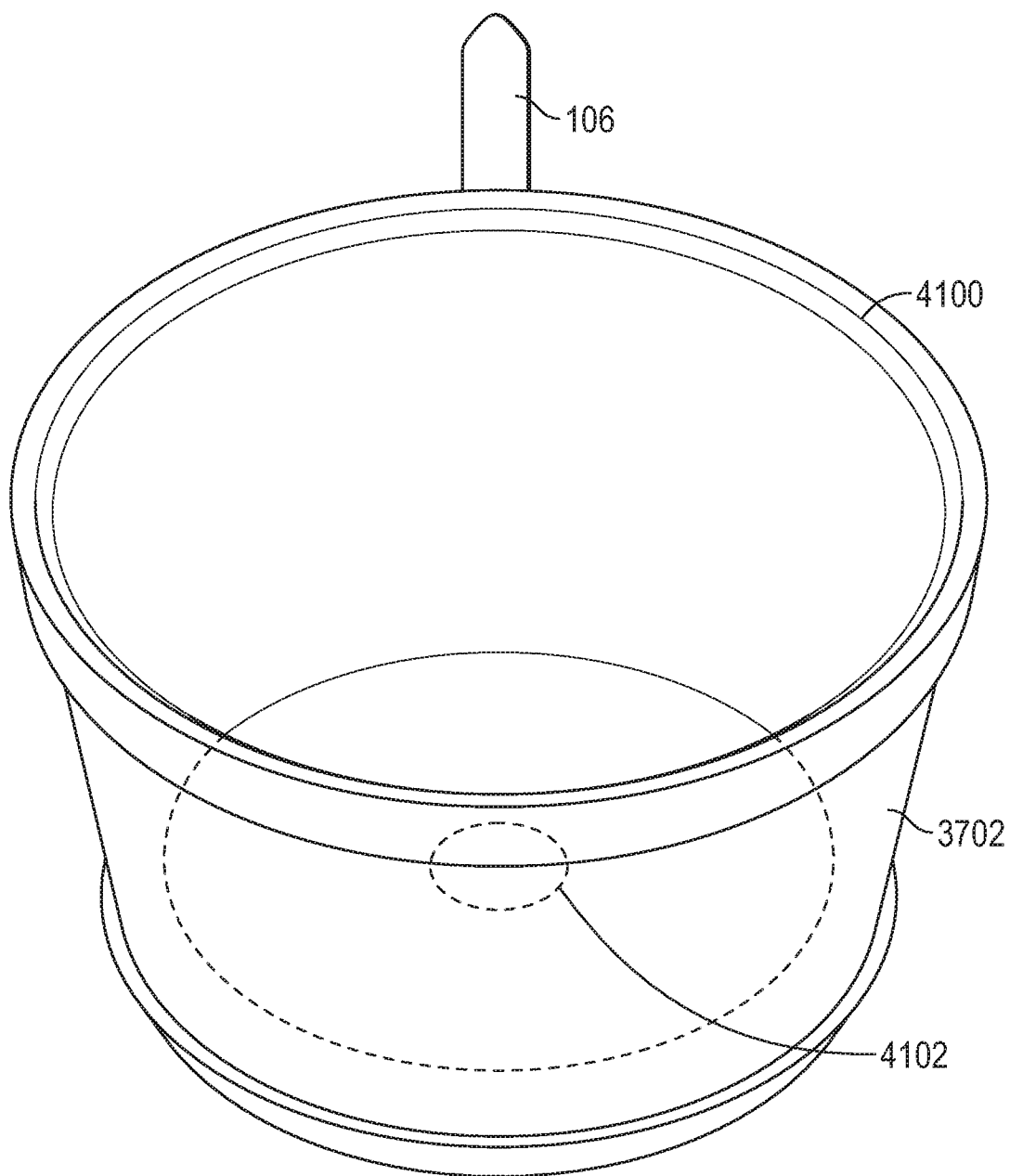
FIG. 41 illustrates a second cup of an end effector assembly, in accordance with at least one example of the present disclosure.

In an embodiment, the second cup 3702 can have a configuration that complements the configuration of the first cup 3700 such that the second cup 3702 can be nested within the first cup 3700. For example, as shown with reference to FIG. 41, the second cup 3702 can have a substantially circular configuration where an opening 4100 can be defined at a distal end of the second cup 3702. In an embodiment, the second cup opening 4100 can have a substantially circular configuration similar to the configuration of the second cup 3702. Moreover, the second 3702 can include a probe aperture 4102 through which the probe 112 can pass. In an embodiment, the spacer assembly 3704 aligns the first cup 3700 with the second cup 3702 such that the probe aperture 4102 aligns with the first cup 3702. While the second cup 3702 and the second cup opening 4100 are defined as a having a circular configuration, the second cup 3702 and the second cup opening 4100 can have any three-dimensional configuration. In an embodiment, each of the first cup 3700 and second cup 3702 may be formed of a rigid material, such as steel, aluminum, or any other type of metal alloy. In a further embodiment, each of the first cup 3700 and second cup 3702 may be formed of a rigid material, such as plastic or any other type of polymer, such as nylon, or any type of material having a low coefficient of friction.

Figure 42:
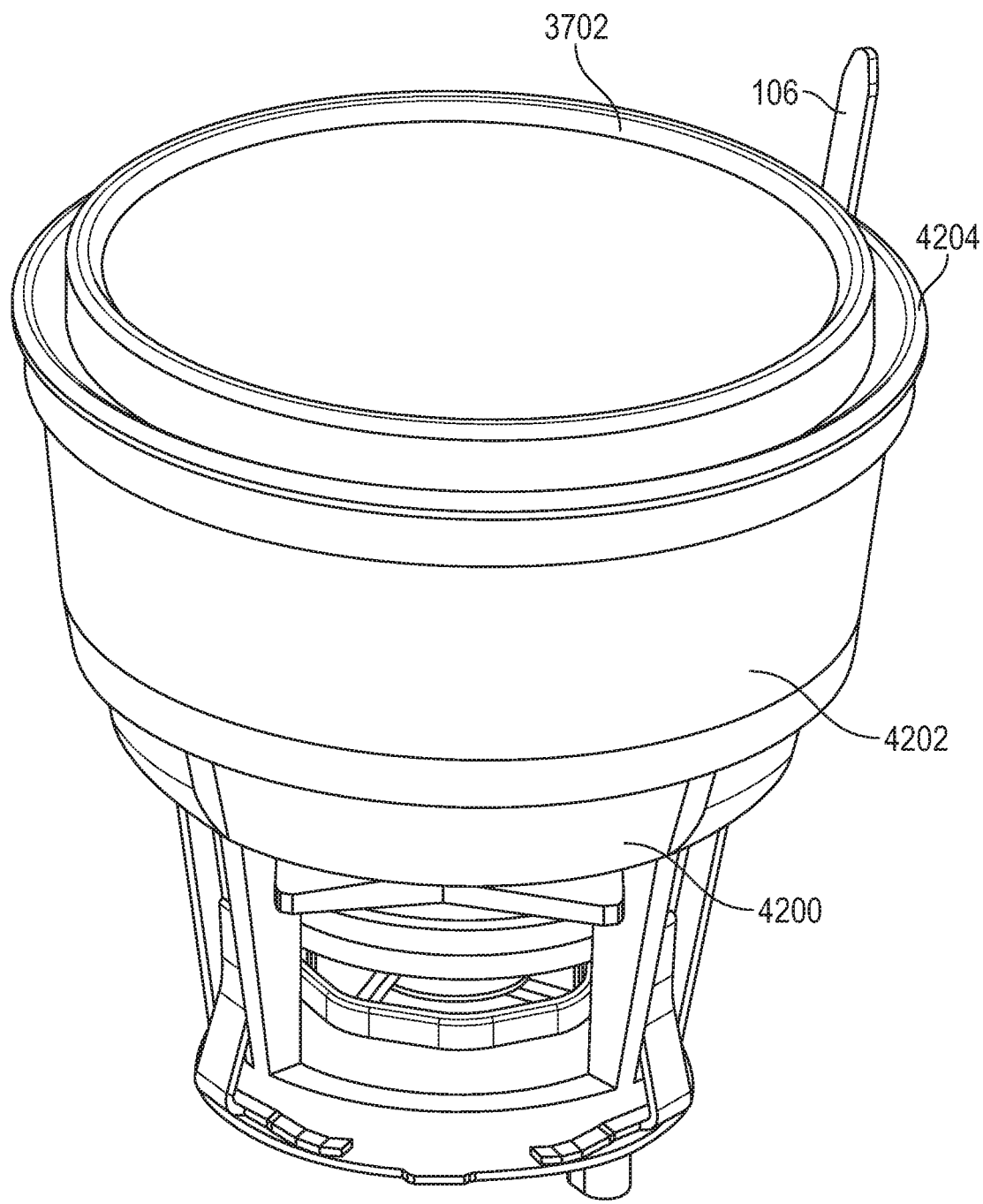
FIG. 42 illustrates an end effector assembly, in accordance with at least one example of the present disclosure.

In an embodiment, the spacer assembly 3704 can function to space the first cup 3702 from the second cup 3704. In addition, the spacer assembly 3704 can allow the movement of the end effector 106 while the first cup 3700 and the second cup 3702 remain stationary. For example, the spacer assembly 3704 can function to allow the end effector 106 to move along the direction R₁ while the first cup 3700 and the second 3702 remain stationary. Thus, the spacer assembly 3704 can function to allow the end effector 106 to move in a circular direction along the direction R₁ in order to make circular incisions. Similarly, the spacer assembly 3704 can function to allow movement of the end effector 106 relative to the end effector assembly 104 such that the end effector assembly 104 can remain stationary while the end effector rotates in conjunction with the knob locking assemblies 108, 1700, and 2200. In an embodiment, the spacer assembly 3704 can include a spacer 4200 disposed within a bushing 4202, as shown with reference to FIG. 42. In an embodiment, the spacer 4200 can define a spacer opening 4204 configured to receive the second cup 3702. In an embodiment, each of the spacer 4200 and the spacer opening 4204 can have a configuration that is complementary to the configuration of the first cup 3700 and the second cup 3702 such that the spacer 4200 can be disposed between the second cup 3702 and the bushing 4202. For example, the spacer 4200 and the spacer opening 4204 can have a substantially circular configuration that is complimentary to the configuration of the first cup 3700 and the second cup 3702.

Figure 43:
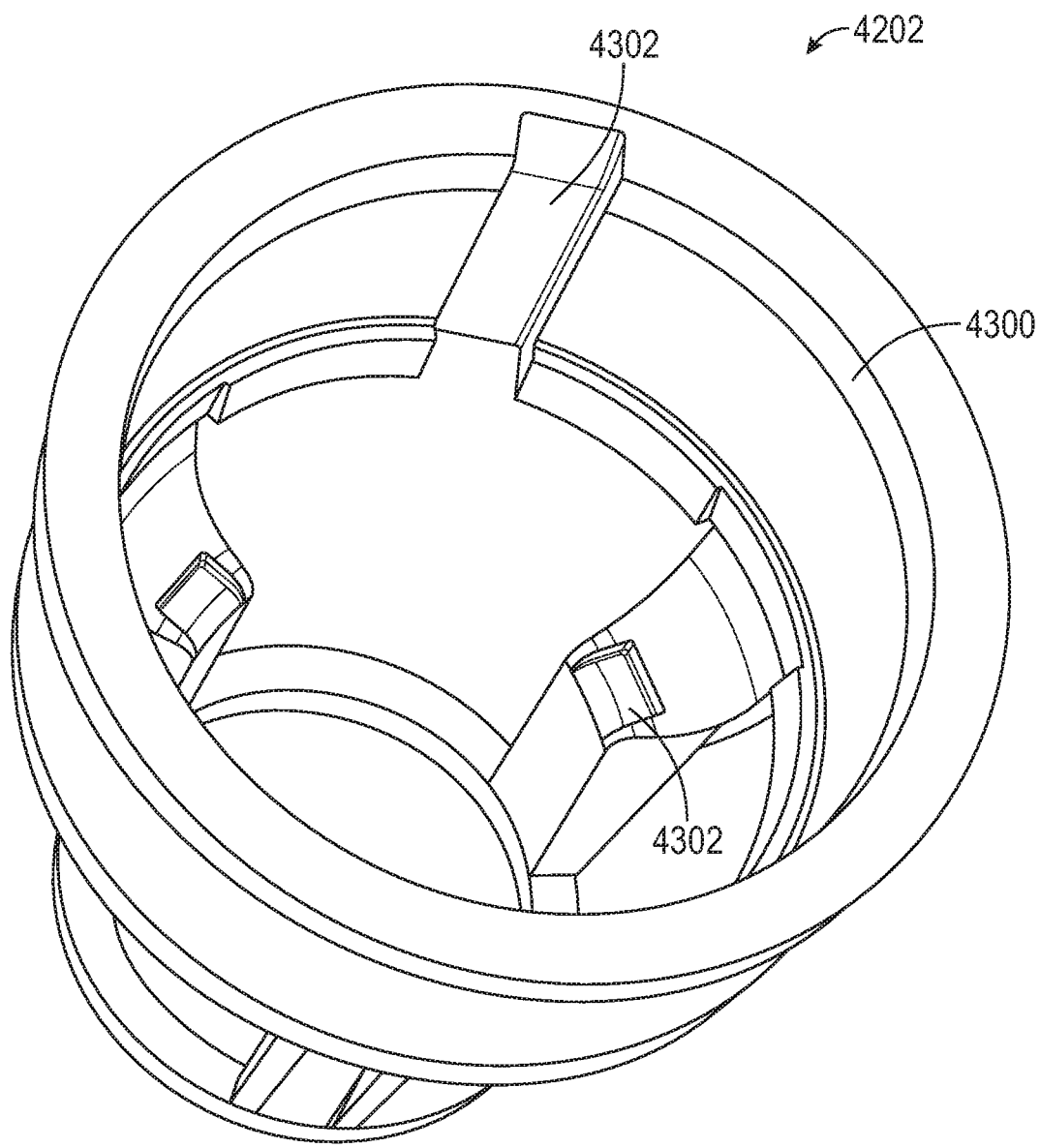
FIG. 43 illustrates a bushing of an end effector assembly, in accordance with at least one example of the present disclosure.

As shown in FIG. 43, in an embodiment, the bushing 4202 can define an opening 4300 that is configured to receive the spacer 4200. In an embodiment, the spacer 4200 may have a frictional fit within the bushing 4202 such that the spacer 4200 rigidly couples with the bushing 4201. Other examples of how the spacer 4200 can rigidly couple with the bushing 4202 can include a key method, placing an adhesive between an inner surface of the bushing 4202 and an outer surface of the spacer 4200, or the like. In an embodiment, the rigid coupling between the spacer 4200 and the bushing 4202 allows for the bushing 4202 to rotate while the spacer 4200 remains stationary. In an embodiment, the bushing 4202 can be a plain bearing, such as a sleeve and flanged bearing, a split bearing, a clenched bearing, a two-piece bearing, an integral plain bearing, or the like.

Figure 44:
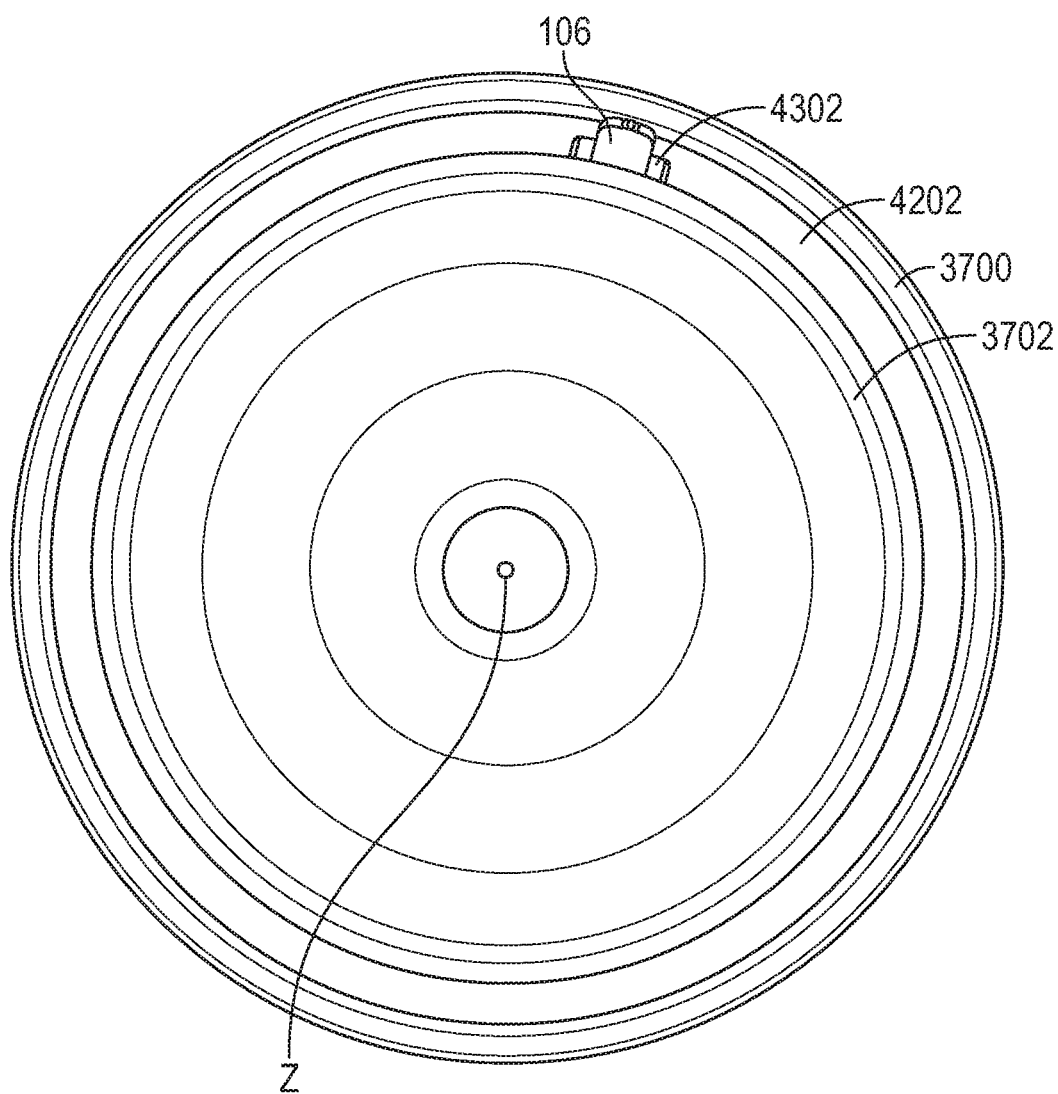
FIG. 44 illustrates a top view of end effector assembly, in accordance with at least one example of the present disclosure.

In order to allow rotation of the end effector 106 along the direction R₁ (FIG. 37) while the first cup 3700 and the second cup 3702 remain stationary, the bushing 4202 can include a recess 4302 that is configured to receive the end effector 104. In particular, the end effector 106 can be disposed in the recess 4302, as shown with regards to FIG. 44, such that as the bushing 4202 rotates along the direction R₁, the end effector 106 can rotate with the bushing 4202. As can be seen with reference to FIG. 44, the end effector 106 can be offset from the longitudinal coaxial axis Z.

In some embodiments, the laparoscopic device 100 can be configured to limit an amount of torque imparted to the knob locking assembly 108 during use of the laparoscopic device 100. In an embodiment, when an amount of torque imparted by a user exceeds an amount of torque necessary for proper operation of the laparoscopic device 100, a clutch assembly can be used that causes slippage to occur such that the couplings 30 no longer rotate. For example, making reference to FIGS. 45A and 45B, the laparoscopic device 100 can include a clutch assembly 4500, which can be used to limit the amount of torque imparted to the couplings 300 by a user via the knob locking assembly 108 in accordance with an embodiment of the present disclosure.

In an embodiment, the clutch assembly 4500 can include a clutch plate 4502 that engages with a clutch housing 4504 via clutch plate teeth 4506 (FIG. 45B) and clutch housing teeth 4508. In particular, as may be seen with reference to FIG. 46, each of the clutch plate teeth 4506 and the clutch housing teeth 4508 have a triangular configuration such that the configuration of the clutch plate teeth 4506 is complementary to the configuration of the clutch housing teeth 4508. It should be noted that while the clutch plate teeth 4506 and the clutch housing teeth 4508 have a triangular configuration and are each described as having complementary triangular configurations, in an embodiment, the clutch plate teeth 4506 and the clutch housing teeth 4508 can have any type of configuration that are complementary. Examples can include a square configuration, a conical configuration, or the like.

Figure 45A:
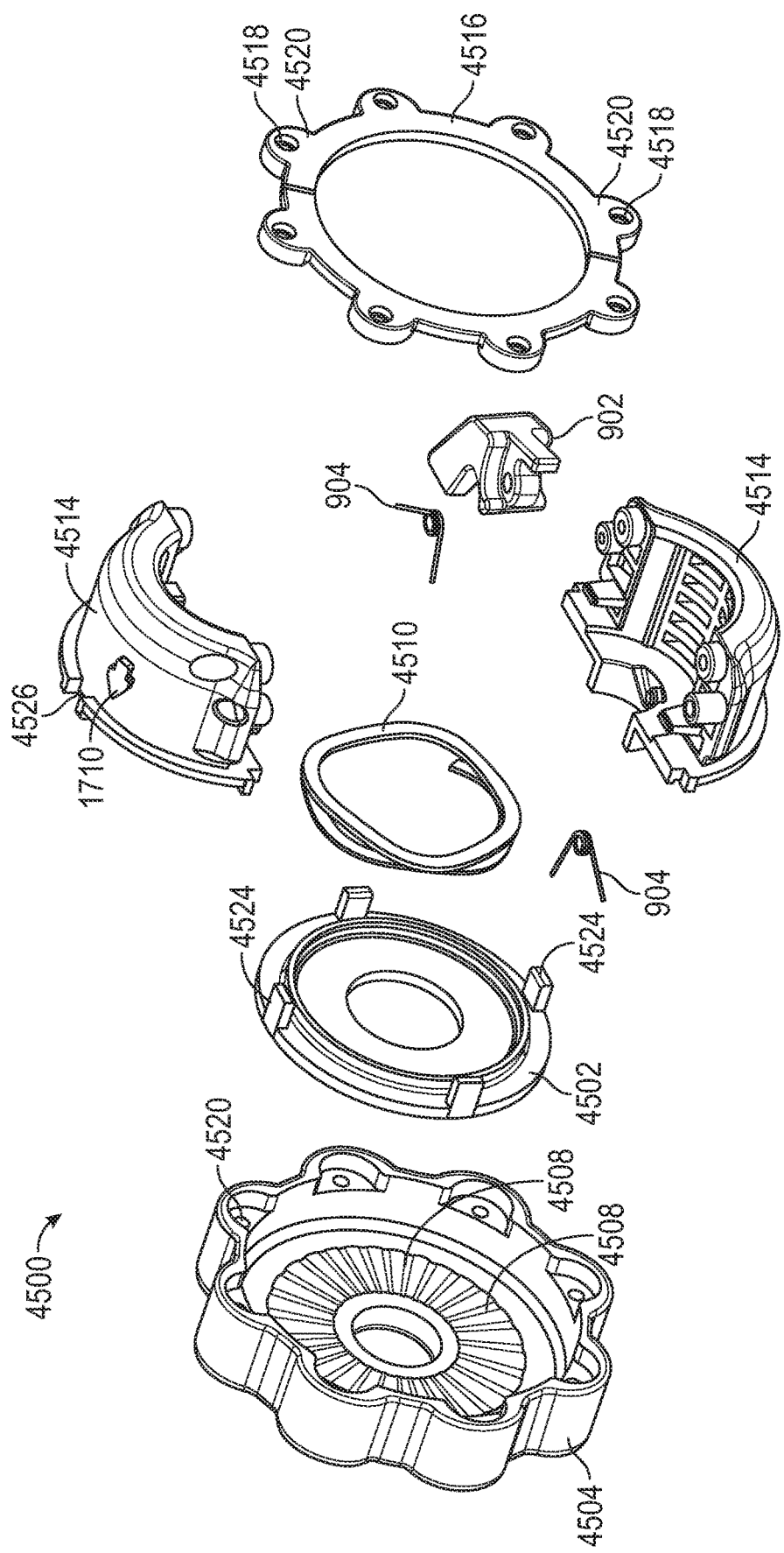
FIGS. 45A and 45B illustrate a clutch assembly, in accordance with at least one example of the present disclosure.
Figure 45B:
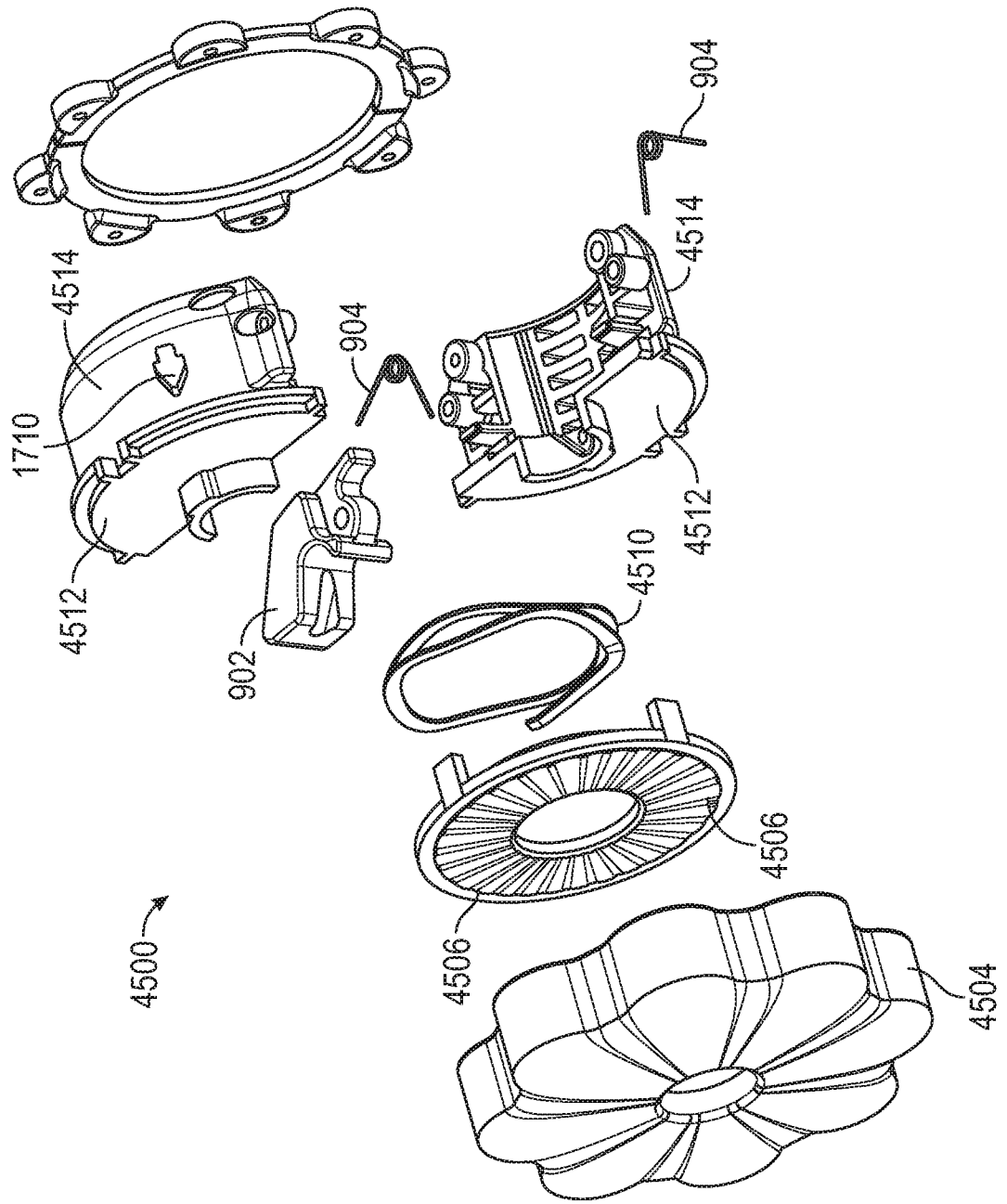
Figure 46:
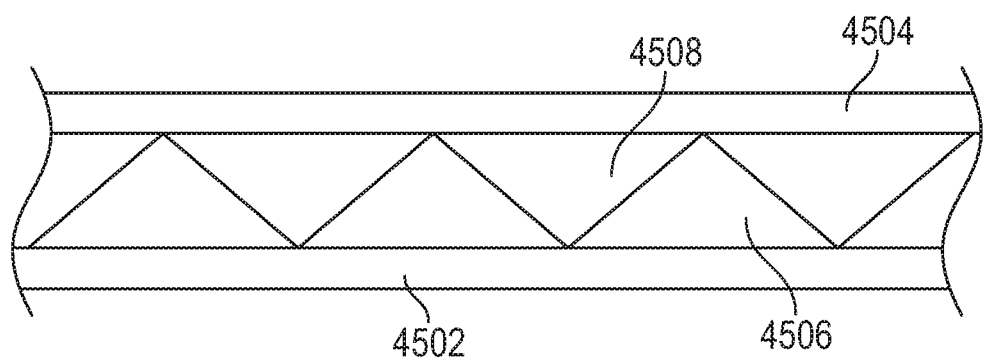
FIG. 46 show the engagement of clutch plate teeth with clutch housing teeth, in accordance with at least one example of the present disclosure.

Returning attention to FIGS. 45A and 45B, in an embodiment, the clutch assembly 4500 can include a biasing member 4510, which biases the clutch plate 4502 against the clutch housing 4504 such that the clutch plate teeth 4506 engage the clutch housing teeth 4508 as shown with reference to FIG. 46. In an embodiment, the biasing member 4510 may be a wave spring, a compression spring, or any other type of biasing mechanism that biases the clutch plate 4502 against the clutch housing 4504. Furthermore, the biasing member 4510 may rest against surface 4512 of knob locking housing portions 4514 such that the biasing means 4510 may impart a biasing force against the clutch plate 4502. In an embodiment, the knob locking housing portions 4514 have functionality similar to the housing portions 900 discussed above, where the housing portions couple with the actuators 902 and the biasing means 904, also as discussed above.

In an embodiment, the clutch assembly can include an end cap 4516 having coupling bores 4518 disposed in flanges 4520, as shown with reference to FIGS. 45A and 45B. The end cap coupling bores 4518 can engage with clutch housing bores 4522 via a fastening means 4700 (FIG. 47) thereby coupling the clutch housing 4504 with the end cap 4516, as shown with respect to FIG. 47. In an embodiment, the fastening means 4700 may be any type of fastening means, such as a threaded fastener, a rivet, or the like. When the clutch housing 4504 couples with the end cap 4516, the clutch housing 4504 encloses the clutch plate 4502, the biasing member 4510, the clutch plate teeth 4506, and the clutch housing teeth 4508, as shown with reference to FIG. 47. Furthermore, the clutch plate 4502 includes tabs 4524 that are configured to engage with slots 4526 of the knob locking housing portion 4514. More specifically, in the configuration shown with reference to FIG. 47, the clutch plate tabs 4524 sit within the knob lock housing portion slots 4526. Here, the clutch plate tabs 4524 engage with the knob lock housing portion slots 4526 such that when a user rotates the clutch housing 4504, the clutch plate tabs 4524 impart a force against the knob lock housing portion slots 4526 and the knob lock housing portions 4514, thereby causing rotation of the couplings 300.

Figure 48:
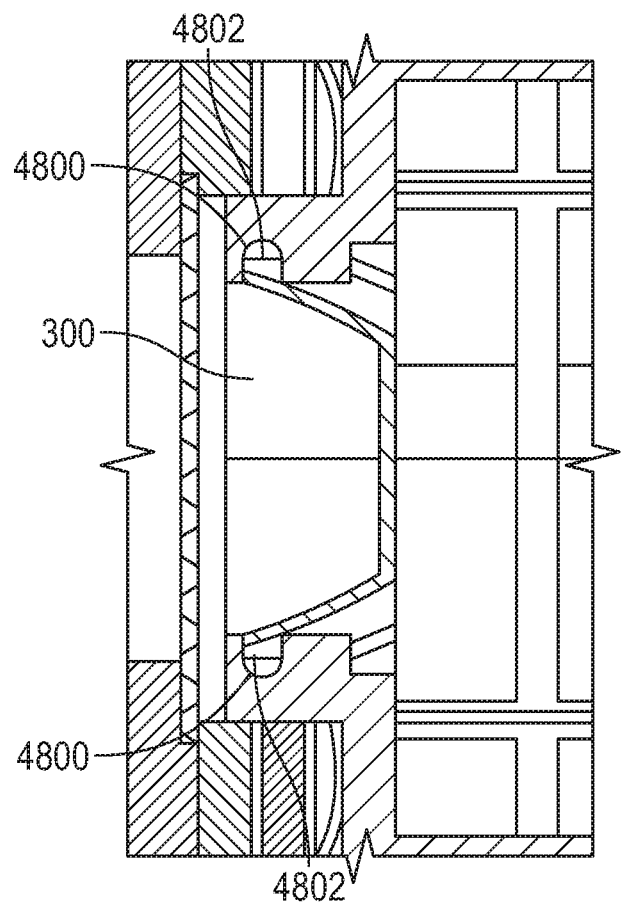
FIGS. 48 and 49 illustrate recesses of the clutch assembly of FIGS. 45A and 45B that are configured to receive coupling bosses, in accordance with at least one example of the present disclosure.
Figure 49:
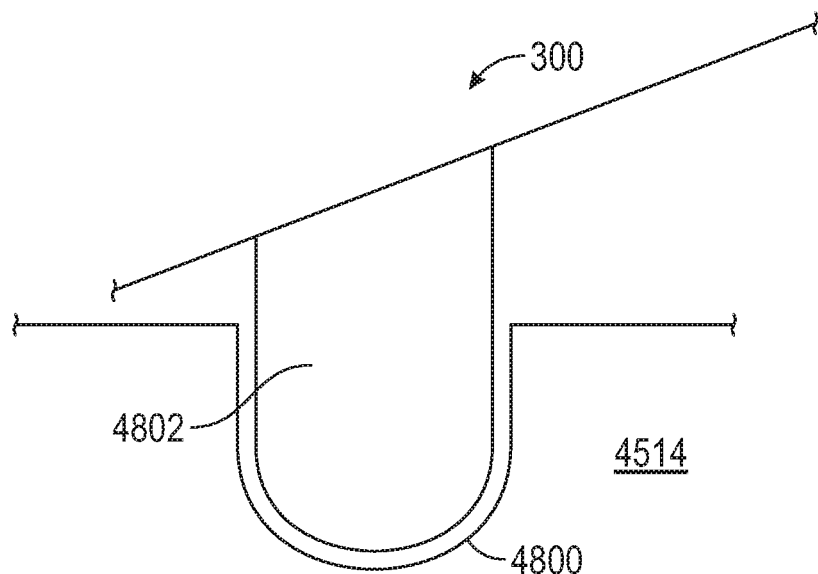

Regarding the rotation of the couplings 300, as shown with reference to FIGS. 48 and 49, the knob lock housing portions 4514 include recesses 4800 that are configured to receive coupling bosses 4802. Here, when a user rotates the clutch housing 4504, the clutch plate 4502 translates the rotational force to the knob lock housing portion recesses 4800 such that the knob lock housing portion recesses 4800 rotate along with the clutch housing 4504. Moreover, as the knob lock housing portion recesses 4800 rotate, by virtue of being disposed within the knob lock housing portion recesses 4800, the coupling bosses 4802 and the couplings 300 rotate.

Figure 47:
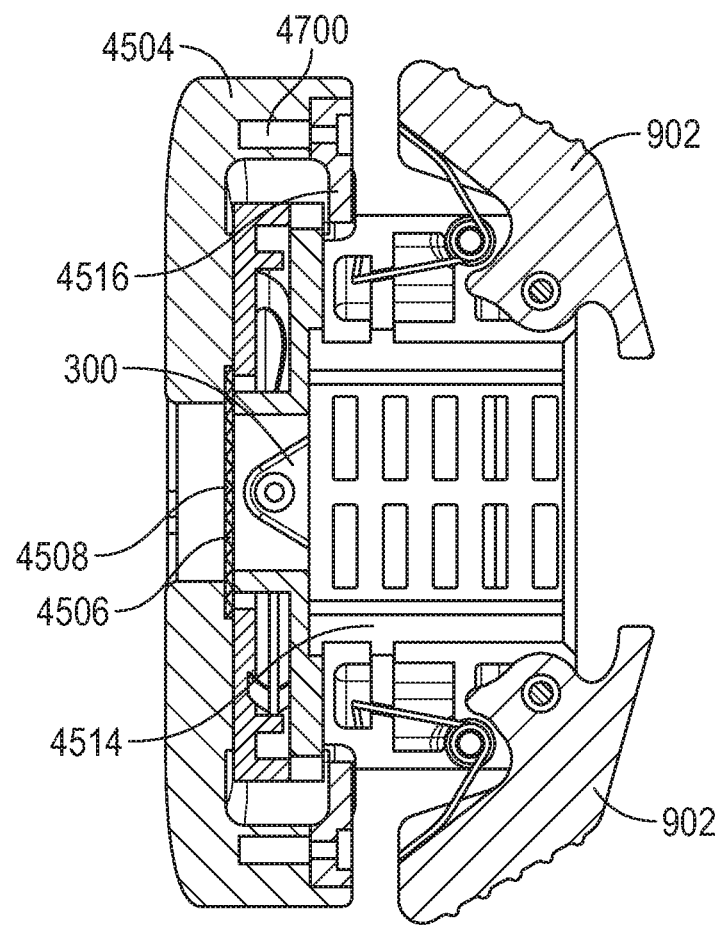
FIG. 47 illustrates an assembled view of the clutch assembly of FIGS. 45A and 45B, in accordance with at least one example of the present disclosure.
Figure 50:
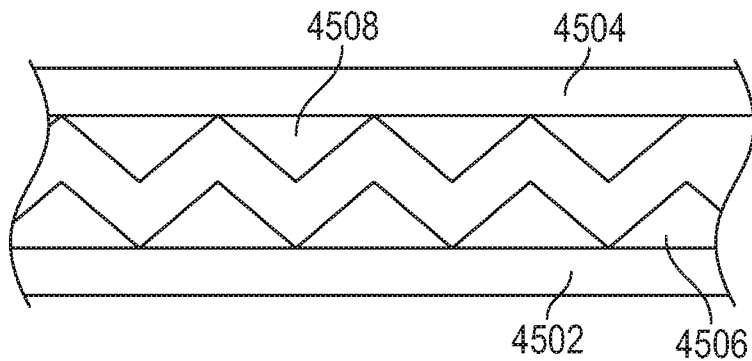
FIGS. 50 and 51 illustrate the disengagement of clutch housing teeth from clutch plate teeth, in accordance with at least one example of the present disclosure.
Figure 51:
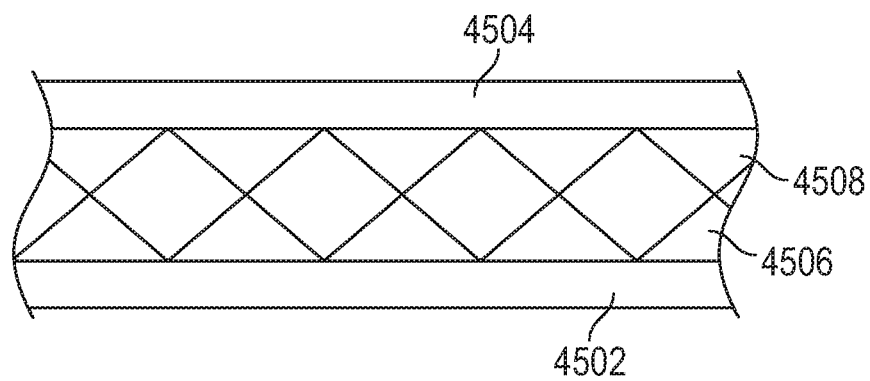

However, when a user imparts an excessive amount of torque on the clutch housing 4504, the clutch housing teeth 4508 disengage from the clutch plate teeth 4506 and slide over each other as shown with reference to FIGS. 50 and 51. Therefore, as the user continues to rotate the clutch housing 4504 with excessive torque, by virtue of the clutch housing teeth 4508 disengaging from the clutch plate teeth 4506, the clutch plate 4502 does not translate the rotational force to the knob lock housing portion recesses 4800 such that the knob lock housing portion recesses 4800 do not rotate along with the clutch housing 4504. Moreover, since the knob lock housing portion recesses 4800 do not rotate, the coupling bosses 4802 and the couplings 300 do not rotate. It should be noted that while FIG. 47 illustrates the clutch housing 4504 coupling with the knob lock housing portion 4514, in an embodiment, the assembly disclosed in FIGS. 45A-49 can be incorporated with the embodiments discussed above with reference to FIGS. 9-16 where the clutch housing 4504 couples with the housing portion 900 as discussed with reference to FIGS. 45A, 45B, and 47. As such, when an excessive amount of torque is applied by a user to the laparoscopic device 100, the clutch assembly 4500 can prevent the excessive torque from being translated to the couplings 300 in embodiments using the housing portion 900.

Figure 52A:
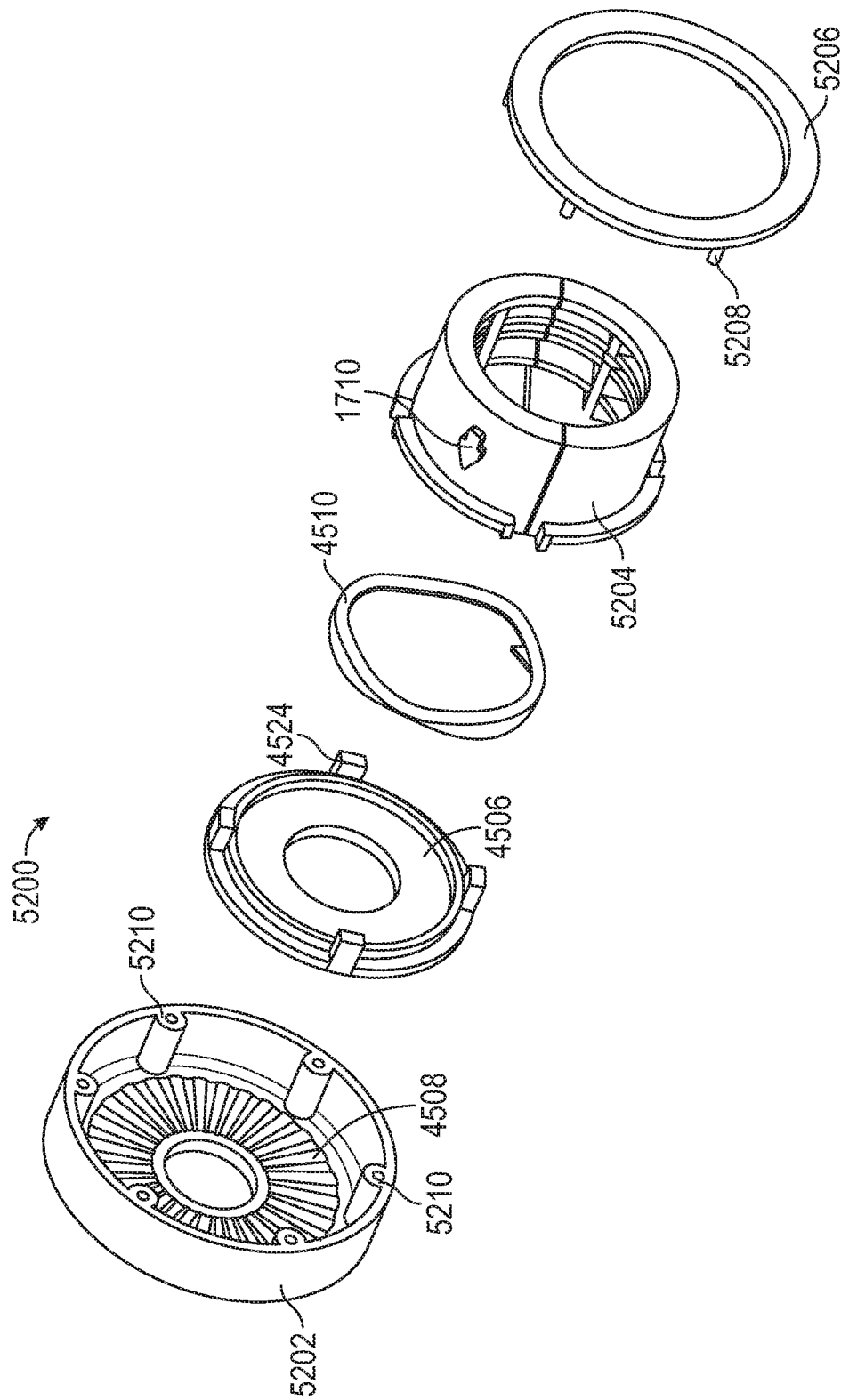
FIGS. 52A, 52B, and 53 illustrate a clutch assembly, in accordance with at least one example of the present disclosure.
Figure 52B:
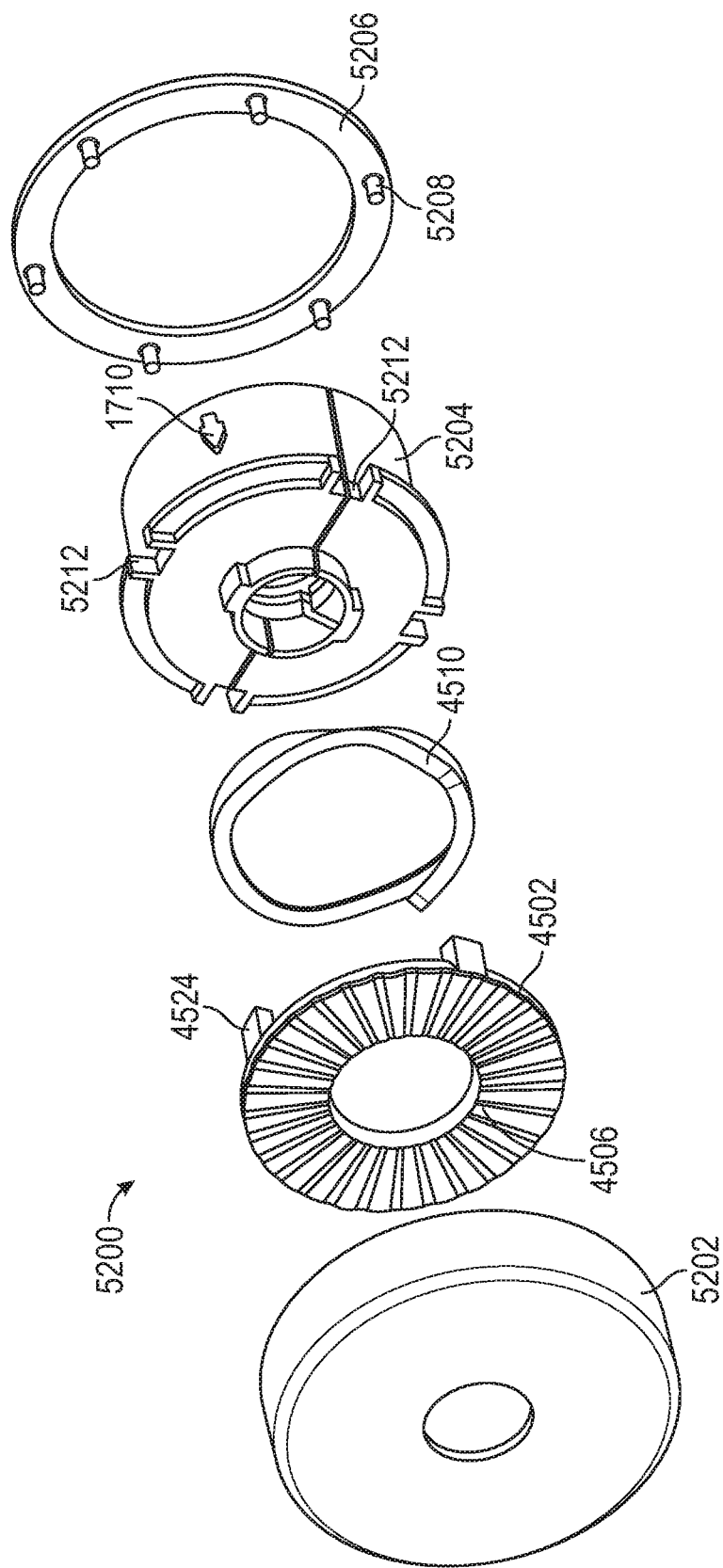

In addition to the embodiments discussed with reference to FIGS. 45A-51, the laparoscopic device 100 can include a clutch assembly 5200, which can be used to limit the amount of torque imparted to the couplings 300 by a user via the knob locking assembly 108 as shown with respect to FIGS. 52A and 52B, in accordance with an embodiment of the present disclosure. Here, the clutch assembly 5200 can include the clutch plate 4502 that engages with a clutch housing 5202 via the clutch plate teeth 4506 and the clutch housing teeth 4508. In an embodiment, the clutch assembly 5200 can include the biasing member 4510 along with a knob lock housing portion 5204 and an end cap 5206.

Figure 53:
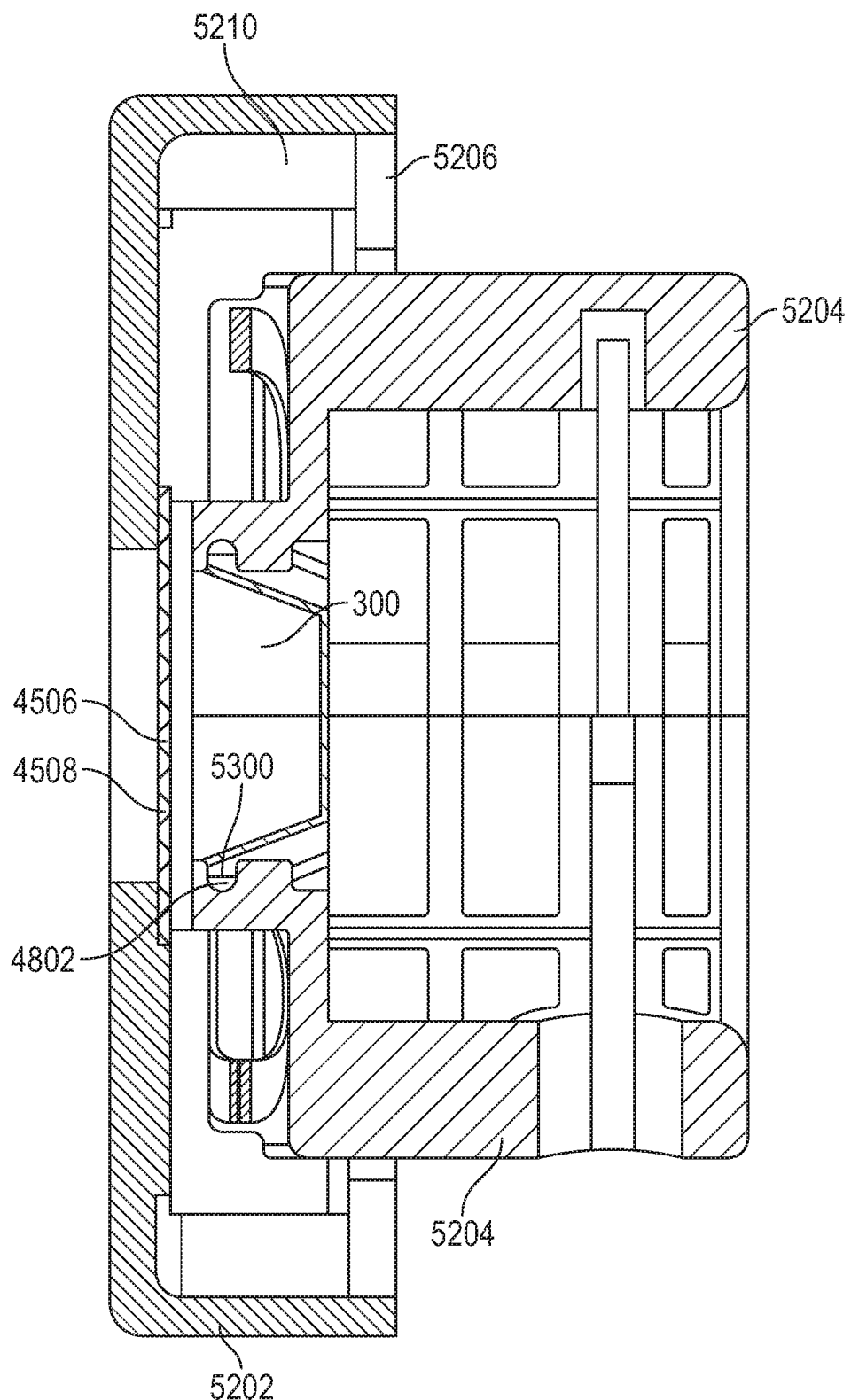

In an embodiment, the end cap 5206 can include end cap tabs 5208 that are configured to engage with clutch housing recesses 5210 when the end cap 5206 couples with the clutch housing 5202, as shown with reference to FIG. 53. When the clutch housing 5202 couples with the end cap 5206, the clutch housing 5202 encloses the clutch plate 4502, the biasing member 4510, the clutch plate teeth 4506, and the clutch housing teeth 4508, as shown with reference to FIG. 53. Moreover, the knob locking housing portion 5204 includes slots 5212 that are configured to engage with the clutch plate tabs 4524. More specifically, in the configuration shown with reference to FIG. 53, the clutch plate tabs 4524 sit within the knob lock housing portion slots 5212. Here, the clutch plate tabs 4524 engage with the knob lock housing portion slots 5212 such that when a user rotates the clutch housing 5202, the clutch plate tabs 4524 impart a force against the knob lock housing portion slots 5212 and the knob lock housing portions 5204, thereby causing rotation of the couplings 300.

With respect to the rotation of the couplings 300, as shown with reference to FIG. 53, the knob lock housing portions 5204 include recesses 5300 similar to the knob lock housing portion recesses 4800 that are configured to receive the coupling bosses 4802. Here, when a user rotates the clutch housing 5202, the clutch plate 4502 translates the rotational force to the knob lock housing portion recesses 5300 such that the knob lock housing portion recesses 5300 rotate along with the clutch housing 5202. As the knob lock housing portion recesses 5300 rotate, since the coupling bosses 4802. are disposed within the knob lock housing portion recesses 5300, the coupling bosses 4802 and the couplings 300 rotate along with the knob locking portion recesses 5300.

As discussed above with reference to FIGS. 50 and 51, when a user imparts an excessive amount of torque on the clutch housing 5202, the clutch housing teeth 4508 disengage from the clutch plate teeth 4506 and slide over each other as shown with reference to FIGS. 50 and 51. Therefore, as the user continues to rotate the clutch housing 5202 with excessive torque, by virtue of the clutch housing teeth 4508 disengaging from the clutch plate teeth 4506, the clutch plate 4502 does not translate the rotational force to the knob lock housing portion recesses 5300 such that the knob lock housing portion recesses 5300 do not rotate along with the clutch housing 5202. Moreover, since the knob lock housing portion recesses 5300 do not rotate, the coupling bosses 4802 and the couplings 300 do not rotate. It should be noted that while FIG. illustrates the clutch housing 5202 coupling with the knob lock housing portion 5204, in an embodiment, the assembly disclosed in FIGS. 52A-53 can be incorporated with the embodiments discussed above with reference to FIGS. 17-21 where the clutch housing 5202 couples with the housing portion 1702 as discussed with reference to FIGS. 52A-53 above. Accordingly, when an excessive amount of torque is applied by a user to the laparoscopic device 100 that includes the housing portion 1702, the clutch assembly 5200 can prevent the excessive torque from being translated to the couplings 300.

Figure 54:
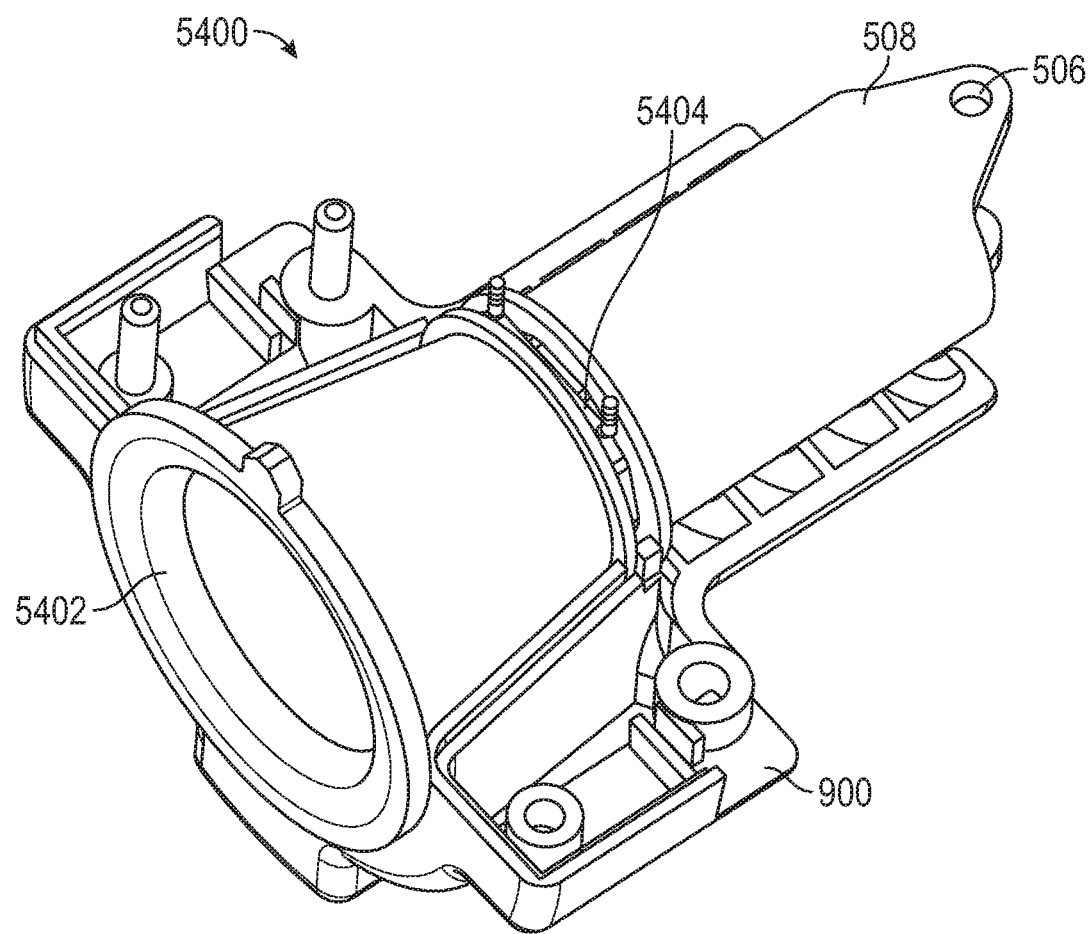
FIG. 54 shows a clutch assembly, in accordance with at least one example of the present disclosure.

In addition to the embodiments discussed with reference to FIGS. 45A-53, the laparoscopic device 100 can include a clutch assembly 5400, which can be used to limit the amount of torque imparted to the couplings 300 by a user via the knob locking assembly 108 as shown with respect to FIG. 54, in accordance with an embodiment of the present disclosure. In this embodiment, the clutch assembly 5400 can include a clutch 5402 along with a biasing means 5404 disposed on the clutch 5402. The clutch 5402 can include the coupling bores 506 on the u-shaped portion 508. In an embodiment, the clutch 5402 couples with the couplings 300 via the coupling bores 506. Thus, when the clutch 5402 rotates, the couplings 300 can also rotate.

In an embodiment, the biasing means can include a pliable member 5500 and posts 5502, as shown with reference to FIGS. 55 and 56, which are side and top views of the biasing member 5404, in accordance with embodiments of the present disclosure. In an embodiment, the biasing means may be formed from any type of ductile material that flexes in the direction C when the biasing member 5404 is compressed in either the direction A or in a direction D and rebounds along the direction B when the biasing member 5404 is no longer compressed. Example of materials that may be used for the biasing means include any type of pliable metal or semi-rigid polymer, including plastic or the like.

Figure 58:
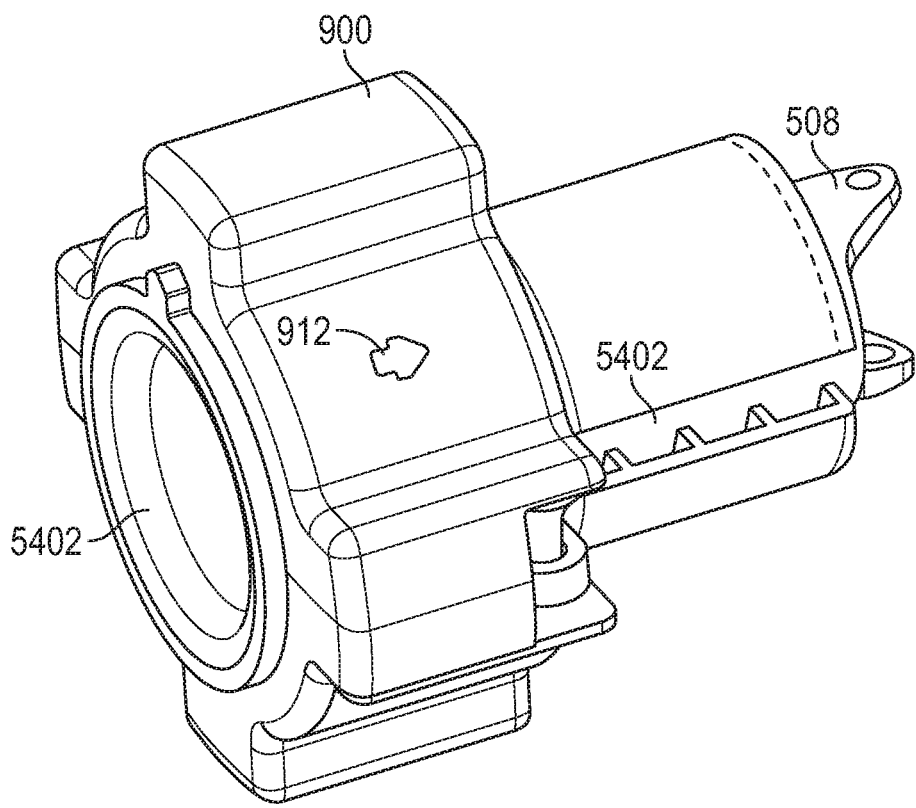
FIG. 58 shows the clutch assembly of FIG. 54 coupled with the knob locking assembly of FIG. 9, in accordance with at least one example of the present disclosure.
Figure 59:
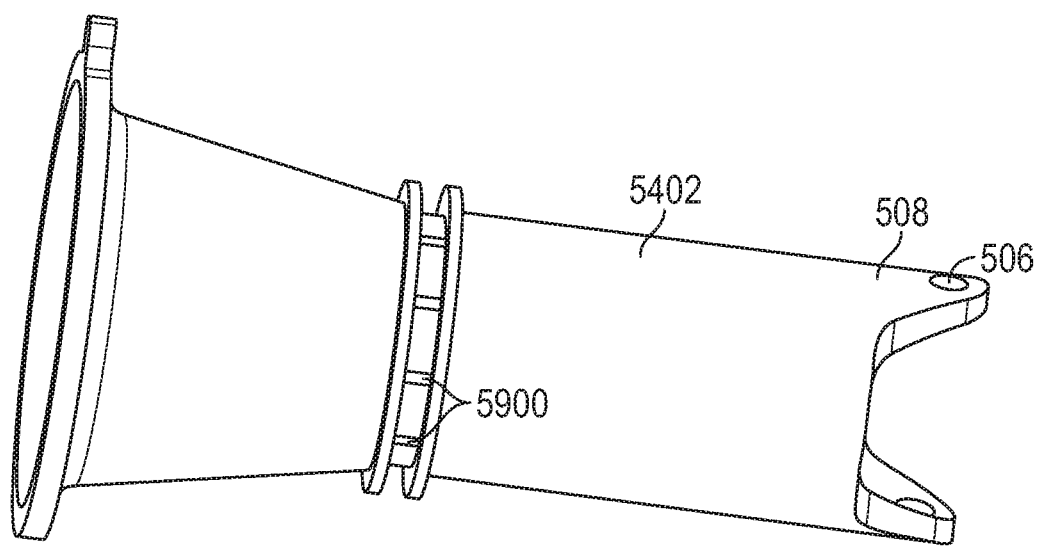
FIG. 59 shows stops of the clutch assembly of FIG. 54, in accordance with at least one example of the present disclosure.
Figure 60:
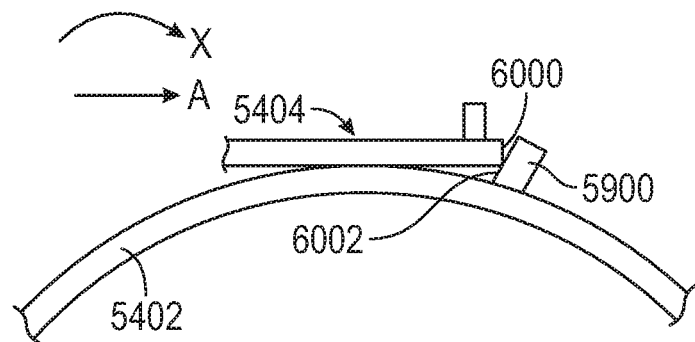
FIGS. 60-62 illustrate an interaction of the biasing member of FIGS. 55 and 56 with the stops of the clutch of FIG. 59, in accordance with at least one example of the present disclosure.

As noted above, the biasing member includes the posts 5502. In an embodiment, the posts 5502 can facilitate coupling of the biasing member 5404 with the housing portion 900. For example, in an embodiment, the housing portion 900 can include recesses 5700 (FIG. 57) within which the posts 5502 may reside when the housing portion 900 is disposed on the clutch assembly 5400, as shown with reference to FIG. 58. In this embodiment, when a user turns the housing portion 900 during use of the laparoscopic device 100, by virtue of the posts 5502 residing within the recesses 5700, the biasing member 5404 rotates along with the housing portion 900. In an embodiment, as shown with regards to FIG. 59, the clutch 5400 can include stops 5900. When a user turns the housing portion 900 along the direction X, an end 6000 (FIG. 60) of the biasing member 5404 abuts an end 6002 of the stop 5900. As the end 6000 abuts the stop 5900, the force applied by turning the housing portion 900 causes the biasing member 5404 to apply a force along the direction A, thereby causing rotation of the clutch 5402 and the couplings 300 along the direction X, as discussed above and shown with reference to FIG. 60.

Figure 61:
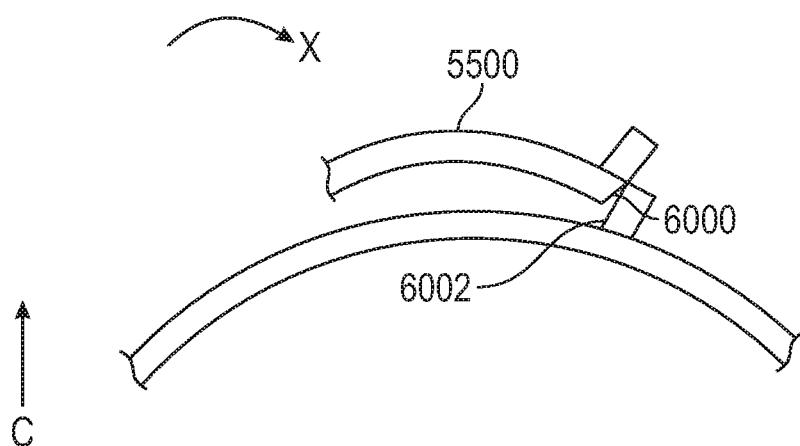
Figure 62:
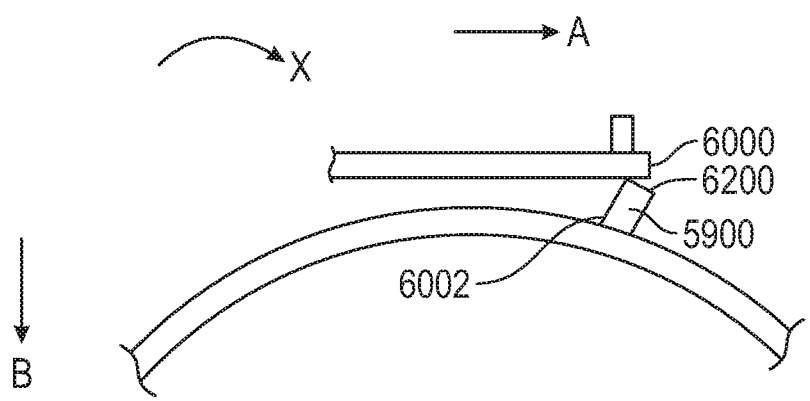

In an embodiment, if a user applies excessive torque to the housing portion 900, i.e., the user turns the housing portion 900 with excessive force, the excessive force is translated to the biasing member 5404 such that the pliable member 5500 of the biasing member 5404 begins to compress along the direction A and flex along the direction C, as shown with respect to FIG. 61. As the pliable member 5500 of the biasing member 5404 continues to flex, the biasing member end 6000 moves along the stop end 6002 along the direction C until the biasing member end 6000 clears the stop end 6002 such that the biasing member 5400 is above the stop 5900, as shown with reference to FIG. 62. When the biasing member 5404 and the biasing member end 6000 slide across a top 6200 of the stop 5900, the biasing member 5404 no longer applies a force along the direction A against the stop 5900 such that the clutch 5402 nor the couplings 300 no longer rotate. Therefore, when an excessive amount of torque is applied by a user to the laparoscopic device 100, the clutch 5402 can prevent the excessive torque from being translated to the couplings 300.

Accordingly, what has been described includes a colpotomy device for performing a hysterectomy. The colpotomy device can include a knob assembly at a distal end and a rotatable cutting implement at a distal end opposite the knob, where the knob assembly can be used to control the movement of the cutting implement. The knob assembly can couple to the cutting implement via a flexible drive tube having a plurality of couplings. In an embodiment, the plurality of couplings can be in series and can be rotatable about a bending axis of the flexible drive tube. Moreover, the end effector assembly can include an axial electrical contact that engages with and slides along a circumferential electric contact in order to provide current to the cutting implement during use of the colpotomy device. The end effector assembly can be housed within a first cup having a second cup nested therein. In an embodiment, the cutting implement can be disposed between the first cup and the second cup and rotatable relative to the first cup and the second cup such that the first cup and the second cup can remain stationary while the cutting implement rotates.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A medical device comprising:
   a tissue incision assembly comprising:
   a first cup;
   a second cup, wherein the first cup is nested within the second cup;
   a spacer assembly between the first cup and the second cup to maintain a spacing therebetween, the spacer assembly including a recess; and
   a cutting implement disposed within the recess, the cutting implement including at least a portion extending between, and movable with respect to, the first and second cups.

2. The medical device of claim 1, wherein the cutting implement is extendable and retractable in a longitudinal axial direction that is spaced apart by an offset distance from a longitudinal coaxial axis defined by at least one of the first and second cups.

3. The medical device of claim 1, wherein the first cup includes a probe aperture at a bottom of the first cup.

4. The medical device of claim 1, wherein the spacer assembly is configured to align the first cup with the second cup such that a probe aperture of the first cup aligns with the second cup.

5. The medical device of claim 1, wherein the spacer includes a bushing, the recess being disposed within the bushing and the bushing being configured to allow rotation of the cutting implement while the first cup and the second cup remain stationary.

6. The medical device of claim 5, wherein the bushing moves along with the cutting implement with respect to the first cup and the second cup.

7. The medical device of claim 1, wherein the spacer assembly is configured to rotate with the cutting implement.

8. A medical device comprising:
    a tissue incision assembly comprising:
        a first cup;
        a second cup, wherein the first cup is nested within the second cup;
        a spacer assembly between the first cup and the second cup to maintain a spacing therebetween, the spacer assembly including a recess; and
        a cutting implement disposed within the recess, the cutting implement including at least a portion extending between, and movable with respect to, the first and second cups, to provide a circular cut guided via the spacing between the first and second cups,
    wherein the spacer assembly is configured to align the first cup with the second cup such that a probe aperture of the first cup aligns with the second cup.

9. The medical device of claim 8, wherein the cutting implement is extendable and retractable in a longitudinal axial direction that is spaced apart by an offset distance from a longitudinal coaxial axis defined by at least one of the first and second cups.

10. The medical device of claim 8, wherein the first cup includes a probe aperture at a bottom of the first cup.

11. The medical device of claim 8, wherein the spacer includes a bushing, the recess being disposed within the bushing and the bushing being configured to allow rotation of the cutting implement while the first cup and the second cup remain stationary.

12. The medical device of claim 11, wherein the bushing moves along with the cutting implement with respect to the first cup and the second cup.

13. The medical device of claim 8, wherein the spacer assembly is configured to rotate with the cutting implement.

14. A medical device comprising:
    a tissue incision assembly comprising:
        a first cup;
        a second cup, wherein the first cup is nested within the second cup;
        a spacer assembly between the first cup and the second cup to maintain a spacing therebetween;
        a cutting implement, including at least a portion extending between, and movable with respect to, the first and second cups, wherein the spacer includes a bushing having a recess disposed therein where the cutting implement is disposed within the recess, the bushing being configured to allow rotation of the cutting implement while the first cup and the second cup remain stationary.

15. The medical device of claim 14, wherein the cutting implement is extendable and retractable in a longitudinal axial direction that is spaced apart by an offset distance from a longitudinal coaxial axis defined by at least one of the first and second cups.

16. The medical device of claim 14, wherein the first cup includes a probe aperture at a bottom of the first cup.

17. The medical device of claim 14, wherein the spacer assembly is configured to align the first cup with the second cup such that probe aperture of the first cup aligns with the second cup.

18. The medical device of claim 14, wherein the bushing moves along with the cutting implement with respect to the first cup and the second cup.

19. The medical device of claim 14, wherein the spacer assembly is configured to rotate with the cutting implement.

* * * * *